(12) United States Patent
Brenner et al.

(10) Patent No.: US 7,537,897 B2
(45) Date of Patent: May 26, 2009

(54) MOLECULAR COUNTING

(75) Inventors: Sydney Brenner, Ely (GB); Stephen C. Macevicz, Cupertino, CA (US)

(73) Assignee: Population Genetics Technologies, Ltd., Cambridge (GB)

( * ) Notice: Subject to any disclaimer, the term of this patent is extended or adjusted under 35 U.S.C. 154(b) by 0 days.

(21) Appl. No.: 11/656,830

(22) Filed: Jan. 22, 2007

(65) Prior Publication Data
US 2007/0172873 A1 Jul. 26, 2007

Related U.S. Application Data

(60) Provisional application No. 60/761,578, filed on Jan. 23, 2006, provisional application No. 60/775,098, filed on Feb. 21, 2006, provisional application No. 60/777,661, filed on Feb. 27, 2006, provisional application No. 60/779,540, filed on Mar. 6, 2006, provisional application No. 60/791,561, filed on Apr. 12, 2006, provisional application No. 60/824,456, filed on Sep. 4, 2006.

(51) Int. Cl.
*C12Q 1/68* (2006.01)
*C12P 19/34* (2006.01)

(52) U.S. Cl. .......................................... 435/6; 435/91.2
(58) Field of Classification Search ........................ None
See application file for complete search history.

(56) References Cited

U.S. PATENT DOCUMENTS

| | | |
|---|---|---|
| 4,725,536 A | 2/1988 | Fritsch |
| 5,124,246 A | 6/1992 | Urdea |
| 5,149,625 A | 9/1992 | Church |
| 5,200,314 A | 4/1993 | Urdea |
| 5,424,186 A | 6/1995 | Fodor |
| 5,424,413 A | 6/1995 | Hogan |
| 5,445,934 A | 8/1995 | Fodor |
| 5,604,097 A | 2/1997 | Brenner |
| 5,635,352 A | 6/1997 | Urdea |
| 5,635,400 A | 6/1997 | Brenner |
| 5,654,413 A | 8/1997 | Brenner |
| 5,656,731 A | 8/1997 | Urdea |
| 5,658,737 A | 8/1997 | Nelson |
| 5,714,330 A | 2/1998 | Brenner |
| 5,744,305 A | 4/1998 | Fodor |
| 5,759,778 A | 6/1998 | Li et al. |
| 5,763,175 A | 6/1998 | Brenner |
| 5,846,719 A | 12/1998 | Brenner |
| 5,854,033 A | 12/1998 | Lizardi |
| 5,935,793 A | 8/1999 | Wong |
| 5,981,176 A | 11/1999 | Wallace |
| 6,013,445 A | 1/2000 | Albrecht |
| 6,046,005 A | 4/2000 | Ju et al. |
| 6,060,596 A | 5/2000 | Lerner |
| 6,117,631 A | 9/2000 | Nilson |
| 6,124,092 A | 9/2000 | O'Neill |
| 6,138,077 A | 10/2000 | Brenner |
| 6,140,489 A | 10/2000 | Brenner |
| 6,172,214 B1 | 1/2001 | Brenner |
| 6,235,475 B1 | 5/2001 | Brenner |
| 6,355,431 B1 | 3/2002 | Chee |
| 6,355,432 B1 | 3/2002 | Fodor |
| 6,406,848 B1 | 6/2002 | Bridgham |
| 6,440,667 B1 | 8/2002 | Fodor |
| 6,440,706 B1 | 8/2002 | Vogelstein et al. |
| 6,458,530 B1 | 10/2002 | Morris |
| 6,512,105 B1 | 1/2003 | Hogan |
| 6,514,699 B1 | 2/2003 | O'Neill |
| 6,544,739 B1 | 4/2003 | Fodor |

(Continued)

FOREIGN PATENT DOCUMENTS

EP 0 799 897 A1 8/1997

(Continued)

OTHER PUBLICATIONS

Brenner et al, *Gene expression analysis by massively parallel signature sequencing (MPSS) on microbead arrays* Nature Biotechnology,18:630-634 (2000).
Brenner et al. Encoded combinatorial chemistry. Proc. Natl. Acad. Sci., (1992), vol. 89, pp. 5381-5383.
Brenner et al. In Vitro cloning of complex mixtures of DNA on microbeads: physical separation of differentially expressed cDNAs. Proc. Natl. Acad. Sci., (2000) 97: 1665-1670.
Callow et al, Selective DNA amplification from complex genomes using universal double-sided adapters Nucleic Acid Research, 32: e21 (2004).
Daser et al. Interrogation of genomes by molecular copy-number counting (MCC). Nature Methods, (2006), vol. 3, No. 6, pp. 447-453.

(Continued)

*Primary Examiner*—Kenneth R. Horlick
*Assistant Examiner*—David C Thomas
(74) *Attorney, Agent, or Firm*—Bozicevic, Field & Francis, LLP

(57) ABSTRACT

The invention provides methods and compositions for counting molecules in a sample, wherein each molecule is labeled with a unique oligonucleotide tag. Such tags are amplified and identified rather than the molecules themselves; that is, the problem of counting molecules is converted into the problem of counting tags. In one aspect of the invention, molecules to be counted are labeled by sampling. That is, conjugates are formed between the molecules to be counted and oligonucleotide tags of a very large set, or repertoire.

After conjugation, a sample of conjugates is taken that is sufficiently small so that substantially every molecule has a unique oligonucleotide tag. Counting of different tags may be accomplished in a variety of ways. In one aspect, different tags may be counted by carrying out a series of sorting steps to generate successively less complex mixtures in which tags are enumerated using length-encoded "metric" tags. In another aspect, different tags may be counted by directly sequencing a sample of tags using any one of several different sequencing methodologies.

20 Claims, 37 Drawing Sheets

U.S. PATENT DOCUMENTS

| | | |
|---|---|---|
| 6,629,040 B1 | 9/2003 | Goodlett |
| 6,653,077 B1 | 11/2003 | Brenner |
| 6,753,147 B2 | 6/2004 | Vogelstein et al. |
| 6,849,404 B2 | 2/2005 | Park et al. |
| 6,858,412 B2 | 2/2005 | Willis |
| 2003/0003490 A1 | 1/2003 | Fan |
| 2003/0049616 A1 | 3/2003 | Brenner et al. |
| 2003/0104436 A1 | 6/2003 | Morris |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris |
| 2004/0259118 A1 | 12/2004 | Macevicz |
| 2005/0250147 A1 | 11/2005 | Macevicz |

FOREIGN PATENT DOCUMENTS

| | | |
|---|---|---|
| WO | WO 97/10365 A1 | 3/1997 |
| WO | WO9928505 A1 | 6/1999 |
| WO | WO02056014 A2 | 7/2002 |
| WO | WO 2005/080604 A1 | 9/2005 |
| WO | WO 2005/111242 A2 | 11/2005 |
| WO | WO 2006/102264 | 9/2006 |

OTHER PUBLICATIONS

Dunn et al. Genomic signature tags (GSTs): a system for profiling Genomic DNA. Genome Res. 2002, 12: 1756-1765.

Hirano and Fukami et al. A novel method for DNA molecular counting. Nucleic Acids Symposium Series, (2002), No. 44, 157-158.

Nakano et al. Single-molecule PCR using water-in-oil emulsion. Journal of Biotechnology, 2003, 102, 117-124.

Jarvius et al. Digital quantification using amplified single-molecule detection. Nature Methods, (2006), vol. 3, No. 9, pp. 725-727.

Lizardi et al, Mutation detection and single-molecule counting using isothermal rolling-circle amplification Nature Genetics, 19: 225-232 (1998).

Li et al. BEAMing up for detection and quantification of rare sequence variants. Nature Methods, (2006), vol. 3, No. 2, pp. 95-108.

Prod'hom et al. A reliable amplification technique for the characterization of genomic DNA sequences flanking insertion sequences. FEMS Microbiology Letters 158 (1998) pp. 75-81.

Vogelstein, et al. Digital PCR. Proc. Natl. Acad. Sci. USA, (1999), vol. 96, pp. 9236-9241.

Wang et al. Digital karyotyping. PNAS, (2002), vol. 99, No. 25, 16156-16161.

Warren et al. Transcription factor profiling in individual hematopoietic progenitors by digital RT-PCR. PNAS, 2006, vol. 103, No. 47, 17807-17812.

|    | | | | SEQ ID NO: |
|----|---|---|---|---|
| T0 | CTGTAGTGCAGC | TTACCACGTGTGGTACCGTGTGTGTG CTTCA | GATGC | TAGTCGTCAG | 22 |
| T1 | CTGTAGTGCAGC | TTACCACGTGTGGTGGGTACCTGTGTGTG CTTCA | GATGC | TAGTCGTCAG | 23 |
| T2 | CTGTAGTGCAGC | TTACCACGTGTGTGTGGTACCGTGTGTG CTTCA | GATGC | TAGTCGTCAG | 24 |
| T3 | CTGTAGTGCAGC | TTACCACGTGTGTGGGTACCTGTGTG CTTCA | GATGC | TAGTCGTCAG | 25 |
| T4 | CTGTAGTGCAGC | TTACCACGTGTGTGTGGTACCGTGTG CTTCA | GATGC | TAGTCGTCAG | 26 |
| T5 | CTGTAGTGCAGC | TTACCACGTGTGTGTGGGTACCTGTGTG CTTCA | GATGC | TAGTCGTCAG | 27 |
| T6 | CTGTAGTGCAGC | TTACCACGTGTGTGTGTGGGTACCGTGTG CTTCA | GATGC | TAGTCGTCAG | 28 |
| T7 | CTGTAGTGCAGC | TTACCACGTGTGTGTGTGGGTACCTGTGTG CTTCA | GATGC | TAGTCGTCAG | 29 |

Bbv I                                                                                                                       Sfa NI

Sequences for Metric Tags

Fig. 3

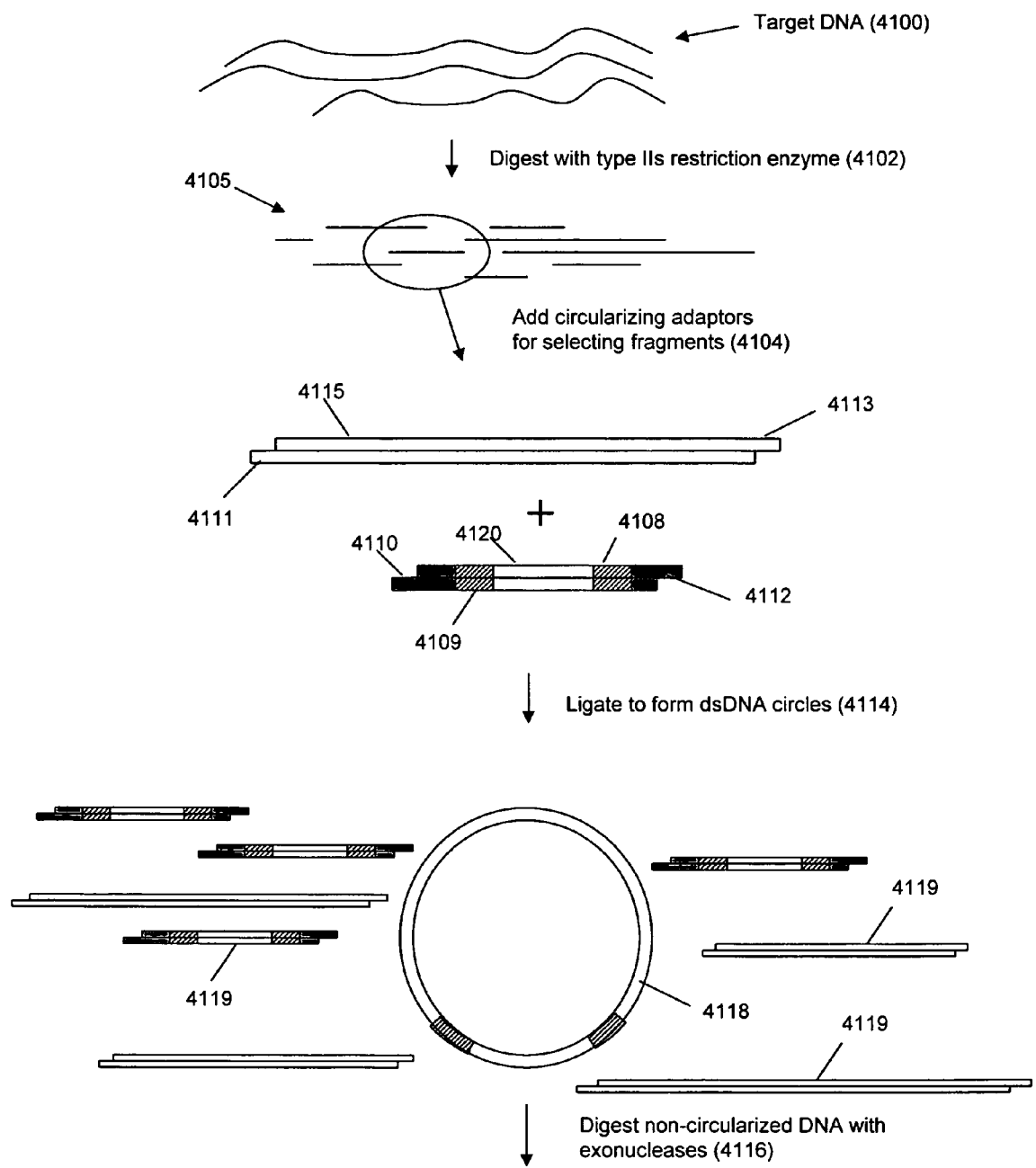

Table II

| i | R7TiR0 | R6TiR1 | R5TiR2 | R4TiR3 | R3TiR4 | R2TiR5 | R1TiR6 | R0TiR7 |
|---|--------|--------|--------|--------|--------|--------|--------|--------|
| 7 | 91 | 83 | 75 | 67 | 60 | 51 | 43 | 35 |
| 6 | 90 | 82 | 74 | 66 | 59 | 50 | 42 | 34 |
| 5 | 89 | 81 | 73 | 65 | 58 | 49 | 41 | 33 |
| 4 | 88 | 80 | 72 | 64 | 57 | 48 | 40 | 32 |
| 3 | 87 | 79 | 71 | 63 | 56 | 47 | 39 | 31 |
| 2 | 86 | 78 | 70 | 62 | 55 | 46 | 38 | 30 |
| 1 | 85 | 77 | 69 | 61 | 54 | 45 | 37 | 29 |
| 0 | 84 | 76 | 68 | 60 | 53 | 44 | 36 | 28 |

Fig. 8A

Amplification and Separation of Metric Tags

The size of the metric tag is shown on the left. Lanes indicated by 'I' (lanes 1, 6 and 11) are the mixture of the metric tags before sorting. A, C, G and T below the gel picture indicate the biotinylated nucleotide used for sorting.

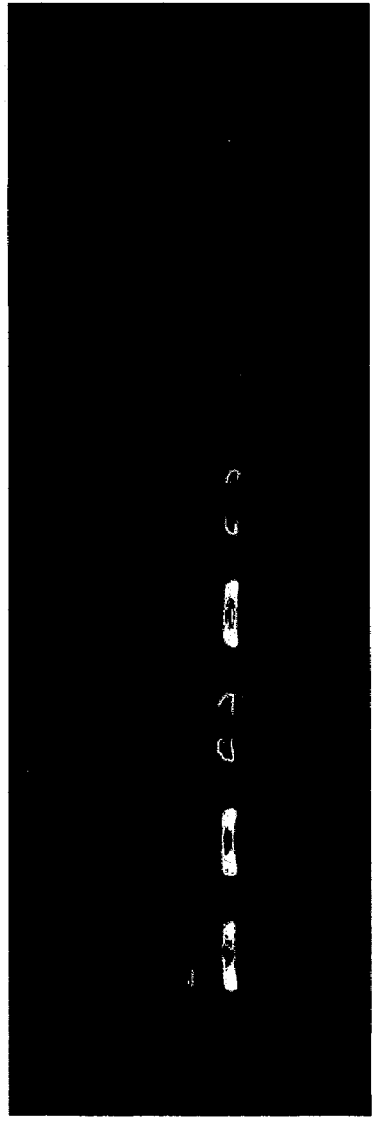

Streptavidin beads can select a biotinylated DNA sequence at $10^{-5}$–$10^{-6}$ with no background

| Lane | 1 | 2 | 3 | 4 | 5 | 6 | 7 | 8 | 9 |
|---|---|---|---|---|---|---|---|---|---|
| B7 (pmoles) | 0.1 | 0.1 | 0.01 | 0.001 | $10^{-4}$ | $10^{-5}$ | $10^{-6}$ | $10^{-7}$ | 0 |
| D3 (pmoles) | 0.1 | 0.1 | 0.1 | 0.1 | 0.1 | 0.1 | 0.1 | 0.1 | 0.1 |
| ratio | 1:1 | 1:1 | 1:10 | 1:100 | 1:$10^3$ | 1:$10^4$ | 1:$10^5$ | 1:$10^6$ | - |
| sorting | - | + | + | + | + | + | + | + | + |

A 407 base ssDNA sequence (B7) was annealed to a biotinylated primer (S1C-BIO). A 763 base ssDNA sequence (D3) was annealed to a non-biotinylated primer (S1). These two partial dsDNAs were mixed in different ratios and bound to the Dynabead Myone C1. The beads were washed and denatured to release the ssDNA. PCR was then performed on these sorted DNAs.

Fig. 10B

SEQUENCE LISTING

```
<160> NUMBER OF SEQ ID NOS: 59

<210> SEQ ID NO 1
<211> LENGTH: 52
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(11)
<223> OTHER INFORMATION: n is a, c, g or t
<220> FEATURE:
<221> NAME/KEY: misc_feature
<222> LOCATION: (17)..(19)
<223> OTHER INFORMATION: n is a, c, g or t
<220> FEATURE:
<221> NAME/KEY: misc_feature
<222> LOCATION: (25)..(25)
<223> OTHER INFORMATION: w is a or t
<220> FEATURE:
<221> NAME/KEY: misc_feature
<222> LOCATION: (26)..(26)
<223> OTHER INFORMATION: s is g or c
<220> FEATURE:
<221> NAME/KEY: misc_feature
<222> LOCATION: (27)..(27)
<223> OTHER INFORMATION: w is a or t
<220> FEATURE:
<221> NAME/KEY: misc_feature
<222> LOCATION: (28)..(28)
<223> OTHER INFORMATION: s is g or c
<220> FEATURE:
<221> NAME/KEY: misc_feature
<222> LOCATION: (29)..(33)
<223> OTHER INFORMATION: n is a, c, g or t
<220> FEATURE:
<221> NAME/KEY: misc_feature
<222> LOCATION: (39)..(42)
<223> OTHER INFORMATION: n is a, c, g or t
<220> FEATURE:
<221> NAME/KEY: misc_feature
<222> LOCATION: (49)..(52)
<223> OTHER INFORMATION: n is a, c, g or t

<400> SEQUENCE: 1
nnnnnnnnnn ngcagcnnng gatgwswsnn nnngatgcnn nnctccagnn nn            52

<210> SEQ ID NO 2
<211> LENGTH: 26
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (3)..(7)
<223> OTHER INFORMATION: n is a, c, g or t
<220> FEATURE:
<221> NAME/KEY: misc_feature
<222> LOCATION: (13)..(16)
<223> OTHER INFORMATION: n is a, c, g or t
```

```
<220> FEATURE:
<221> NAME/KEY: misc_feature
<222> LOCATION: (23)..(26)
<223> OTHER INFORMATION: n is a, c, g or t

<400> SEQUENCE: 2
agnnnnngat gcnnnnctcc agnnnn                                              26

<210> SEQ ID NO 3
<211> LENGTH: 26
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (3)..(7)
<223> OTHER INFORMATION: n is a, c, g or t
<220> FEATURE:
<221> NAME/KEY: misc_feature
<222> LOCATION: (13)..(16)
<223> OTHER INFORMATION: n is a, c, g or t
<220> FEATURE:
<221> NAME/KEY: misc_feature
<222> LOCATION: (23)..(26)
<223> OTHER INFORMATION: n is a, c, g or t

<400> SEQUENCE: 3
acnnnnngat gcnnnnctcc agnnnn                                              26

<210> SEQ ID NO 4
<211> LENGTH: 26
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (3)..(7)
<223> OTHER INFORMATION: n is a, c, g or t
<220> FEATURE:
<221> NAME/KEY: misc_feature
<222> LOCATION: (13)..(16)
<223> OTHER INFORMATION: n is a, c, g or t
<220> FEATURE:
<221> NAME/KEY: misc_feature
<222> LOCATION: (23)..(26)
<223> OTHER INFORMATION: n is a, c, g or t

<400> SEQUENCE: 4
tgnnnnngat gcnnnnctcc agnnnn                                              26

<210> SEQ ID NO 5
<211> LENGTH: 26
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (3)..(7)
<223> OTHER INFORMATION: n is a, c, g or t
<220> FEATURE:
<221> NAME/KEY: misc_feature
<222> LOCATION: (13)..(16)
<223> OTHER INFORMATION: n is a, c, g or t
<220> FEATURE:
<221> NAME/KEY: misc_feature
<222> LOCATION: (23)..(26)
<223> OTHER INFORMATION: n is a, c, g or t

<400> SEQUENCE: 5
```
tcnnnnngat gcnnnnctcc agnnnn                          26

<210> SEQ ID NO 6
<211> LENGTH: 28
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(11)
<223> OTHER INFORMATION: n is a, c, g or t
<220> FEATURE:
<221> NAME/KEY: misc_feature
<222> LOCATION: (17)..(19)
<223> OTHER INFORMATION: n is a, c, g or t
<220> FEATURE:
<221> NAME/KEY: misc_feature
<222> LOCATION: (25)..(25)
<223> OTHER INFORMATION: w is a or t
<220> FEATURE:
<221> NAME/KEY: misc_feature
<222> LOCATION: (26)..(26)
<223> OTHER INFORMATION: s is g or c
<220> FEATURE:
<221> NAME/KEY: misc_feature
<222> LOCATION: (27)..(27)
<223> OTHER INFORMATION: w is a or t
<220> FEATURE:
<221> NAME/KEY: misc_feature
<222> LOCATION: (28)..(28)
<223> OTHER INFORMATION: s is g or c

<400> SEQUENCE: 6
nnnnnnnnnn ngcagcnnng gatgwsws                        28

<210> SEQ ID NO 7
<211> LENGTH: 52
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (33)..(37)
<223> OTHER INFORMATION: n is a, c, g or t
<220> FEATURE:
<221> NAME/KEY: misc_feature
<222> LOCATION: (43)..(52)
<223> OTHER INFORMATION: n is a, c, g or t

<400> SEQUENCE: 7
nnnnnnngca gcnnnnnnnn tgtgtgtgtg tgnnnnngat gcnnnnnnnn nn        52

<210> SEQ ID NO 8
<211> LENGTH: 60
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature

```
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 8
nnnnnnngca gcnnnnnnnn tgtggtaccg tgtgtgtgtg nnnnngatgc nnnnnnnnnn      60

<210> SEQ ID NO 9
<211> LENGTH: 60
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 9
nnnnnnngca gcnnnnnnnn tgtgggtacc tgtgtgtgtg nnnnngatgc nnnnnnnnnn      60

<210> SEQ ID NO 10
<211> LENGTH: 60
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 10
nnnnnnngca gcnnnnnnnn tgtgtggtac cgtgtgtgtg nnnnngatgc nnnnnnnnnn      60

<210> SEQ ID NO 11
<211> LENGTH: 60
<212> TYPE: DNA
<213> ORGANISM: Unknown
<220> FEATURE:
<223> OTHER INFORMATION: Probe
<220> FEATURE:
```

```
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 11
nnnnnnngca gcnnnnnnnn tgtgtgggta cctgtgtgtg nnnnngatgc nnnnnnnnnn    60

<210> SEQ ID NO 12
<211> LENGTH: 60
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 12
nnnnnnngca gcnnnnnnnn tgtgtgtggt accgtgtgtg nnnnngatgc nnnnnnnnnn    60

<210> SEQ ID NO 13
<211> LENGTH: 60
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 13
nnnnnnngca gcnnnnnnnn tgtgtgtggg tacctgtgtg nnnnngatgc nnnnnnnnnn    60

<210> SEQ ID NO 14
<211> LENGTH: 60
```

```
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 14
nnnnnnngca gcnnnnnnnn tgtgtgtgtg gtaccgtgtg nnnnngatgc nnnnnnnnnn      60

<210> SEQ ID NO 15
<211> LENGTH: 60
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(7)
<223> OTHER INFORMATION: n is a, c, g or t
<220> FEATURE:
<221> NAME/KEY: misc_feature
<222> LOCATION: (13)..(20)
<223> OTHER INFORMATION: n is a, c, g or t
<220> FEATURE:
<221> NAME/KEY: misc_feature
<222> LOCATION: (41)..(45)
<223> OTHER INFORMATION: n is a, c, g or t
<220> FEATURE:
<221> NAME/KEY: misc_feature
<222> LOCATION: (51)..(60)
<223> OTHER INFORMATION: n is a, c, g or t

<400> SEQUENCE: 15
nnnnnnngca gcnnnnnnnn tgtgtgtgtg ggtacctgtg nnnnngatgc nnnnnnnnnn      60

<210> SEQ ID NO 16
<211> LENGTH: 26
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (9)..(13)
<223> OTHER INFORMATION: n is a, c, g or t
<220> FEATURE:
<221> NAME/KEY: misc_feature
<222> LOCATION: (19)..(26)
<223> OTHER INFORMATION: n is a, c, g or t

<400> SEQUENCE: 16
tgtgtgtgnn nnngatgcnn nnnnnn                                          26

<210> SEQ ID NO 17
<211> LENGTH: 12
<212> TYPE: DNA
<213> ORGANISM: Unknown
<220> FEATURE:
```

```
<223> OTHER INFORMATION: Probe

<400> SEQUENCE: 17
tgtgtgtgtg tg                                                          12

<210> SEQ ID NO 18
<211> LENGTH: 90
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(14)
<223> OTHER INFORMATION: n is a, c, g or t
<220> FEATURE:
<221> NAME/KEY: misc_feature
<222> LOCATION: (21)..(38)
<223> OTHER INFORMATION: n is a, c, g or t
<220> FEATURE:
<221> NAME/KEY: misc_feature
<222> LOCATION: (39)..(39)
<223> OTHER INFORMATION: w is a or t
<220> FEATURE:
<221> NAME/KEY: misc_feature
<222> LOCATION: (40)..(40)
<223> OTHER INFORMATION: s is g or c
<220> FEATURE:
<221> NAME/KEY: misc_feature
<222> LOCATION: (41)..(66)
<223> OTHER INFORMATION: n is a, c, g or t
<220> FEATURE:
<221> NAME/KEY: misc_feature
<222> LOCATION: (71)..(75)
<223> OTHER INFORMATION: n is a, c, g or t
<220> FEATURE:
<221> NAME/KEY: misc_feature
<222> LOCATION: (81)..(90)
<223> OTHER INFORMATION: n is a, c, g or t

<400> SEQUENCE: 18
nnnnnnnnnn nnntccaac nnnnnnnnnn nnnnnnnws nnnnnnnnnn nnnnnnnnnn         60
nnnnnntgtg nnnnngatgc nnnnnnnnnn                                        90

<210> SEQ ID NO 19
<211> LENGTH: 21
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(17)
<223> OTHER INFORMATION: n is a, c, g or t
<220> FEATURE:
<221> NAME/KEY: misc_feature
<222> LOCATION: (18)..(18)
<223> OTHER INFORMATION: w is a or t
<220> FEATURE:
<221> NAME/KEY: misc_feature
<222> LOCATION: (19)..(19)
<223> OTHER INFORMATION: s is g or c
<220> FEATURE:
<221> NAME/KEY: misc_feature
<222> LOCATION: (20)..(21)
<223> OTHER INFORMATION: n is a, c, g or t

<400> SEQUENCE: 19
nnnnnnnnnn nnnnnnnwsn n                                                 21

<210> SEQ ID NO 20
<211> LENGTH: 11
```

```
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (3)..(5)
<223> OTHER INFORMATION: n is a, c, g or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)
<223> OTHER INFORMATION: y is c or t

<400> SEQUENCE: 20
acnnnngtay c                                                          11

<210> SEQ ID NO 21
<211> LENGTH: 39
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (5)..(9)
<223> OTHER INFORMATION: n is a, c, g or t
<220> FEATURE:
<221> NAME/KEY: misc_feature
<222> LOCATION: (16)..(21)
<223> OTHER INFORMATION: n is a, c, g or t
<220> FEATURE:
<221> NAME/KEY: misc_feature
<222> LOCATION: (26)..(30)
<223> OTHER INFORMATION: n is a, c, g or t
<220> FEATURE:
<221> NAME/KEY: misc_feature
<222> LOCATION: (35)..(39)
<223> OTHER INFORMATION: n is a, c, g or t

<400> SEQUENCE: 21
gatcnnnnng catgcnnnnn ncatgnnnnn gatcnnnnn                             39

<210> SEQ ID NO 22
<211> LENGTH: 60
<212> TYPE: DNA
<213> ORGANISM: Unknown
<220> FEATURE:
<223> OTHER INFORMATION: Probe

<400> SEQUENCE: 22
ctgtagtgca gcttaccacg tgtggtaccg tgtgtgtgtg cttcagatgc tagtcgtcag      60

<210> SEQ ID NO 23
<211> LENGTH: 60
<212> TYPE: DNA
<213> ORGANISM: Unknown
<220> FEATURE:
<223> OTHER INFORMATION: Probe

<400> SEQUENCE: 23
ctgtagtgca gcttaccacg tgtgggtacc tgtgtgtgtg cttcagatgc tagtcgtcag      60

<210> SEQ ID NO 24
<211> LENGTH: 60
<212> TYPE: DNA
<213> ORGANISM: Unknown
<220> FEATURE:
```

<223> OTHER INFORMATION: Probe

<400> SEQUENCE: 24
ctgtagtgca gcttaccacg tgtgtggtac cgtgtgtgtg cttcagatgc tagtcgtcag     60

<210> SEQ ID NO 25
<211> LENGTH: 60
<212> TYPE: DNA
<213> ORGANISM: Unknown
<220> FEATURE:
<223> OTHER INFORMATION: Probe

<400> SEQUENCE: 25
ctgtagtgca gcttaccacg tgtgtgggta cctgtgtgtg cttcagatgc tagtcgtcag     60

<210> SEQ ID NO 26
<211> LENGTH: 60
<212> TYPE: DNA
<213> ORGANISM: Unknown
<220> FEATURE:
<223> OTHER INFORMATION: Probe

<400> SEQUENCE: 26
ctgtagtgca gcttaccacg tgtgtgtggt accgtgtgtg cttcagatgc tagtcgtcag     60

<210> SEQ ID NO 27
<211> LENGTH: 60
<212> TYPE: DNA
<213> ORGANISM: Unknown
<220> FEATURE:
<223> OTHER INFORMATION: Probe

<400> SEQUENCE: 27
ctgtagtgca gcttaccacg tgtgtgtggg tacctgtgtg cttcagatgc tagtcgtcag     60

<210> SEQ ID NO 28
<211> LENGTH: 60
<212> TYPE: DNA
<213> ORGANISM: Unknown
<220> FEATURE:
<223> OTHER INFORMATION: Probe

<400> SEQUENCE: 28
ctgtagtgca gcttaccacg tgtgtgtgtg gtaccgtgtg cttcagatgc tagtcgtcag     60

<210> SEQ ID NO 29
<211> LENGTH: 60
<212> TYPE: DNA
<213> ORGANISM: Unknown
<220> FEATURE:
<223> OTHER INFORMATION: Probe

<400> SEQUENCE: 29
ctgtagtgca gcttaccacg tgtgtgtgtg ggtacctgtg cttcagatgc tagtcgtcag     60

<210> SEQ ID NO 30
<211> LENGTH: 12
<212> TYPE: DNA
<213> ORGANISM: Unknown
<220> FEATURE:
<223> OTHER INFORMATION: Probe

<400> SEQUENCE: 30
tttgtagaag ta                                                        12

```
<210> SEQ ID NO 31
<211> LENGTH: 12
<212> TYPE: DNA
<213> ORGANISM: Unknown
<220> FEATURE:
<223> OTHER INFORMATION: Probe

<400> SEQUENCE: 31
atgtgattgt aa                                                              12

<210> SEQ ID NO 32
<211> LENGTH: 106
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(13)
<223> OTHER INFORMATION: n is a, c, g or t
<220> FEATURE:
<221> NAME/KEY: misc_feature
<222> LOCATION: (26)..(29)
<223> OTHER INFORMATION: n is a, c, g or t
<220> FEATURE:
<221> NAME/KEY: misc_feature
<222> LOCATION: (36)..(43)
<223> OTHER INFORMATION: n is a, c, g or t
<220> FEATURE:
<221> NAME/KEY: misc_feature
<222> LOCATION: (49)..(53)
<223> OTHER INFORMATION: n is a, c, g or t
<220> FEATURE:
<221> NAME/KEY: misc_feature
<222> LOCATION: (57)..(57)
<223> OTHER INFORMATION: n is a, c, g or t
<220> FEATURE:
<221> NAME/KEY: misc_feature
<222> LOCATION: (60)..(73)
<223> OTHER INFORMATION: n is a, c, g or t
<220> FEATURE:
<221> NAME/KEY: misc_feature
<222> LOCATION: (80)..(85)
<223> OTHER INFORMATION: n is a, c, g or t
<220> FEATURE:
<221> NAME/KEY: misc_feature
<222> LOCATION: (92)..(106)
<223> OTHER INFORMATION: n is a, c, g or t

<400> SEQUENCE: 32
nnnnnnnnnn nnngctcttc catctnnnnt ccaacnnnnn nnngcatcnn nnngacngan           60
nnnnnnnnnn nnnctccagn nnnnnggatc cnnnnnnnnn nnnnnn                         106

<210> SEQ ID NO 33
<211> LENGTH: 106
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(1)
<223> OTHER INFORMATION: biotinylated nucleotide
<220> FEATURE:
<221> NAME/KEY: misc_feature
<222> LOCATION: (1)..(13)
<223> OTHER INFORMATION: n is a, c, g or t
<220> FEATURE:
<221> NAME/KEY: misc_feature
<222> LOCATION: (26)..(29)
<223> OTHER INFORMATION: n is a, c, g or t
<220> FEATURE:
<221> NAME/KEY: misc_feature
<222> LOCATION: (36)..(43)
```

<223> OTHER INFORMATION: n is a, c, g or t
<220> FEATURE:
<221> NAME/KEY: misc_feature
<222> LOCATION: (49)..(53)
<223> OTHER INFORMATION: n is a, c, g or t
<220> FEATURE:
<221> NAME/KEY: misc_feature
<222> LOCATION: (57)..(57)
<223> OTHER INFORMATION: n is a, c, g or t
<220> FEATURE:
<221> NAME/KEY: misc_feature
<222> LOCATION: (60)..(73)
<223> OTHER INFORMATION: n is a, c, g or t
<220> FEATURE:
<221> NAME/KEY: misc_feature
<222> LOCATION: (80)..(85)
<223> OTHER INFORMATION: n is a, c, g or t
<220> FEATURE:
<221> NAME/KEY: misc_feature
<222> LOCATION: (92)..(106)
<223> OTHER INFORMATION: n is a, c, g or t

<400> SEQUENCE: 33
nnnnnnnnnn nnngctcttc catctnnnnt ccaacnnnnn nnngcatcnn nnngacngan      60
nnnnnnnnnn nnnctccagn nnnnnggatc cnnnnnnnnn nnnnnn                    106

<210> SEQ ID NO 34
<211> LENGTH: 82
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (2)..(5)
<223> OTHER INFORMATION: n is a, c, g or t
<220> FEATURE:
<221> NAME/KEY: misc_feature
<222> LOCATION: (12)..(19)
<223> OTHER INFORMATION: n is a, c, g or t
<220> FEATURE:
<221> NAME/KEY: misc_feature
<222> LOCATION: (25)..(29)
<223> OTHER INFORMATION: n is a, c, g or t
<220> FEATURE:
<221> NAME/KEY: misc_feature
<222> LOCATION: (33)..(33)
<223> OTHER INFORMATION: n is a, c, g or t
<220> FEATURE:
<221> NAME/KEY: misc_feature
<222> LOCATION: (36)..(49)
<223> OTHER INFORMATION: n is a, c, g or t
<220> FEATURE:
<221> NAME/KEY: misc_feature
<222> LOCATION: (56)..(61)
<223> OTHER INFORMATION: n is a, c, g or t
<220> FEATURE:
<221> NAME/KEY: misc_feature
<222> LOCATION: (66)..(82)
<223> OTHER INFORMATION: n is a, c, g or t

<400> SEQUENCE: 34
tnnnntccaa cnnnnnnnng catcnnnnng acngannnnn nnnnnnnnnc tccagnnnnn      60
nggatccnnn nnnnnnnnnn nn                                              82

<210> SEQ ID NO 35
<211> LENGTH: 106
<212> TYPE: DNA
<213> ORGANISM: Unknown
<220> FEATURE:
<223> OTHER INFORMATION: Probe
<220> FEATURE:
<221> NAME/KEY: misc_feature

```
<222> LOCATION: (1)..(5)
<223> OTHER INFORMATION: n is a, c, g or t
<220> FEATURE:
<221> NAME/KEY: misc_feature
<222> LOCATION: (1)..(1)
<223> OTHER INFORMATION: biotinylated nucleotide
<220> FEATURE:
<221> NAME/KEY: misc_feature
<222> LOCATION: (6)..(15)
<223> OTHER INFORMATION: n is a, c, g, or t
<220> FEATURE:
<221> NAME/KEY: misc_feature
<222> LOCATION: (22)..(27)
<223> OTHER INFORMATION: n is a, c, g or t
<220> FEATURE:
<221> NAME/KEY: misc_feature
<222> LOCATION: (34)..(47)
<223> OTHER INFORMATION: n is a, c, g or t
<220> FEATURE:
<221> NAME/KEY: misc_feature
<222> LOCATION: (54)..(58)
<223> OTHER INFORMATION: n is a, c, g or t
<220> FEATURE:
<221> NAME/KEY: misc_feature
<222> LOCATION: (64)..(71)
<223> OTHER INFORMATION: n is a, c, g or t
<220> FEATURE:
<221> NAME/KEY: misc_feature
<222> LOCATION: (78)..(81)
<223> OTHER INFORMATION: n is a, c, g or t
<220> FEATURE:
<221> NAME/KEY: misc_feature
<222> LOCATION: (94)..(106)
<223> OTHER INFORMATION: n is a, c, g or t

<400> SEQUENCE: 35
nnnnnnnnnn nnnnnggatc cnnnnnnctg gagnnnnnnn nnnnnnntca gtcnnnnnga      60
tgcnnnnnnn ngttggannn nagatggaag agcnnnnnnn nnnnnn                   106

<210> SEQ ID NO 36
<211> LENGTH: 86
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(13)
<223> OTHER INFORMATION: n is a, c, g or t
<220> FEATURE:
<221> NAME/KEY: misc_feature
<222> LOCATION: (26)..(29)
<223> OTHER INFORMATION: n is a, c, g or t
<220> FEATURE:
<221> NAME/KEY: misc_feature
<222> LOCATION: (36)..(43)
<223> OTHER INFORMATION: n is a, c, g or t
<220> FEATURE:
<221> NAME/KEY: misc_feature
<222> LOCATION: (49)..(53)
<223> OTHER INFORMATION: n is a, c, g or t
<220> FEATURE:
<221> NAME/KEY: misc_feature
<222> LOCATION: (60)..(73)
<223> OTHER INFORMATION: n is a, c, g or t
<220> FEATURE:
<221> NAME/KEY: misc_feature
<222> LOCATION: (80)..(85)
<223> OTHER INFORMATION: n is a, c, g or t

<400> SEQUENCE: 36
nnnnnnnnnn nnngctcttc catctnnnnt ccaacnnnnn nnngcatcnn nnngactgan      60
nnnnnnnnnn nnnctccagn nnnnng                                          86
```

```
<210> SEQ ID NO 37
<211> LENGTH: 87
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(13)
<223> OTHER INFORMATION: n is a, c, g or t
<220> FEATURE:
<221> NAME/KEY: misc_feature
<222> LOCATION: (26)..(29)
<223> OTHER INFORMATION: n is a, c, g or t
<220> FEATURE:
<221> NAME/KEY: misc_feature
<222> LOCATION: (36)..(43)
<223> OTHER INFORMATION: n is a, c, g or t
<220> FEATURE:
<221> NAME/KEY: misc_feature
<222> LOCATION: (49)..(53)
<223> OTHER INFORMATION: n is a, c, g or t
<220> FEATURE:
<221> NAME/KEY: misc_feature
<222> LOCATION: (60)..(73)
<223> OTHER INFORMATION: n is a, c, g or t
<220> FEATURE:
<221> NAME/KEY: misc_feature
<222> LOCATION: (80)..(85)
<223> OTHER INFORMATION: n is a, c, g or t

<400> SEQUENCE: 37
nnnnnnnnnn nnngctcttc catctnnnnt ccaacnnnnn nnngcatcnn nnngactgan      60
nnnnnnnnnn nnnctccagn nnnnngg                                         87

<210> SEQ ID NO 38
<211> LENGTH: 172
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(13)
<223> OTHER INFORMATION: n is a, c, g or t
<220> FEATURE:
<221> NAME/KEY: misc_feature
<222> LOCATION: (26)..(29)
<223> OTHER INFORMATION: n is a, c, g or t
<220> FEATURE:
<221> NAME/KEY: misc_feature
<222> LOCATION: (36)..(43)
<223> OTHER INFORMATION: n is a, c, g or t
<220> FEATURE:
<221> NAME/KEY: misc_feature
<222> LOCATION: (49)..(53)
<223> OTHER INFORMATION: n is a, c, g or t
<220> FEATURE:
<221> NAME/KEY: misc_feature
<222> LOCATION: (60)..(73)
<223> OTHER INFORMATION: n is a, c, g or t
<220> FEATURE:
<221> NAME/KEY: misc_feature
<222> LOCATION: (80)..(85)
<223> OTHER INFORMATION: n is a, c, g or t
<220> FEATURE:
<221> NAME/KEY: misc_feature
<222> LOCATION: (92)..(95)
<223> OTHER INFORMATION: n is a, c, g or t
<220> FEATURE:
<221> NAME/KEY: misc_feature
<222> LOCATION: (102)..(109)
<223> OTHER INFORMATION: n is a, c, g or t
<220> FEATURE:
<221> NAME/KEY: misc_feature
```

<222> LOCATION: (115)..(119)
<223> OTHER INFORMATION: n is a, c, g or t
<220> FEATURE:
<221> NAME/KEY: misc_feature
<222> LOCATION: (126)..(139)
<223> OTHER INFORMATION: n is a, c, g or t
<220> FEATURE:
<221> NAME/KEY: misc_feature
<222> LOCATION: (146)..(151)
<223> OTHER INFORMATION: n is a, c, g or t
<220> FEATURE:
<221> NAME/KEY: misc_feature
<222> LOCATION: (158)..(172)
<223> OTHER INFORMATION: n is a, c, g or t

<400> SEQUENCE: 38
nnnnnnnnnn nnngctcttc catctnnnnt ccaacnnnnn nnngcatcnn nnngactgan      60
nnnnnnnnnn nnnctccagn nnnnnggatc tnnnntccaa cnnnnnnnng catcnnnnng    120
acagannnnn nnnnnnnnnc tccagnnnnn nggatccnnn nnnnnnnnnn nn            172

<210> SEQ ID NO 39
<211> LENGTH: 172
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(13)
<223> OTHER INFORMATION: n is a, c, g or t
<220> FEATURE:
<221> NAME/KEY: misc_feature
<222> LOCATION: (1)..(1)
<223> OTHER INFORMATION: biotinylated nucleotide
<220> FEATURE:
<221> NAME/KEY: misc_feature
<222> LOCATION: (26)..(29)
<223> OTHER INFORMATION: n is a, c, g or t
<220> FEATURE:
<221> NAME/KEY: misc_feature
<222> LOCATION: (36)..(43)
<223> OTHER INFORMATION: n is a, c, g or t
<220> FEATURE:
<221> NAME/KEY: misc_feature
<222> LOCATION: (49)..(53)
<223> OTHER INFORMATION: n is a, c, g or t
<220> FEATURE:
<221> NAME/KEY: misc_feature
<222> LOCATION: (60)..(73)
<223> OTHER INFORMATION: n is a, c, g or t
<220> FEATURE:
<221> NAME/KEY: misc_feature
<222> LOCATION: (80)..(85)
<223> OTHER INFORMATION: n is a, c, g or t
<220> FEATURE:
<221> NAME/KEY: misc_feature
<222> LOCATION: (92)..(95)
<223> OTHER INFORMATION: n is a, c, g or t
<220> FEATURE:
<221> NAME/KEY: misc_feature
<222> LOCATION: (102)..(109)
<223> OTHER INFORMATION: n is a, c, g or t
<220> FEATURE:
<221> NAME/KEY: misc_feature
<222> LOCATION: (115)..(119)
<223> OTHER INFORMATION: n is a, c, g or t
<220> FEATURE:
<221> NAME/KEY: misc_feature
<222> LOCATION: (126)..(139)
<223> OTHER INFORMATION: n is a, c, g or t
<220> FEATURE:
<221> NAME/KEY: misc_feature
<222> LOCATION: (146)..(151)
<223> OTHER INFORMATION: n is a, c, g or t
<220> FEATURE:

<221> NAME/KEY: misc_feature
<222> LOCATION: (158)..(172)
<223> OTHER INFORMATION: n is a, c, g or t

<400> SEQUENCE: 39
nnnnnnnnnn nnngctcttc catctnnnnt ccaacnnnnn nnngcatcnn nnngactgan    60
nnnnnnnnnn nnnctccagn nnnnnggatc tnnnntccaa cnnnnnnnng catcnnnnng   120
acagannnnn nnnnnnnnnc tccagnnnnn nggatccnnn nnnnnnnnnn nn          172

<210> SEQ ID NO 40
<211> LENGTH: 128
<212> TYPE: DNA
<213> ORGANISM: Unknown
<220> FEATURE:
<223> OTHER INFORMATION: Prove
<220> FEATURE:
<221> NAME/KEY: misc_feature
<222> LOCATION: (2)..(5)
<223> OTHER INFORMATION: n is a, c, g or t
<220> FEATURE:
<221> NAME/KEY: misc_feature
<222> LOCATION: (12)..(19)
<223> OTHER INFORMATION: n is a, c, g or t
<220> FEATURE:
<221> NAME/KEY: misc_feature
<222> LOCATION: (25)..(29)
<223> OTHER INFORMATION: n is a, c, g or t
<220> FEATURE:
<221> NAME/KEY: misc_feature
<222> LOCATION: (36)..(49)
<223> OTHER INFORMATION: n is a, c, g or t
<220> FEATURE:
<221> NAME/KEY: misc_feature
<222> LOCATION: (56)..(61)
<223> OTHER INFORMATION: n is a, c, g or t
<220> FEATURE:
<221> NAME/KEY: misc_feature
<222> LOCATION: (68)..(71)
<223> OTHER INFORMATION: n is a, c, g or t
<220> FEATURE:
<221> NAME/KEY: misc_feature
<222> LOCATION: (78)..(85)
<223> OTHER INFORMATION: n is a, c, g or t
<220> FEATURE:
<221> NAME/KEY: misc_feature
<222> LOCATION: (91)..(95)
<223> OTHER INFORMATION: n is a, c, g or t
<220> FEATURE:
<221> NAME/KEY: misc_feature
<222> LOCATION: (102)..(115)
<223> OTHER INFORMATION: n is a, c, g or t
<220> FEATURE:
<221> NAME/KEY: misc_feature
<222> LOCATION: (122)..(127)
<223> OTHER INFORMATION: n is a, c, g or t

<400> SEQUENCE: 40
tnnnntccaa cnnnnnnnng catcnnnnng actgannnnn nnnnnnnnnc tccagnnnnn    60
nggatctnnn ntccaacnnn nnnnngcatc nnnnngacag annnnnnnnn nnnnnctcca   120 gnnnnnng                                                            128

<210> SEQ ID NO 41
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (2)..(5)
<223> OTHER INFORMATION: n is a, c, g or t

```
<220> FEATURE:
<221> NAME/KEY: misc_feature
<222> LOCATION: (12)..(19)
<223> OTHER INFORMATION: n is a, c, g or t
<220> FEATURE:
<221> NAME/KEY: misc_feature
<222> LOCATION: (25)..(29)
<223> OTHER INFORMATION: n is a, c, g or t
<220> FEATURE:
<221> NAME/KEY: misc_feature
<222> LOCATION: (36)..(49)
<223> OTHER INFORMATION: n is a, c, g or t
<220> FEATURE:
<221> NAME/KEY: misc_feature
<222> LOCATION: (56)..(61)
<223> OTHER INFORMATION: n is a, c, g or t

<400> SEQUENCE: 41
tnnnntccaa cnnnnnnnng catcnnnnng actgannnnn nnnnnnnnnc tccagnnnnn    60 ng                                                                  62

<210> SEQ ID NO 42
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (2)..(5)
<223> OTHER INFORMATION: n is a, c, g or t
<220> FEATURE:
<221> NAME/KEY: misc_feature
<222> LOCATION: (12)..(19)
<223> OTHER INFORMATION: n is a, c, g or t
<220> FEATURE:
<221> NAME/KEY: misc_feature
<222> LOCATION: (25)..(29)
<223> OTHER INFORMATION: n is a, c, g or t
<220> FEATURE:
<221> NAME/KEY: misc_feature
<222> LOCATION: (36)..(49)
<223> OTHER INFORMATION: n is a, c, g or t
<220> FEATURE:
<221> NAME/KEY: misc_feature
<222> LOCATION: (56)..(61)
<223> OTHER INFORMATION: n is a, c, g or t

<400> SEQUENCE: 42
tnnnntccaa cnnnnnnnng catcnnnnng acagannnnn nnnnnnnnnc tccagnnnnn    60 ng                                                                  62

<210> SEQ ID NO 43
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (2)..(5)
<223> OTHER INFORMATION: n is a, c, g or t
<220> FEATURE:
<221> NAME/KEY: misc_feature
<222> LOCATION: (12)..(19)
<223> OTHER INFORMATION: n is a, c, g or t
<220> FEATURE:
<221> NAME/KEY: misc_feature
<222> LOCATION: (25)..(29)
<223> OTHER INFORMATION: n is a, c, g or t
<220> FEATURE:
<221> NAME/KEY: misc_feature
<222> LOCATION: (36)..(49)
```

<223> OTHER INFORMATION: n is a, c, g or t
<220> FEATURE:
<221> NAME/KEY: misc_feature
<222> LOCATION: (56)..(61)
<223> OTHER INFORMATION: n is a, c, g or t

<400> SEQUENCE: 43
tnnnntccaa cnnnnnnnng catcnnnnng acggannnnn nnnnnnnnnc tccagnnnnn    60 ng                                                                  62

<210> SEQ ID NO 44
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (2)..(5)
<223> OTHER INFORMATION: n is a, c, g or t
<220> FEATURE:
<221> NAME/KEY: misc_feature
<222> LOCATION: (12)..(19)
<223> OTHER INFORMATION: n is a, c, g or t
<220> FEATURE:
<221> NAME/KEY: misc_feature
<222> LOCATION: (25)..(29)
<223> OTHER INFORMATION: n is a, c, g or t
<220> FEATURE:
<221> NAME/KEY: misc_feature
<222> LOCATION: (36)..(49)
<223> OTHER INFORMATION: n is a, c, g or t
<220> FEATURE:
<221> NAME/KEY: misc_feature
<222> LOCATION: (56)..(61)
<223> OTHER INFORMATION: n is a, c, g or t

<400> SEQUENCE: 44
tnnnntccaa cnnnnnnnng catcnnnnng acggannnnn nnnnnnnnnc tccagnnnnn    60 ng                                                                  62

<210> SEQ ID NO 45
<211> LENGTH: 32
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t

<400> SEQUENCE: 45
nnnntccaac nnnnnnnngc atcnnnnnga ct                                 32

<210> SEQ ID NO 46
<211> LENGTH: 32
<212> TYPE: DNA
<213> ORGANISM: Unknown
<220> FEATURE:
<223> OTHER INFORMATION: Probe
<220> FEATURE:
<221> NAME/KEY: misc_feature

```
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t

<400> SEQUENCE: 46
nnnntccaac nnnnnnnngc atcnnnnnga ca                             32

<210> SEQ ID NO 47
<211> LENGTH: 30
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (5)..(18)
<223> OTHER INFORMATION: n is a, c, g or t
<220> FEATURE:
<221> NAME/KEY: misc_feature
<222> LOCATION: (25)..(30)
<223> OTHER INFORMATION: n is a, c, g or t

<400> SEQUENCE: 47
ccgannnnnn nnnnnnnnct ccagnnnnnn                                30

<210> SEQ ID NO 48
<211> LENGTH: 30
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (5)..(18)
<223> OTHER INFORMATION: n is a, c, g or t
<220> FEATURE:
<221> NAME/KEY: misc_feature
<222> LOCATION: (25)..(30)
<223> OTHER INFORMATION: n is a, c, g or t

<400> SEQUENCE: 48
cggannnnnn nnnnnnnnct ccagnnnnnn                                30

<210> SEQ ID NO 49
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t
<220> FEATURE:
<221> NAME/KEY: misc_feature
<222> LOCATION: (37)..(50)
<223> OTHER INFORMATION: n is a, c, g or t
<220> FEATURE:
```

```
<221> NAME/KEY: misc_feature
<222> LOCATION: (57)..(62)
<223> OTHER INFORMATION: n is a, c, g or t

<400> SEQUENCE: 49
nnnntccaac nnnnnnnngc atcnnnnnga ctccgannnn nnnnnnnnnn ctccagnnnn      60 nn                                                                    62

<210> SEQ ID NO 50
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t
<220> FEATURE:
<221> NAME/KEY: misc_feature
<222> LOCATION: (37)..(50)
<223> OTHER INFORMATION: n is a, c, g or t
<220> FEATURE:
<221> NAME/KEY: misc_feature
<222> LOCATION: (57)..(62)
<223> OTHER INFORMATION: n is a, c, g or t

<400> SEQUENCE: 50
nnnntccaac nnnnnnnngc atcnnnnnga ctcggannnn nnnnnnnnnn ctccagnnnn      60 nn                                                                    62

<210> SEQ ID NO 51
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t
<220> FEATURE:
<221> NAME/KEY: misc_feature
<222> LOCATION: (37)..(50)
<223> OTHER INFORMATION: n is a, c, g or t
<220> FEATURE:
<221> NAME/KEY: misc_feature
<222> LOCATION: (57)..(62)
<223> OTHER INFORMATION: n is a, c, g or t

<400> SEQUENCE: 51
nnnntccaac nnnnnnnngc atcnnnnnga caccgannnn nnnnnnnnnn ctccagnnnn      60 nn                                                                    62
```

<210> SEQ ID NO 52
<211> LENGTH: 62
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t
<220> FEATURE:
<221> NAME/KEY: misc_feature
<222> LOCATION: (37)..(50)
<223> OTHER INFORMATION: n is a, c, g or t
<220> FEATURE:
<221> NAME/KEY: misc_feature
<222> LOCATION: (57)..(62)
<223> OTHER INFORMATION: n is a, c, g or t

<400> SEQUENCE: 52
nnnntccaac nnnnnnnngc atcnnnnnga cacggannnn nnnnnnnnnn ctccagnnnn      60 nn                                                                    62

<210> SEQ ID NO 53
<211> LENGTH: 36
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t
<220> FEATURE:
<221> NAME/KEY: misc_feature
<222> LOCATION: (32)..(32)
<223> OTHER INFORMATION: w is a or t
<220> FEATURE:
<221> NAME/KEY: misc_feature
<222> LOCATION: (36)..(36)
<223> OTHER INFORMATION: s is c or g

<400> SEQUENCE: 53
nnnntccaac nnnnnnnngc atcnnnnnga cwgacs                               36

<210> SEQ ID NO 54
<211> LENGTH: 34
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (2)..(2)
<223> OTHER INFORMATION: w is a or t
<220> FEATURE:
<221> NAME/KEY: misc_feature
<222> LOCATION: (6)..(6)

```
<223> OTHER INFORMATION: s is g or c
<220> FEATURE:
<221> NAME/KEY: misc_feature
<222> LOCATION: (9)..(22)
<223> OTHER INFORMATION: n is a, c, g or t
<220> FEATURE:
<221> NAME/KEY: misc_feature
<222> LOCATION: (29)..(34)
<223> OTHER INFORMATION: n is a, c, g or t

<400> SEQUENCE: 54
cwgacsgann nnnnnnnnnn nnctccagnn nnnn                                34

<210> SEQ ID NO 55
<211> LENGTH: 70
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g, or t
<220> FEATURE:
<221> NAME/KEY: misc_feature
<222> LOCATION: (32)..(32)
<223> OTHER INFORMATION: w is a or t
<220> FEATURE:
<221> NAME/KEY: misc_feature
<222> LOCATION: (38)..(38)
<223> OTHER INFORMATION: w is a or t
<220> FEATURE:
<221> NAME/KEY: misc_feature
<222> LOCATION: (42)..(42)
<223> OTHER INFORMATION: s is g or c
<220> FEATURE:
<221> NAME/KEY: misc_feature
<222> LOCATION: (45)..(58)
<223> OTHER INFORMATION: n is a, c, g or t
<220> FEATURE:
<221> NAME/KEY: misc_feature
<222> LOCATION: (65)..(70)
<223> OTHER INFORMATION: n is a, c, g or t

<400> SEQUENCE: 55
nnnntccaac nnnnnnnngc atcnnnnnga cwgacscwga csgannnnnn nnnnnnnnct    60 ccagnnnnnn                                                          70

<210> SEQ ID NO 56
<211> LENGTH: 44
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t
```

```
<220> FEATURE:
<221> NAME/KEY: misc_feature
<222> LOCATION: (32)..(32)
<223> OTHER INFORMATION: w is a or t
<220> FEATURE:
<221> NAME/KEY: misc_feature
<222> LOCATION: (36)..(36)
<223> OTHER INFORMATION: s is g or c
<220> FEATURE:
<221> NAME/KEY: misc_feature
<222> LOCATION: (40)..(40)
<223> OTHER INFORMATION: w is a or t
<220> FEATURE:
<221> NAME/KEY: misc_feature
<222> LOCATION: (44)..(44)
<223> OTHER INFORMATION: s is g or c

<400> SEQUENCE: 56
nnnntccaac nnnnnnnngc atcnnnnnga cwgacsgacw gacs                    44

<210> SEQ ID NO 57
<211> LENGTH: 42
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (2)..(2)
<223> OTHER INFORMATION: w is a or t
<220> FEATURE:
<221> NAME/KEY: misc_feature
<222> LOCATION: (6)..(6)
<223> OTHER INFORMATION: s is g or c
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (14)..(14)
<223> OTHER INFORMATION: s is g or c
<220> FEATURE:
<221> NAME/KEY: misc_feature
<222> LOCATION: (17)..(30)
<223> OTHER INFORMATION: n is a, c, g or t
<220> FEATURE:
<221> NAME/KEY: misc_feature
<222> LOCATION: (37)..(42)
<223> OTHER INFORMATION: n is a, c, g or t

<400> SEQUENCE: 57
cwgacsgacw gacsgannnn nnnnnnnnnn ctccagnnnn nn                      42

<210> SEQ ID NO 58
<211> LENGTH: 88
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (11)..(18)
<223> OTHER INFORMATION: n is a, c, g or t
<220> FEATURE:
<221> NAME/KEY: misc_feature
<222> LOCATION: (24)..(28)
<223> OTHER INFORMATION: n is a, c, g or t
<220> FEATURE:
<221> NAME/KEY: misc_feature
<222> LOCATION: (32)..(32)
```

```
<223> OTHER INFORMATION: w is a or t
<220> FEATURE:
<221> NAME/KEY: misc_feature
<222> LOCATION: (36)..(36)
<223> OTHER INFORMATION: s is g or c
<220> FEATURE:
<221> NAME/KEY: misc_feature
<222> LOCATION: (40)..(40)
<223> OTHER INFORMATION: w is a or t
<220> FEATURE:
<221> NAME/KEY: misc_feature
<222> LOCATION: (44)..(44)
<223> OTHER INFORMATION: s is g or c
<220> FEATURE:
<221> NAME/KEY: misc_feature
<222> LOCATION: (48)..(48)
<223> OTHER INFORMATION: w is a or t
<220> FEATURE:
<221> NAME/KEY: misc_feature
<222> LOCATION: (52)..(52)
<223> OTHER INFORMATION: s is g or c
<220> FEATURE:
<221> NAME/KEY: misc_feature
<222> LOCATION: (56)..(56)
<223> OTHER INFORMATION: w is a or t
<220> FEATURE:
<221> NAME/KEY: misc_feature
<222> LOCATION: (60)..(60)
<223> OTHER INFORMATION: s is g or c
<220> FEATURE:
<221> NAME/KEY: misc_feature
<222> LOCATION: (63)..(76)
<223> OTHER INFORMATION: n is a, c, g or t
<220> FEATURE:
<221> NAME/KEY: misc_feature
<222> LOCATION: (83)..(88)
<223> OTHER INFORMATION: n is a, c, g or t

<400> SEQUENCE: 58
nnnntccaac nnnnnnnngc atcnnnnnga cwgacsgacw gacsgacwga csgacwgacs    60
gannnnnnnn nnnnnnctcc agnnnnnn                                       88

<210> SEQ ID NO 59
<211> LENGTH: 11
<212> TYPE: DNA
<213> ORGANISM: Unknown
<220> FEATURE:
<223> OTHER INFORMATION: Probe

<400> SEQUENCE: 59
agtccttaac t                                                         11
```

MOLECULAR COUNTING

CROSS REFERENCE TO RELATED APPLICATIONS

This application claims priority from prior U.S. applications having the following serial numbers and filing dates: Ser. No. 60/761,578 filed 23 Jan. 2006; Ser. No. 60/775,098 filed 21 Feb. 2006; Ser. No. 60/777,661 filed 27 Feb. 2006; Ser. No. 60/779,540 filed 6 Mar. 2006; Ser. No. 60/791,561 filed 12 Apr. 2006; and Ser. No. 60/824,456 filed 4 Sep. 2006, which applications are each incorporated herein in their entireties by reference.

FIELD OF THE INVENTION

The present invention relates to methods and compositions for analyzing populations of polynucleotides, and more particularly, to methods and compositions for counting molecules in a sample.

BACKGROUND

The difference between health and disease frequently depends on whether or not certain biomolecules of an organism are within tightly controlled tolerances. This has led to an active search for quantitative molecular biomarkers to assess states of health and disease, e.g. Slamon et al, Science, 240: 1795-1798 (1988); Sidransky, Nature Reviews Cancer, 2:210-219 (2002); Pinkel and Albertson, Ann. Rev. Genomics Hum. Genet., 6:331-354 (2005); Stankiewicz and Lupski, Trends in Genetics, 18:74-82 (2002); Hanna, Oncology, 61 (suppl 2):22-30 (2001); Cronin et al, Am. J. Pathol., 164:35-42 (2004); and the like. Although many techniques are available to measure amounts of biomolecules, they each have trade-offs with respect to sensitivity, selectivity, dynamic range, convenience, robustness, cost, and so on. For nucleic acid measurements, most techniques provide analog readouts, in that measured amounts are correlated with signal intensities, e.g. Pinkel and Albertson, Nature Genetics Supplement, 37:S11-S17 (2005); Lockhart et al, Nature Biotechnology, 14:1675-1680 (1996). Digital measurements of polynucleotides have been made, wherein measured amounts are correlated with integral numbers of countable events, e.g. numbers of sequence tags; however, even though such measurements have significant statistical advantages, they are usually more difficult and expensive to implement, e.g. Brenner et al, Nature Biotechnology, 18:630-634 (2000); Velculescu et al, Science, 270:484-487 (1995); Dressman et al, Proc. Natl. Acad. Sci., 100:8817-8822 (2003); Audic and Clayerie, Genome Research, 7:986-995 (1997).

It would be advantageous to many pure and applied fields in the biosciences if there was available a method for conveniently and accurately providing digital measurements of quantities of biomolecules in a cost effective manner. Such a method would be particularly useful in the medical and research fields for determining a wide variety of quantities, including genetic copy number variation, aneuploidies, such as chromosome 21 trisomy, gene expression variation, methylation variation, and the like.

SUMMARY OF THE INVENTION

The invention provides a method of counting molecules in a sample by converting the problem of counting molecules into one of counting sequences of oligonucleotide tags. That is, in accordance with the invention, molecules to be counted in a sample are each labeled with a unique oligonucleotide tag. Such tags are then amplified and identified. The number of different oligonucleotide tags detected, or counted, is equal to the number of molecules in the sample. In one aspect, molecules to be counted are each associated with or linked to an oligonucleotide tag randomly selected from a set that is much larger than the number of target molecules. This ensures with high probability that substantially every target molecule is associated with a unique oligonucleotide tag. In the process of linking or associating such target molecule with an oligonucleotide tag, a selected probe containing the tag is formed that can be selectively amplified and/or otherwise manipulated. That is, in one aspect, oligonucleotide tags of selected probes are isolated from other oligonucleotide tags by physical separation or by the resistance of the selected probe to degradation by at least one nuclease activity. In one aspect, the different oligonucleotide tags of the selected probes, and hence, the number of target molecules, is determined by sequencing a sample of the oligonucleotide tags amplified from the selected probes.

In another aspect of the invention, oligonucleotide tags are provided that comprise a collection of subunits, or "words," that are selected from a defined set of subunits. In one embodiment, such collections of subunits are arranged into a concatenate to form an oligonucleotide tag. In one aspect, such concatenates may be formed by combinatorial synthesis. Thus, if oligonucleotide tags comprised K subunits and if the defined set of subunits has three members, then at each position, 1 through K, one of the three subunits is present. In another aspect, no two tags of such a collection of subunits is the same; thus, an oligonucleotide tag comprising a concatenate of such subunits has a different subunit at each position.

In one aspect, the number of subunits in a set may vary between 2 and 4, inclusive; however, preferably, the number of subunits in a set is two. An oligonucleotide tag made up of subunits from a set of size two is referred to herein as a "binary tag." Subunits of binary tags can have lengths that vary widely. In one aspect, subunits of binary tags have lengths in the range of from 1 to 6 nucleotides, and more preferably, in the range of from 2 to 4 nucleotides. In one preferred embodiment, subunits of binary tags are dinucleotides, such as those described more fully below.

In one form of the invention, oligonucleotide tags are counted by successively sorting them into separate subsets based on the identity of the subunits at different positions within the tags, preferably using a sorting by sequence process as disclosed by Brenner, PCT publication WO 2005/080604, which is incorporated by reference. After each sorting step, each subset is tested for the presence or absence of oligonucleotide tags. Sorting takes place only once at a position and continues position by position until no oligonucleotide tag is detected in one of the sorted subsets. When this condition is reached, the number of molecules (and number of different oligonucleotide tags) can be determined. For binary tags, the number of molecules is proportional to $2^r$, where r is the number of sorting steps required to reach a subset empty of binary tags.

In one aspect, the invention provides a method for determining a number of target molecules in a sample carried out by the following steps: (a) providing molecule-tag conjugates each comprising an oligonucleotide tag such that substantially every different molecule of the sample is attached to a different oligonucleotide tag, each oligonucleotide tag comprising a concatenation of subunits selected from a set of subunits, each subunit being a different nucleotide or oligonucleotide and having a position, and the set of subunits having a size of from 2 to 6 members; (b) dividing the oligonucleotide tags of the molecule-tag conjugates into aliquots by sorting the oligonucleotide tags according to the identity of a subunit within a first or a successive position; and (c) repeating step (b) for at least one aliquot in each successive application of step (b) until at least one aliquot has no oligonucleotide tags that can be separated into aliquots, thereby determining the number of molecules in the sample to be in the range determined by a first number equal to the size of the subset taken to a power equal to the lowest number of times step (b) has been applied to produce an aliquot having no oligonucleotide tags less one and a second number equal to the size of the subset taken to a power equal to the greatest number of times step (b) has been applied to produce an aliquot having no oligonucleotide tags less one.

In another aspect, a method of the invention for estimating a number of target polynucleotides in a mixture is carried out with the following steps: (a) labeling by sampling each target polynucleotide in the mixture so that substantially every target polynucleotide has a unique oligonucleotide tag; (b) amplifying the oligonucleotide tags of the labeled target polynucleotides; and (c) determining the number of different oligonucleotide tags in a sample of amplified oligonucleotide tags, thereby estimating the number of target polynucleotide in the mixture. In one embodiment of this aspect, whenever size-based tags (i.e. "metric tags") are employed, the number of different oligonucleotide tags in a sample is determined by counting the number of oligonucleotide tags of different sizes, e.g. by electrophoretic separation, chromatographic separation, mass spectrometry analysis, or the like. In another embodiment of this aspect, the number of different oligonucleotide tags in a sample is determined by determining the nucleotide sequences thereof and then counting the number of oligonucleotide tags with different sequences.

In another aspect, a method of determining a number of target polynucleotides is implemented by the following steps: (a) providing for each target polynucleotide a plurality of nucleic acid probes specific for the target polynucleotide, each nucleic acid probe having a different oligonucleotide tag; (b) combining in a reaction mixture the plurality of nucleic acid probes with the target polynucleotides so that substantially every target polynucleotides associates with a nucleic acid probe to form a selected nucleic acid probe that is resistant to at least one nuclease activity, the plurality of nucleic acid probes having a size sufficiently greater than the number of target polynucleotides so that substantially every selected nucleic acid probe has a unique oligonucleotide tag; (c) isolating the selected nucleic acid probes by treating the reaction mixture with one or more nuclease activities; and (d) determining nucleotide sequences of oligonucleotide tags in a sample of isolated selected nucleic acid probes to determine the number of different oligonucleotide tags therein, thereby determining the number of target polynucleotide in the mixture.

In still another aspect, the invention provides methods and compositions for detecting nucleic acid probes by sequencing probe-specific oligonucleotide tags. In this aspect, probes from a collection of probes, e.g. circularizable probes specific for different single nucleotide polymorphisms, are each labeled with a unique oligonucleotide tag. After combining with target polynucleotides, selected nucleic acid probes are generated from the probes whenever their respective target polynucleotide is present in a sample, e.g. by way of a template-driven extension and/or ligation reaction, or the like. The nucleotide sequences of the selected nucleic acid probes are then determined in order to determine which target polynucleotides are present. In one embodiment, the sequences of oligonucleotide tags of selected nucleic acid probes are determined after amplification by a sequencing by synthesis process.

The present invention provides compositions and methods for making digital measurements of biomolecules, and has applications in the measurement of genetic copy number variation, aneuploidy, methylation states, gene expression changes, and the like, particularly under conditions of limiting sample availability.

BRIEF DESCRIPTION OF THE DRAWINGS

FIG. 3 contains a table (Table I) of sequences of exemplary reagents for converting binary tags into metric tags.

FIGS. 4A-4C illustrate exemplary embodiments of the invention that employ indexing adaptors and padlock probes for generating and enumerating selected probes.

FIG. 8A contains a table (Table II) of lengths of single stranded metric tags released from composite tags produced in Example I.

FIG. 10B shows data from a dilution series of test sequences that demonstrates the sensitivity of the sorting by sequence technique for isolating target sequences from mixtures.

DETAILED DESCRIPTION OF THE INVENTION

Figure 1A:
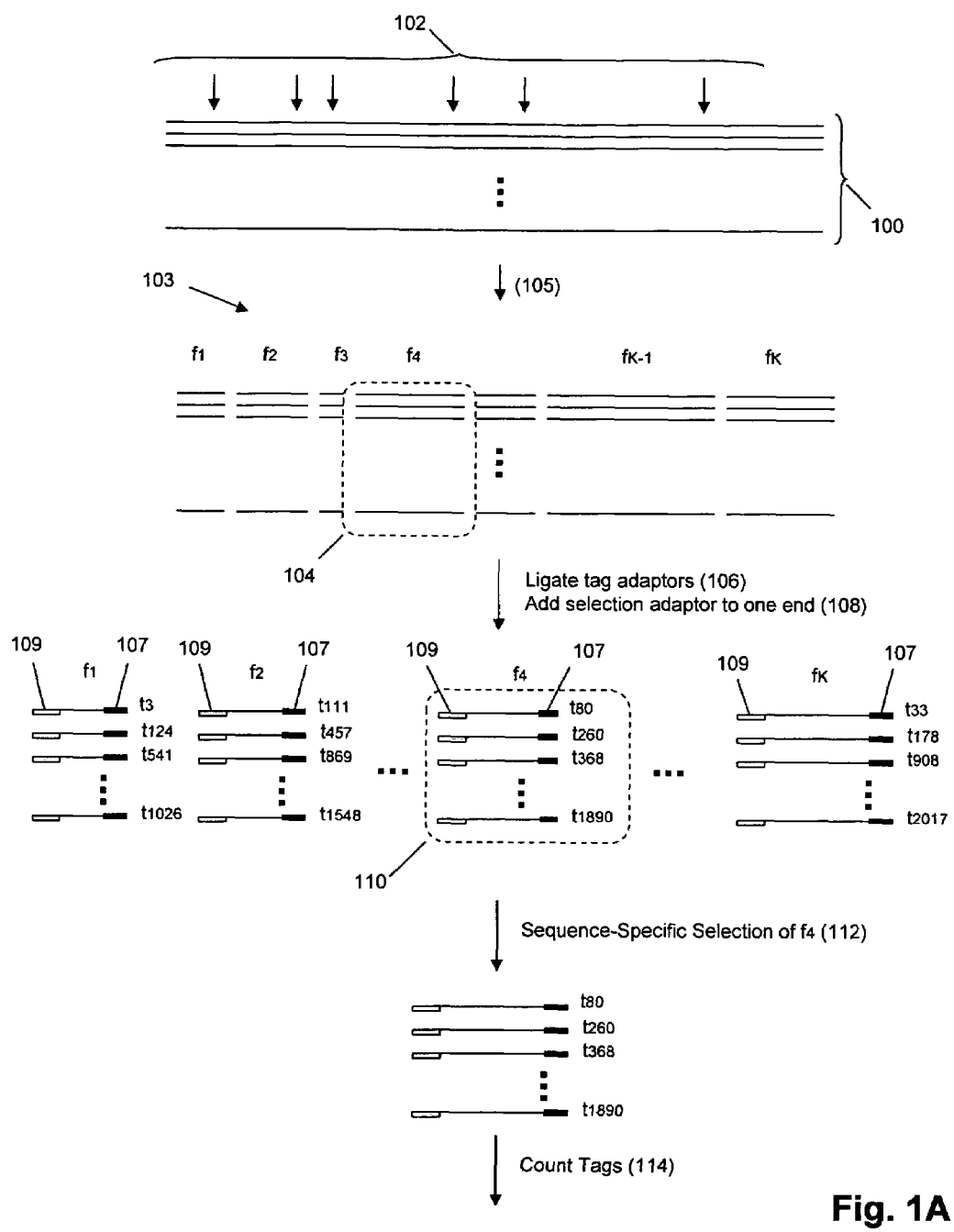
FIGS. 1A-1H illustrate embodiments of the invention for counting polynucleotides, such as restriction fragments.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The invention provides a method of counting molecules that are uniquely labeled with tags. That is, substantially every molecule to be counted in a sample, e.g. the number of single stranded DNA molecules of a particular genetic locus in a sample of genomic DNA, is associated with a probe having a different tag, so that the process of counting multiple copies of the same molecule is transformed into a process of counting the number of different kinds of associated tags. Both the process of associating a unique tag with a selected target molecule and the process of counting associated tags can be carried out in a variety of ways. In one aspect, such associations are made by providing a set of probes that are capable of specifically binding or reacting with the target molecules and that are labeled with tags selected from a repertoire that is substantially larger than the number of target molecules to be counted in a sample. Thus, the type of target molecule capable of being counted in accordance with the invention includes any type molecule for which such probes can be constructed, including, but not limited to, nucleic acids, proteins, peptides, drugs, chromosomes, and other structures, organelles, and compounds for which specific binding compounds, such as antibodies, can be produced. In one aspect, tags for use with the invention are oligonucleotide tags, because they are conveniently synthesized with a diversity of sequences, they are readily incorporated in probes having specific binding capability, and they may be amplified from very small quantities for convenient detection. However, other types of labels may be employed with the invention, which are capable of generating a large diversity of signals, including, but not limited to, quantum dots, nanoparticles, nanobarcodes, and the like, e.g. as disclosed in Freeman et al, Proceedings SPIE, 5705:114-121 (2005); Galitonov et al, Opt. Express, 14:1382 (2006); Reiss et al, J. Electroanal. Chem., 522:95-103 (2002); Freeman et al, Methods Mol. Biol., 303:73-83 (2005); Nicewarner-Pena et al, Science, 294:137-141 (2001); or the like.

When antibodies are available to specifically bind to target molecules to create an association, oligonucleotide tags may be used as labels by forming antibody-oligonucleotide conjugates, e.g. as disclosed in Ullman et al, Proc. Natl. Acad. Sci., 91:5426-5430 (1994); Gullberg et al, Proc. Natl. Acad. Sci., 101:8420-8424 (2004); Sano et al, U.S. Pat. No. 5,665, 539; Eberwine et al, U.S. Pat. No. 5,922,553; which are incorporated by reference. In one embodiment, oligonucleotide tags of specifically bound antibodies may be amplified and detected after washing away unbound conjugates. In another embodiment, a homogeneous format may be employed by using conjugates having a photosensitizer-cleavable linkage, as taught in U.S. patent publication 2006/ 0204999, which is incorporated by reference. After capture of all antibodies, e.g. with protein A or G, the oligonucleotide tags of those specifically bound to target molecules may be released by a photosensitizer attached to a second antibody specific for a second epitope of the target molecule.

Figure 6A:
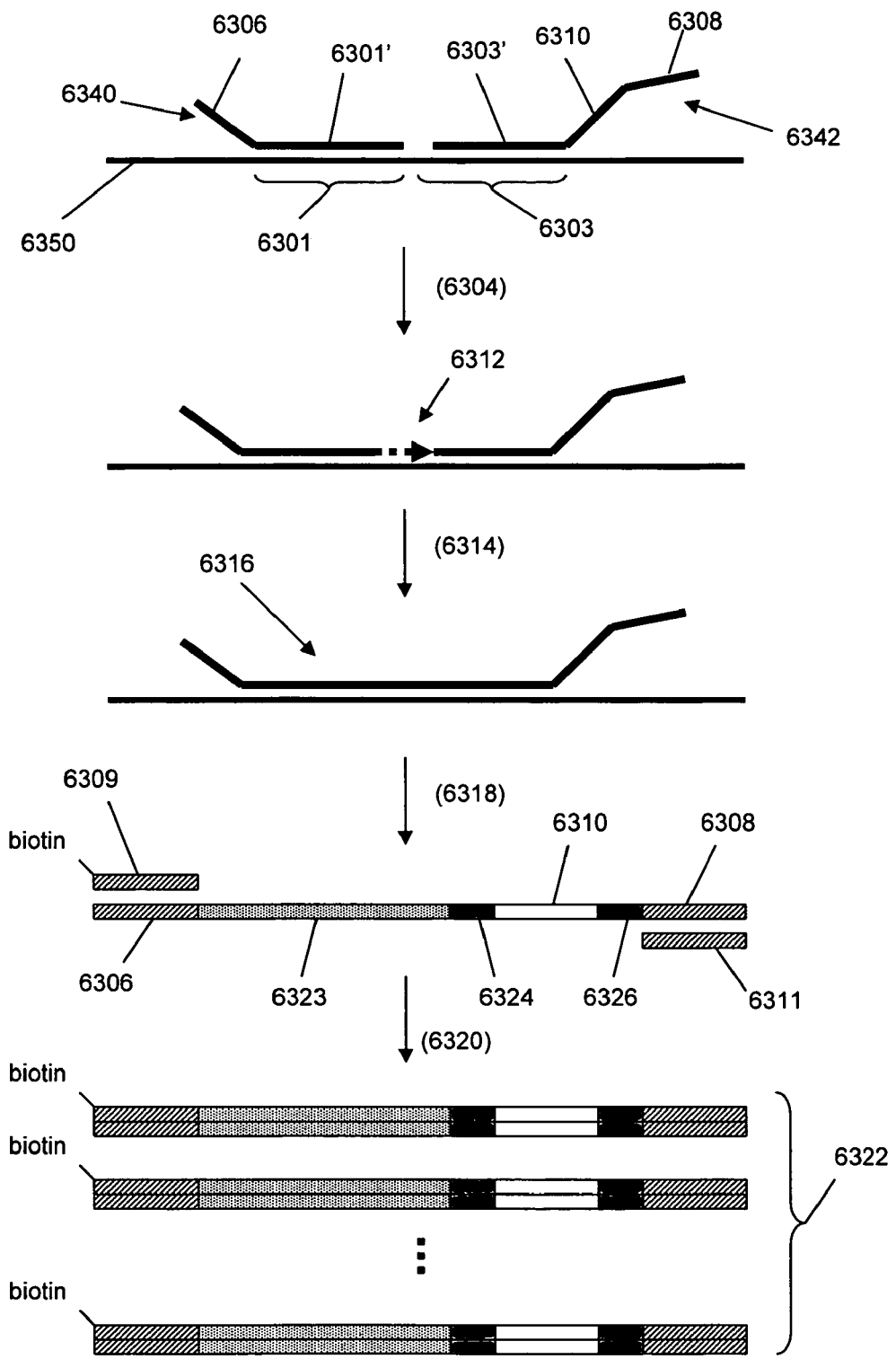
FIGS. 6A-6B illustrate still further exemplary embodiments of the invention that employ ligation probes for generating and enumerating selected probes.

When target molecules are nucleic acids, both specific binding compounds and labels may likewise be nucleic acids. Nucleic acid probes incorporating oligonucleotide tags and components for specifically binding to target nucleic acids may be produced in a variety of forms to permit association with target molecules. In particular, in one aspect of the invention, nucleic acid probes of the invention associate with target nucleic acid by specific hybridization. Such specifically hybridized probes are then altered so that they may be isolated or distinguished from non-specifically hybridized probes. Such alteration and isolation may be carried out in many ways. For example, in one aspect, such alteration is circularization of hybridized probes, e.g. by template-driven ligation, which renders associated probes resistant to exonuclease digestion, as illustrated in FIG. 4C. In another aspect, such alteration is the template-driven ligation of two or more probe components to form a single nuclease-resistance product, as illustrated in FIG. 6A. In another aspect, such alteration is extension by one of more nucleotides to add a capture moiety for physical separation from non-extended probes. In another aspect, after combining 5'-exonuclease-resistant probes with a sample, non-bound probes may be eliminated by digestion with a 3' exonuclease, such as exonuclease III, after which the 3' ends of the bound probes are extended, e.g. with a DNA polymerase, and the resulting complexes are treated with a 5' exonuclease, such as T7 exonuclease, to leave a population of extended probes that may be amplified and detected for enumerating the target molecules.

As mentioned above, once an association between uniquely labeled probes and target molecules has been made, the number of different unique labels can be determined in a number of ways depending on the nature of the label. In the case of labels that comprise oligonucleotide tags, in one aspect, such determinations may be made by sorting to form successively less complex populations or by direct sequencing, as described more fully below.

Counting by Sorting Oligonucleotide Tags

In one aspect, binary tags are used to label molecules and the number of different binary tags present is determined by sequence-specific sorting of the tags. Preferably, unique tags are attached to the molecules to be counted by a process of labeling by sampling, as described by Brenner et al, U.S. Pat. No. 5,846,719. Essentially, any type of molecule, or other structures such as nanoparticles, or the like, that can be labeled with an oligonucleotide tag, can be counted in accordance with the invention. Thus, molecules that can be counted include biomolecules, such as polynucleotides, proteins, antibodies, and so on. In one aspect, polynucleotides are the preferred molecules for counting because of the many ways available to attach oligonucleotide tags, e.g. ligation either as a whole or stepwise in subunits, and to analyze and manipulate tag-polynucleotide conjugate, e.g. amplifying by PCR or other nucleic amplification technology. In one aspect, the method of the invention is implemented by providing separate sets of tags for sorting (i.e. "sorting tags") and for identifying different sorting tags. That is, a set of sorting tags are designed to facilitate the labeling and sorting processes, whereas identification tags are designed for a specific readout device, such as a microarray or electrophoresis instrument. Binary tags are an example of sorting tags, whereas metric tags are an example of identification tags.

Figure 1B:
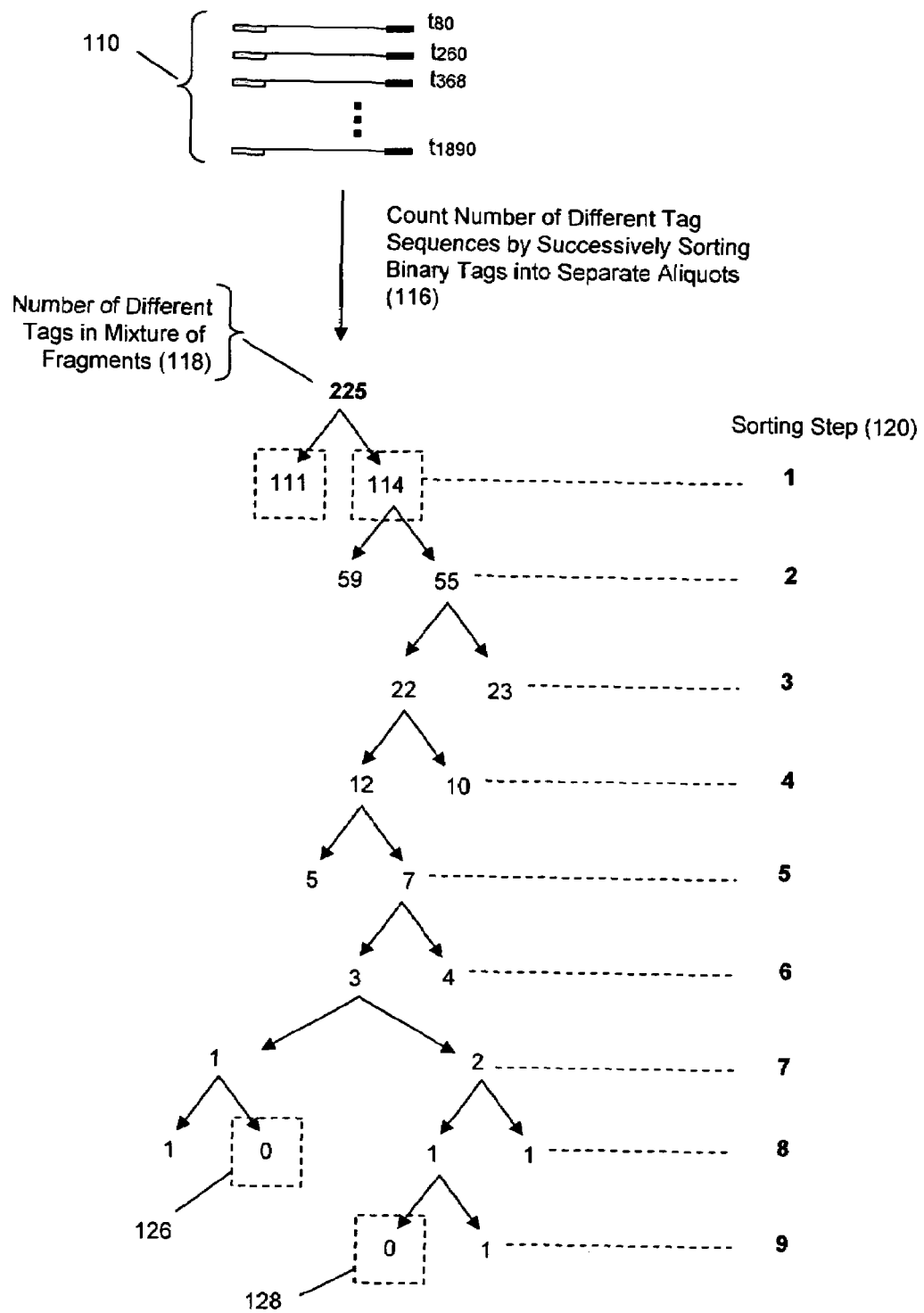
Figure 1C:
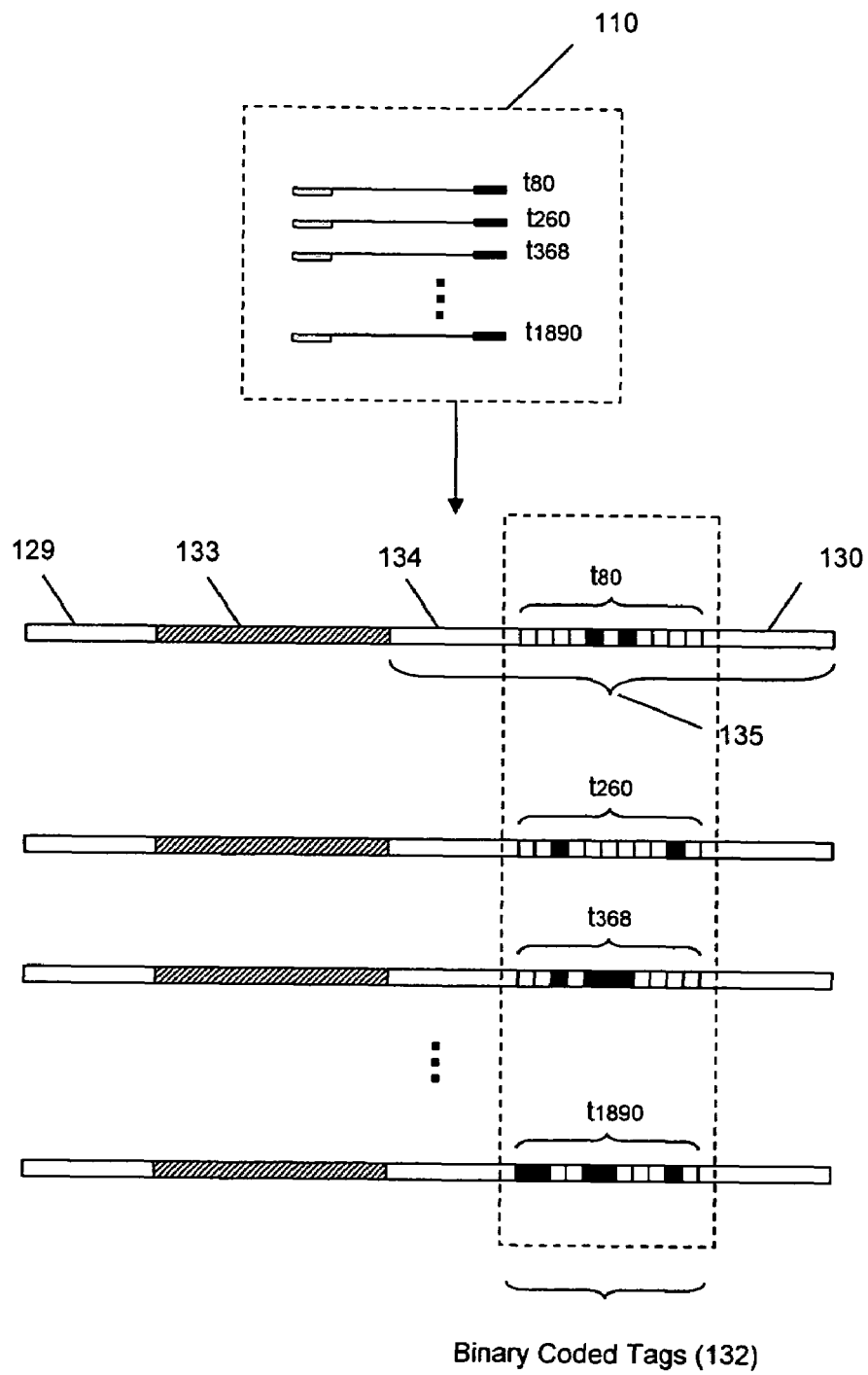

One embodiment of the invention for counting polynucleotides is illustrated in FIGS. 1A-1F. One counting approach is illustrated in FIGS. 1A-1B, where the objective is to count how many restriction fragments of a particular kind are present in a sample, e.g. a sample of genomic DNA from 50-100 cells. DNA (100) extracted from the sample is digested (105) with a restriction endonuclease having recognition sites (102) so that fragments (103) are produced. Preferably, a restriction endonuclease, or a combination of restriction endonucleases, is selected that produces fragments having an expected size in the range of from 100-5000 nucleotide, and more preferably, in the range of from 200-2000 nucleotides. Other fragment size ranges are possible, however, currently available replication and amplification steps work well within the preferred ranges. The object of the method is to count the number of $f_4$ restriction fragments present in DNA (100) (and therefore, the sample of 50-100 cells). After digestion (105), adaptors (107) having complementary ends and containing oligonucleotide tags, i.e. "tag adaptors," are ligated (106) to the fragments. In this example, there are 100-200 fragments of each type, assuming a diploid organism. Each collection of ends of each type of fragment requires 100-200 tag adaptors in the ligation reaction; in effect, each collection of ends samples the population of tag adaptors. In accordance with the invention, the tag adaptors collectively include a population of tags sufficiently large so that such a sample contains substantially all unique tags. In one aspect, the size of the set of tags is at least ten times the number of fragments to be counted; in another aspect, the size of the set of tags is at least 100 times the number of fragments to be counted. After tag adaptors (107) are ligated, one of the tag adaptors on each fragment is exchanged for a selection adaptor (109)(which is the same for all fragments) so that each fragment has only a single tag and so that the molecular machinery necessary for carrying out sequence-specific selection is put in place. (FIG. 1C provides a more detailed illustration of the structure of the fragments at this point). One way to exchange a tag adaptor for a selection adaptor is described below and in FIGS. 2A-2B. After fragments of interest (110) have both adaptors attached, they are sorted from the rest of the fragments by the sequence-specific sorting process described in Appendix I. Briefly, such sorting is accomplished by repeated cycles of primer annealing to the selection adaptor, primer extension to add a biotinylated base only if fragments have a complement identical to that of the desired fragments, removing the biotinylated complexes, and replicating the captured fragments. That is, the selection is based on the sequence of the fragments adjacent to selection adaptor (109). One controls the fragments selected by controlling which incorporated nucleotide has a capture moiety in each cycle. After such sorting, the number of different tags in the population of fragments (110) is determined by successively sorting (116) the binary tags into two separate aliquots. The same sorting procedure of Appendix I is used. In this case, the selection is based on the words, or subunits, of the binary tags in fragments (110). After each sorting step, the resulting aliquots are tested for the presence or absence of fragments. A variety of testing procedures can be used and such selection is a matter of design choice and routine practice. In one aspect, aliquots are assayed using a PCR, which can be implemented with one or more controls or internal standards for confirming the absence of fragments. The sorting process continues until there is an aliquot with no fragments detected. Such a process is outlined in FIG. 1B for an initial number of 225 (118). In each sorting step (120), the number of fragments sorted into each aliquot will usually be about the same, because about the same number of tags will have a word of each type at each position. Of course, statistical flukes are possible, in which case, the counting process may be repeated. In accordance with the invention, not all of the possible branches of a sorting process need be carried out. Selection of a particular pathway is a matter of design choice. For example, in the first sorting step, the 225 fragments are shown to be divided into subsets of 111 (122) and 114 (124). During the sorting process, of course, these quantities are not known. Only the presence or absence of fragments is determined. The numbers in FIG. 1B are presented only for illustration to show how repeated sorting eventually results in an aliquot with no fragments. As also illustrated, the selection of pathway can effect the determination of the number of molecules in the original mixture. However, statistically any preselected pathway should be equivalent. The confidence in a result can be increased by repeating the sorting process or by carrying out sorting along several pathways in parallel. The greatest variability occurs when the number of fragments becomes small, as indicated by examining pathways between sorting step 7 and 9, where one pathway results in no fragments detected (126) at step 8 and another pathway results in no fragments detected (128) at step 9. In this example, the number of molecules in the original mixture can be determined to be in the range between $2^{(8-1)}$ (=128) and $2^{(9-1)}$ (=256). Alternative algorithms may be used within the scope of inventive concept to determine or estimate the number of molecules in the original mixture.

As mentioned above, FIG. 1C provides a structure of fragments having different adaptors at different ends, sometimes referred to herein as "asymmetric" fragments. Exemplary fragments (110) are redrawn to show more structure. The fragments each comprise selection adaptor (129), restriction fragment (133), and tag adaptor (135). Tag adaptor (135) comprises primer binding sites (134) and (130), and sandwich between such sites are binary tags (132). Primer binding site (134) allows amplification of binary tag (132) and selection of binary tag (132) during a sorting procedure. The binary nature of the binary tags are shown by indicating words as open and darkened boxes; that is, there are two choices of word at each position. For tag, $t_{80}$, the binary number for 80 is represented in the pattern of words, which, if an open box is 0 and a darkened box is 1, is simply binary 80 written in reverse order.

Figure 1D:
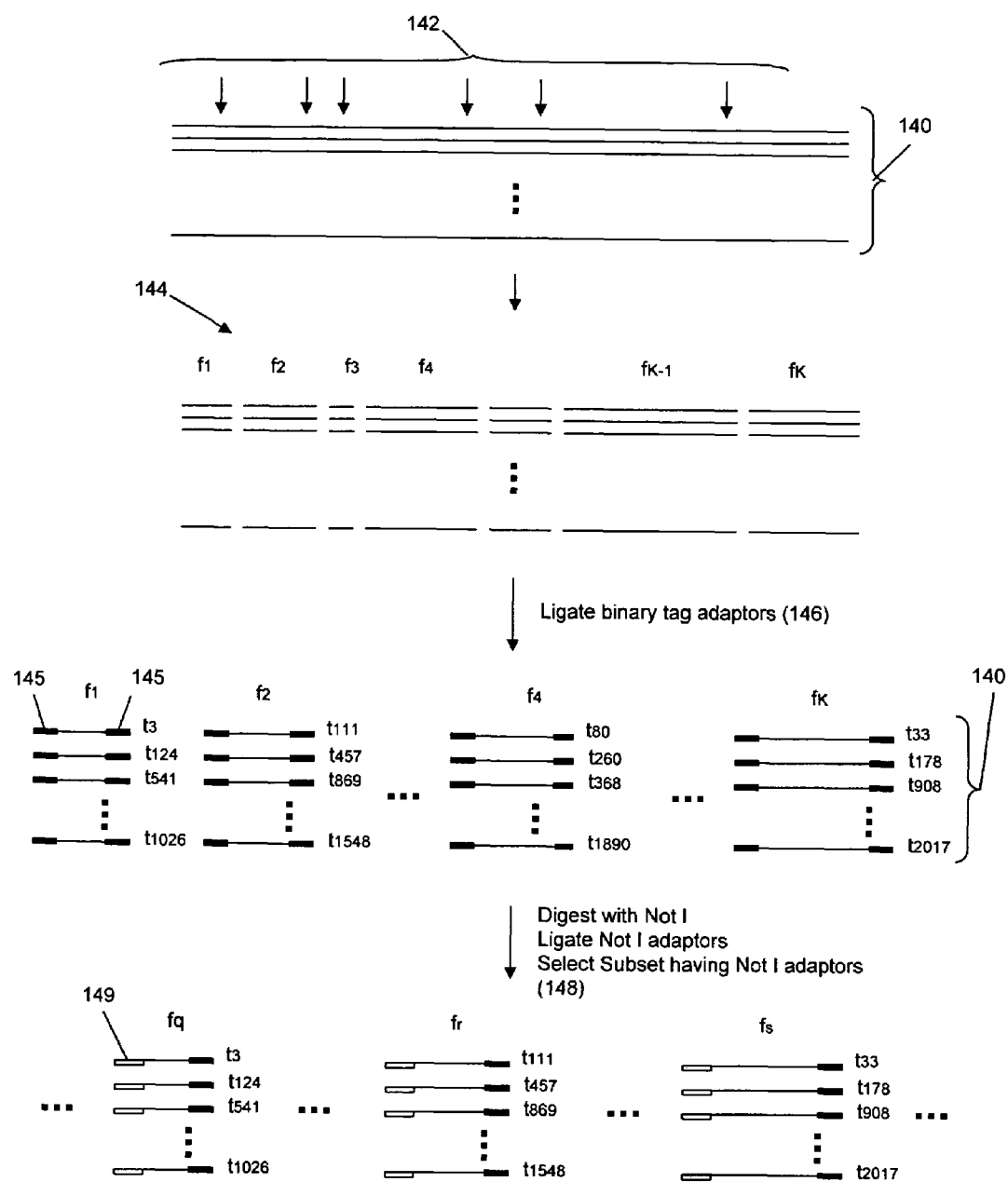
Figure 1E:
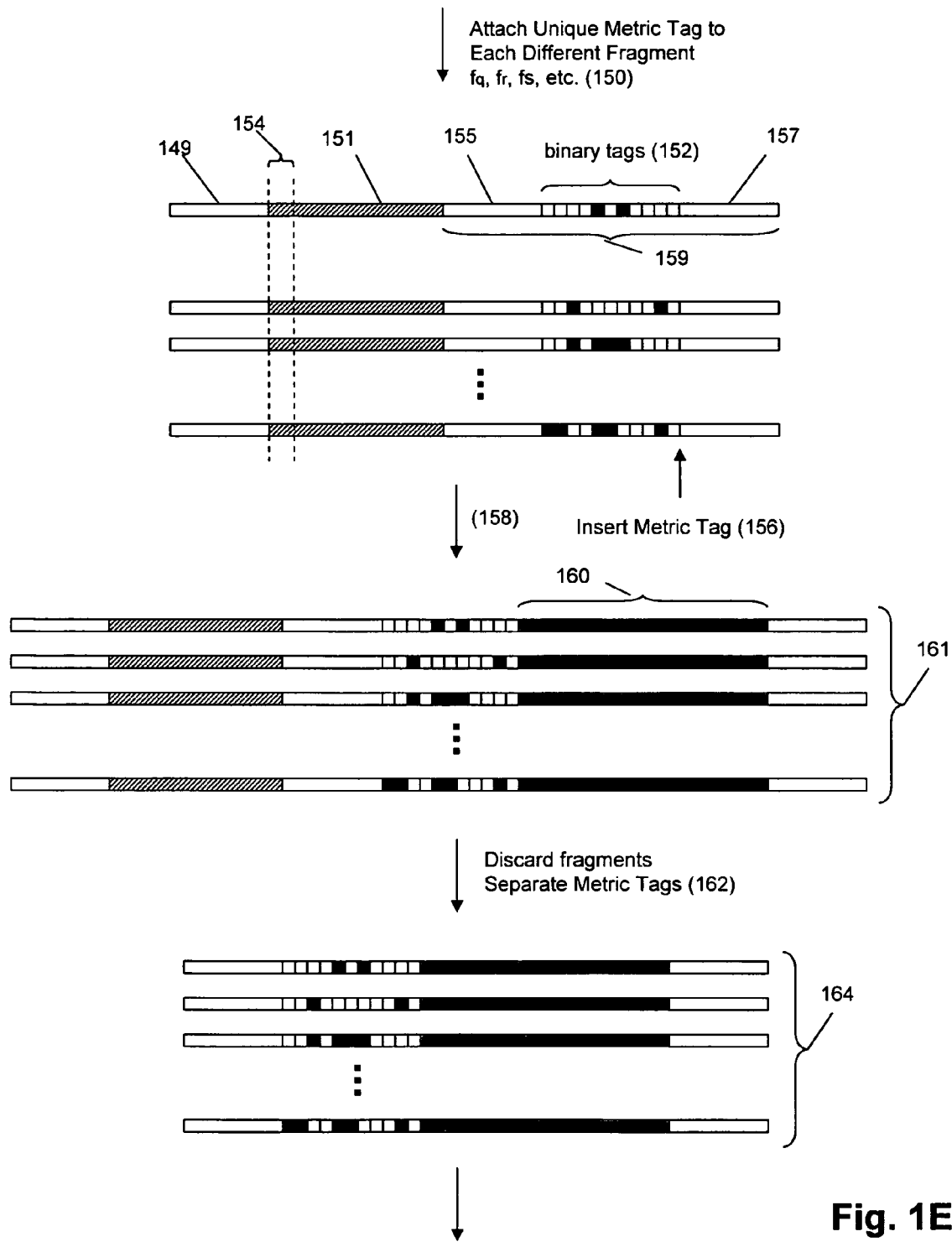
Figure 1F:
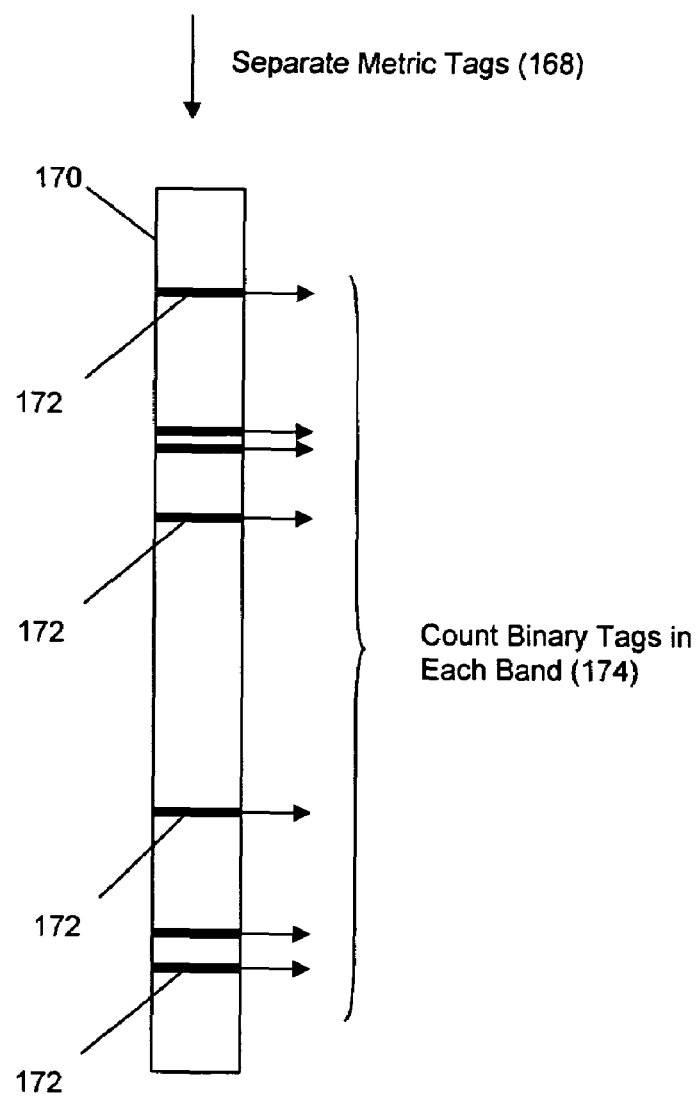

FIGS. 1D-1F illustrate another aspect of the invention where a distribution of fragment copy numbers is determined over an entire genome. Genomic DNA (140) is digested by a restriction endonuclease having recognition sites (142) to produce restriction fragments (144). Preferably, restriction fragments (144) are in the size ranges as described above. In one aspect, as above, genomic DNA (140) is extracted from 50-100 cells, although the starting quantity of DNA is a design choice that depends on factors such as the size of the oligonucleotide tag set available for labeling fragments. Tag adaptors (145) are ligated (146) to fragments (144) to produce population (147) of tag adaptor-fragment conjugates, after which such conjugates are further digested with a "rare cutting" restriction endonuclease. Preferably, for mammalian, or similar-sized genomes, rare cutting restriction endonucleases have recognition sequences that include at least seven specific basepairs. Exemplary rare cutting restriction endonucleases include NotI, AscI, AsiSI, BbvCI, FseI, SbfI, and the like. Selection of such rare cutting restriction endonucleases is a design choice depending on such factors as the number of fragments desired for analysis, the distribution of sites in the genome, the capacity for handling large numbers of fragments, and the like. To the ends created by the above digestion are ligated metric adaptors (149), shown in FIG. 1D for fragments $f_q$, $f_r$, and $f_g$. As illustrated in FIG. 1E, resulting fragments comprise metric adaptor (149), fragment (151), and tag adaptor (159). Tag adaptor (159) comprises primer binding site (155), binary tag (152), and primer binding site (157). Fragments fq, fr, fs, and other such asymmetric fragments are processed as described below to add metric tags at position (156) where the length of the metric tag is encoded by the sequence of fragment (154) adjacent to metric adaptor (149). That is, if the first five nucleotides are used to encode metric tags, then up to $4^5$ (=1024) metric tag can be encoded, which approximately corresponds to the upper limit of the number of fragment that can be separate by a high-throughput DNA sequencer. Alternately, four nucleotides encode 512 metric tags. Attaching metric tags (160) using the process (158) described below results in fragments (161). At this point, fragments (151) and metric adaptor (149) can be discarded (162) when processing the metric tags for separation. From fragments (164) separable metric tags (168) are generated to produce, for example, bands (172) on gel (170), which represent fragments distributed across the genome. The identities of the fragments are known because of the 1-1 correspondence between the sequences of segments (154) of fragments (151) and the lengths of the metric tags. After separation, the fragments are extracted from the gel and the numbers of different binary tags in each is determined as described above. That is, the binary tags are counted in each band to obtain an estimate of fragment copy number in the genomic DNA.

Figure 1G:
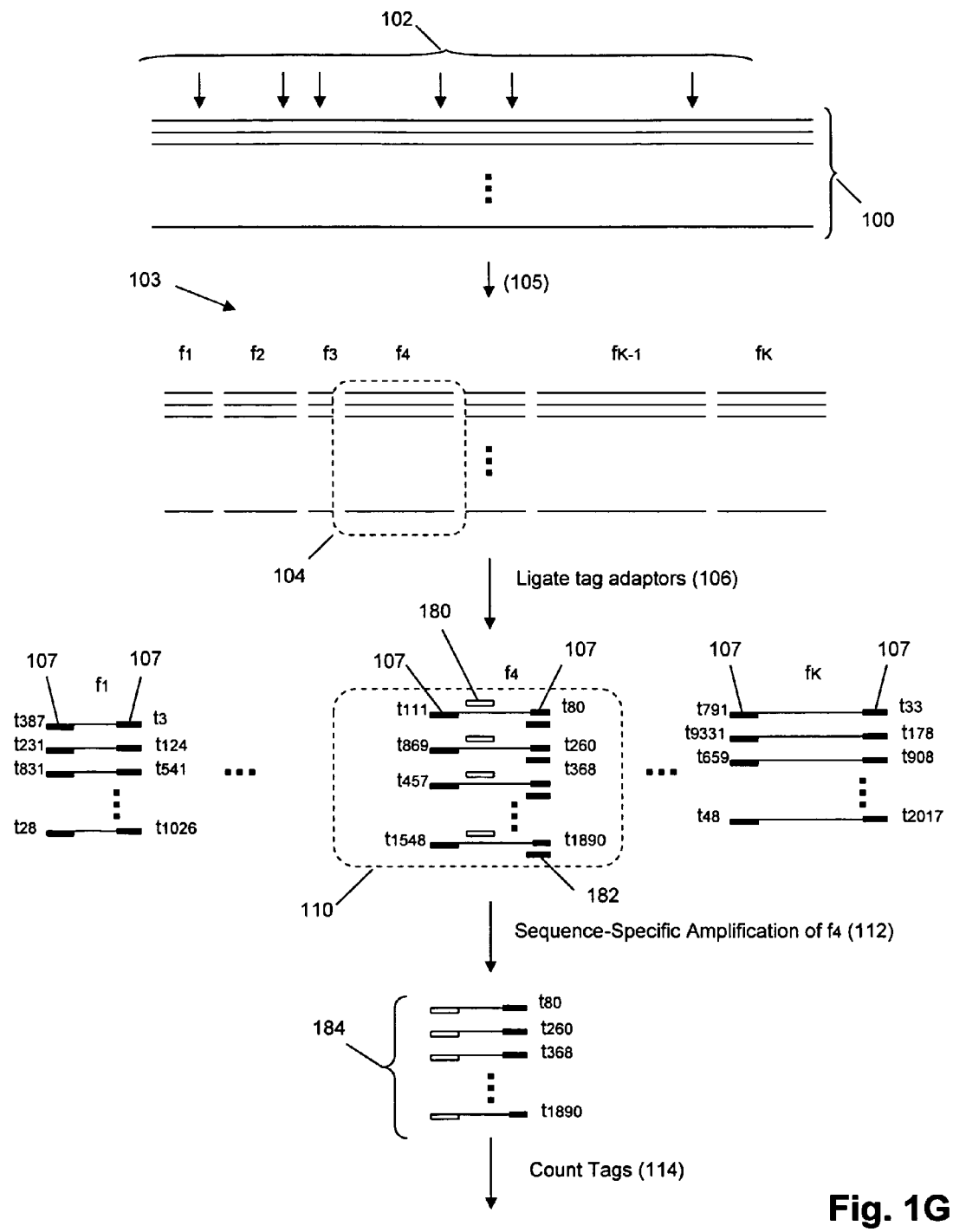
Figure 1H:
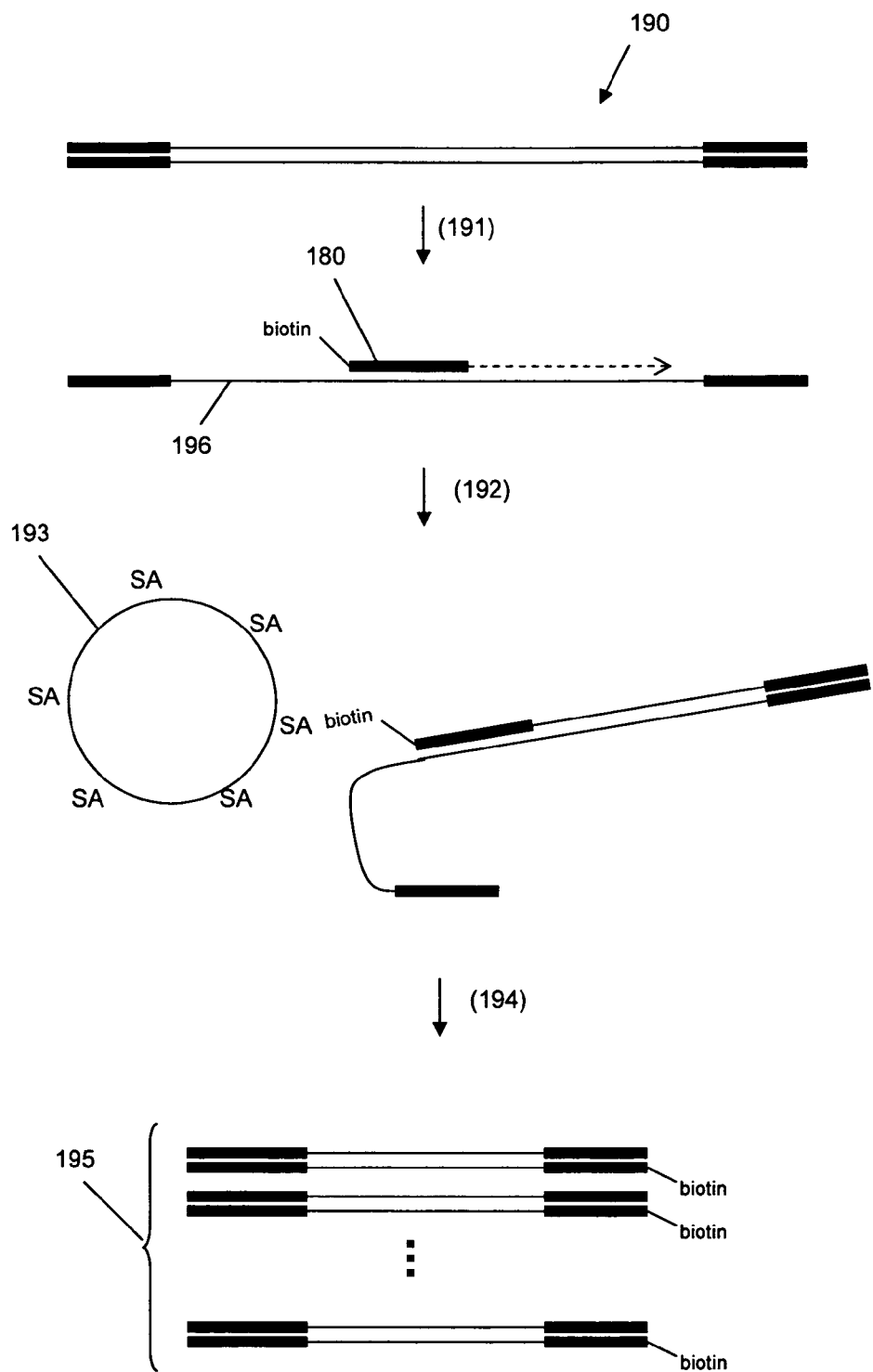

FIG. 1G illustrates a variant of the steps of the above method for attaching oligonucleotide tags to a single end of fragments to be analyzed. The variant may of course be applied more broadly than is illustrated in FIG. 1G. As above, target nucleic acids (100) are digested (105) to produce a population (103) of restriction fragments, of which the number of fragments in the $f_4$ set (104) are to be counted. Adaptors (107) containing oligonucleotide tags are ligated to the ends of all fragments, as illustrated. Thus, each fragment has two adaptors attached, each having a different oligonucleotide tag. The $f_4$ fragments are selected by carrying out a PCR amplification (112) using $f_4$ sequence-specific primer (180) (shown as a forward primer) and reverse primer (182), which is common to all the adaptors. This results in the preferential amplification of fragments (184) that each have a single oligonucleotide tag at one end. These are then counted (112) as described above. In one embodiment, selected fragments, such as $f_4$ fragments, are processed as shown in FIG. 1H. Exemplary $f_4$ fragment (190) is denatured and primer (180), which in this embodiment is biotinylated, is annealed (191) to an interior site of a strand (196) of fragment (190), after which it is extended in a conventional polymerase reaction to the end of strand (196). The resulting complex is captured by a solid support (193) having a complementary capture agent, such as streptavidin (SA). After separation from the other fragments, the duplex region of the captured complex is amplified, e.g. using PCR. Such amplification may be carried out directly from the solid phase support, or the complexes may be released prior to amplification, e.g. using a cleavable biotin linkage, such as a disulfide linkage that may be cleaved with dithiothreitol, or like reagent. The primers used in the latter amplication may contain a capture moiety, such as biotin (as shown) for further manipulation of the fragments.

Exemplary Binary Tags

In one aspect, the invention utilizes sets of dinucleotides to form unique binary tags, which can be synthesized chemically or enzymatically. In regard to chemical synthesis, large sets of tags, binary or otherwise, can be synthesized using microarray technology, e.g. Weiler et al, Anal. Biochem., 243:218-227 (1996); Lipschutz et al, U.S. Pat. No. 6,440,677; Cleary et al, Nature Methods, 1:241-248 (2004), which references are incorporated by reference. In one aspect, dinucleotide "words" can be assembled into a binary tag enzymatically. In one such embodiment, different adaptors are attached to different ends of each polynucleotide from each sample, thereby permitting successive cycles of cleavage and dinucleotide addition at only one end. The method further provides for successive copying and pooling of sets of polynucleotides along with the cleavage and addition steps, so that at the end of the process a single mixture is formed wherein fragments from each sample or source are uniquely labeled with an oligonucleotide tag. Identification of polynucleotides can be accomplished by recoding the oligonucleotide tags of the invention for readout on a variety of platforms, including electrophoretic separation platforms, microarrays, beads, or the like. Below, a readout by electrophoretic separation of length-encoded tags, referred to herein as "metric" tags, is described below.

In one aspect, sets of binary tags for labeling multiple polynucleotides comprise a concatenation of more than one dinucleotide selected from a group, each dinucleotide of the group consisting of two different nucleotides and each dinucleotide having a sequence that differs from that of every other dinucleotide of the group by at least one nucleotide. In another aspect, none of the dinucleotides of such a group are self-complementary. In still another aspect, dinucleotides of such a group are AG, AC, TG, and TC.

Generally, dinucleotide codes for use with the invention comprise any group of dinucleotides wherein each dinucleotide of the group consists of two different nucleotides, such as AC, AG, AT, CA, CG, CT, or the like. In one aspect, dinucleotides of a group have the further property that dinucleotides of a group are not self-complementary. That is, if dinucleotides of a group are represented by the formula 5'-XY, then X and Y do not form Watson-Crick basepairs with one another. That is, preferably, XY does not include AT, TA, CG, or GC. A preferred group of dinucleotides for constructing oligonucleotide tags in accordance with the invention consists of AG, AC, TG, and TC.

The lengths of binary tags constructed from dinucleotides may vary widely depending on the number of molecules to be counted. In one aspect, when the number of molecules is in the range of from 100 to 1000, then the number of binary tags required is about 100 times the numbers in this range, or from $10^4$ to $10^5$. Thus, binary tags comprise from 14 to 17 dinucleotide subunits.

Below, reagents and methods are described for using the dinucleotide codes and resulting oligonucleotide tags of the invention. The particular selections of restriction endonucleases, oligonucleotide lengths, selection of sequences, and particular applications are provided as examples. Selections of alternative embodiments using different restriction endonucleases and other functionally equivalent enzymes, oligonucleotide lengths, and particular sequences are design choices within the purview of the invention.

Reagents for Attaching Dinucleotides to Polynucleotides

In one aspect, the invention employs the following set of four dinucleotides: AG, AC, TG, and TC, allowing genomes to be tagged in groups of four. These are attached to ends of polynucleotides that are restriction fragments generated by digesting target DNAs, such as human genomes, with a restriction endonuclease. Prior to attachment, the restriction fragments are provided with adaptors that permit repeated cycles of dinucleotide attachment to only one of the two ends of each fragment. This is accomplished by selectively protecting the restriction fragments and adaptors from digestion in the dinucleotide attachment process by incorporating 5-methylcytosines into one strand of each of the fragment and/or adaptors. In this example, Sfa NI, which cannot cleave when its recognition site is methylated and which leaves a 4-base overhang, is employed in the adaptors for attaching dinucleotides. A similar enzyme that left a 2-base overhang could also be used, the set of reagents illustrated below being suitably modified.

Reagents for attaching dinucleotides are produced by first synthesizing the following set of two-dinucleotide structures (SEQ ID NO: 1):

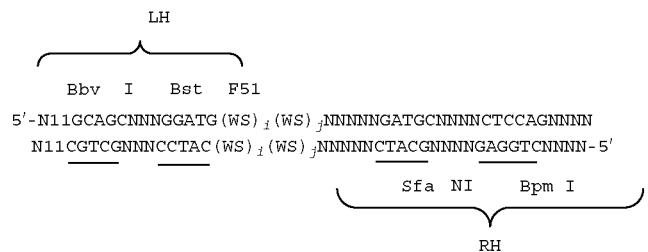

where N is A, C, G, or T, or the complement thereof, (WS)$_i$ and (WS)$_j$ are dinucleotides, and the underlined segments are recognition sites of the indicated restriction endonucleases. "LH" and "RH" refer to the left hand side and right hand side of the reagent, respectively. In this embodiment, sixteen structures containing the following sixteen different pairs of dinucleotides are produced:

| AGAG | ACAG | TGAG | TCAG |
|------|------|------|------|
| AGAC | ACAC | TGAC | TCAC |
| AGTG | ACTG | TGTG | TCTG |
| AGTC | ACTC | TGTC | TCTC |

Four mixtures of the above structures are created whose dinucleotide pairs can be represented as follows:

[WS]AG

[WS]AC

[WS]TG

[WS]TC where [WS] is AG, AC, TG, or TC. Two PCRs are carried out on each of the sixteen structures, one with the left hand primer biotinylated, L, and one with the right hand primer biotinylated, R. Pool L amplicons to form the mixtures above, digest L amplicons with BstF5I, and remove the LH end as well as any uncut sequences or unused primers to give mixtures containing the following structures (SEQ ID NO: 2, SEQ ID NO: 3, SEQ ID NO: 4 and SEQ ID NO: 5):

```
   AGNNNNNGATGCNNNNCTCCAGNNNN          (I)
(WS) TCNNNNNCTACGNNNNGAGGTCNNNN

ACNNNNNGATGCNNNNCTCCAGNNNN          (II)
(WS) TGNNNNNCTACGNNNNGAGGTCNNNN
```

-continued

```
   TGNNNNNGATGCNNNNCTCCAGNNNN         (III)
(WS) ACNNNNNCTACGNNNNGAGGTCNNNN

TCNNNNNGATGCNNNNCTCCAGNNNN          (IV)
(WS) AGNNNNNCTACGNNNNGAGGTCNNNN
``` where WS is AG, AC, TG, or TC. For R amplicons, after PCR, pool all, cut with Bpm I, and remove the right hand end to give a mixture of the following structures (SEQ ID NO: 6):

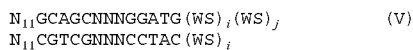

where (WS)$_i$ and (WS)$_j$ are each AG, AC, TG, or TC. Mixture (V) is separately ligated to each of mixtures (I)-(IV) to give the four basic reagents for adding dinucleotides to polynucleotides. These tagging reagents can be amplified using a biotinylated LH primer, cut with Bbv I, and the left hand primer and removed to provide four pools with the structures:

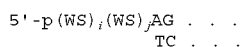

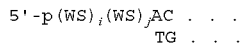

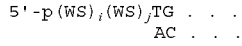

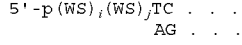

where (WS)$_i$ and (WS)$_j$ are as described above, and p is a phosphate group.

Attaching Oligonucleotide Tags to Polynucleotides

Figure 2A:
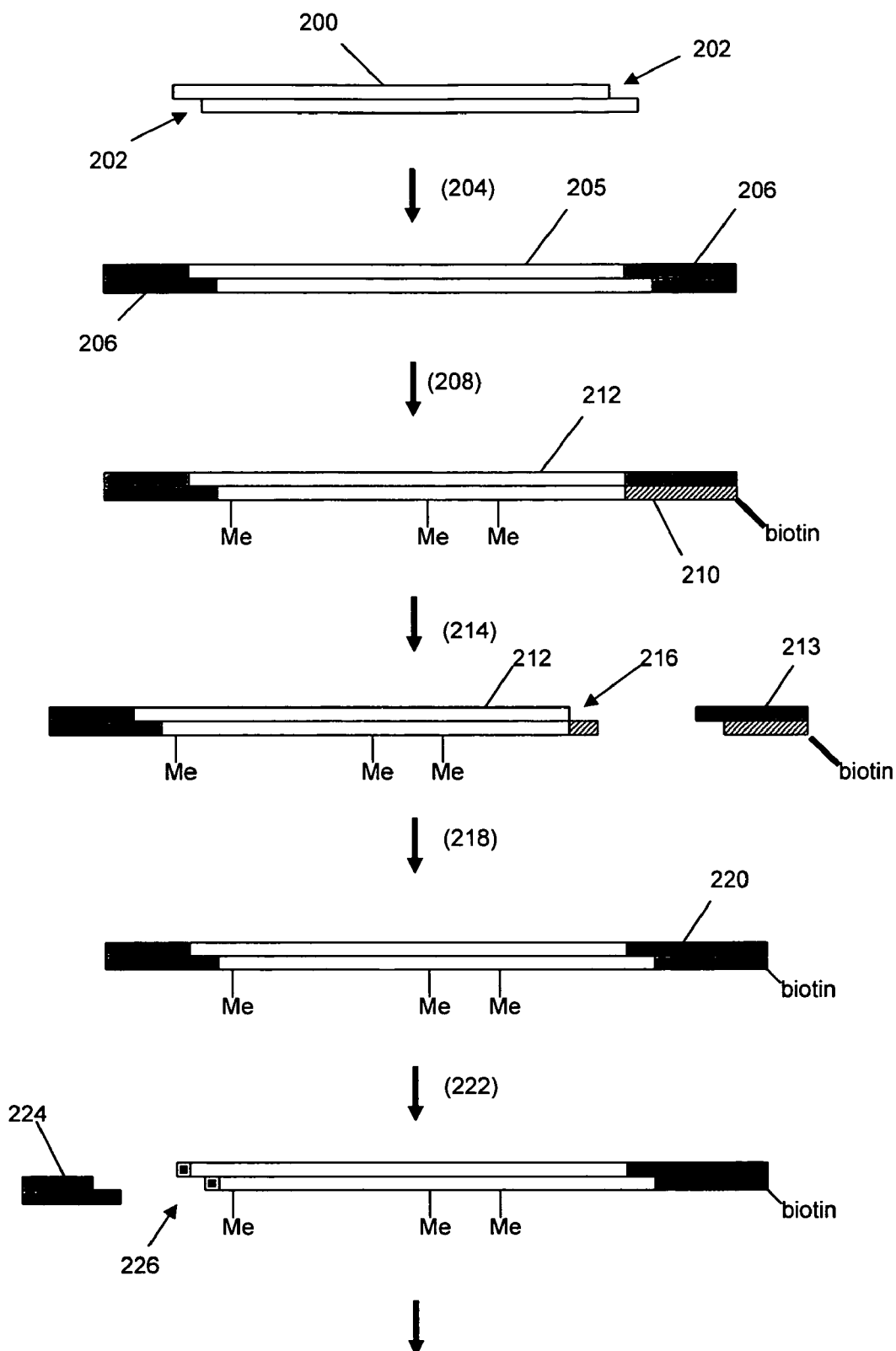
FIGS. 2A-2B illustrate a general procedure for attaching an oligonucleotide tag to one end of a polynucleotide.
Figure 2B:
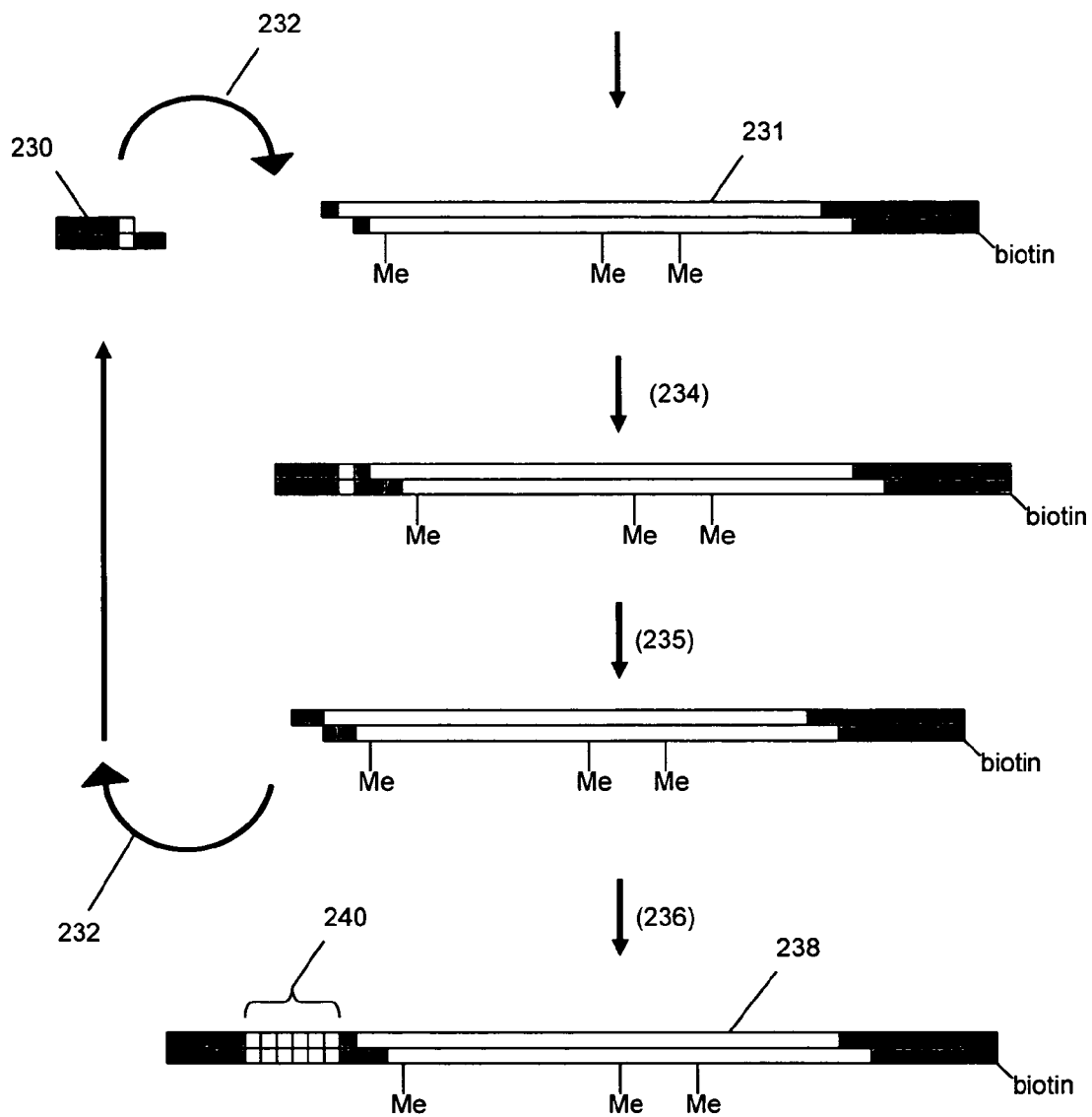

A general procedure for attaching oligonucleotide tags to polynucleotides is illustrated in FIGS. 2A-2B. Polynucleotides (200) are generated that have overhanging ends (202), for example, by digesting a sample, such as genomic DNA, cDNA, or the like, with a restriction endonuclease. Preferably, a restriction endonuclease is used that leaves a four-base 5' overhang that can be filled-in by one nucleotide to render the fragments incapable of self-ligation. For example, digestion with Bgl II followed by an extension with a DNA polymerase in the presence of dGTP produces such ends. Next, to such fragments, initial adaptors (206) are ligated (204). Initial adaptors (206) (i) attach a first segment, or word, of an oligonucleotide tag to both ends of each fragment (200). Initial adaptors (206) also contain a recognition site for a type IIs restriction endonuclease that preferably leaves a 5' four base overhang and that is positioned so that its cleavage site corresponds to the position of the newly added segment. (Such cleavage allows segments to be added one-by-one by use of a set of adaptor mixtures containing pairs of segments, or words). In one aspect, initial adaptor (206) is separately ligated to fragments (200) from each different sample, e.g. each different individual genome within a population.

In order to carry out enzymatic operations at only one end of adaptored fragments (205), one of the two ends of each fragment is protected by methylation and operations are carried out with enzymes sensitive to 5-methyldeoxycytidine in their recognition sites. Adaptored fragments (205) are melted (208) after which primer (210) is annealed as shown and extended by a DNA polymerase in the presence of 5-methyldeoxycytidine triphosphate and the other dNTPs to give hemi-methylated polynucleotide (212). Preferably, primer (210) has a capture moiety attached, such as biotin, or the like. Polynucleotides (212) are then digested with a restriction endonuclease that is blocked by a methylated recognition site, e.g. Dpn II (which cleaves at a recognition site internal to the Bgl II site and leaves the same overhang). Accordingly, such restriction endonucleases must have a deoxycytidine in its recognition sequence and leave an overhanging end to facilitate the subsequent ligation of adaptors. Digestion leaves fragment (212) with overhang (216) at only one end and free biotinylated fragments (213). After removal (218) of biotinylated fragments (213) (for example by affinity capture with avidinated beads), adaptor (220) may be ligated to fragment (212) in order to introduce sequence elements, such as primer binding sites, for an analytical operation, such as sequencing, SNP detection, or the like. Such adaptor is conveniently labeled with a capture moiety, such as biotin, for capture onto a solid phase support so that repeated cycles of ligation, cleavage, and washing can be implemented for attaching segments of the oligonucleotide tags. After ligation of adaptor (220), a portion of initial adaptor (224) is cleaved so that overhang (226) is created that includes all (or substantially all) of the segment added by adaptor (206). After washing to remove fragment (224), a plurality of cycles (232) are carried out in which adaptors (230) containing pairs of segments, or words, are successively ligated (234) to fragment (231) and cleaved (235) to leave an additional segment, or word. Such cycles are continued until the oligonucleotide tags (240) are complete, after which the tagged polynucleotides may be subjected to analysis directly, or single strands thereof may be melted from the solid phase support for analysis.

Counting Binary Tags

Fragment-binary tag conjugates can be counted in a number of ways. For example, in one aspect, in a reversal of the tagging process, a restriction enzyme can be used that cuts two or four bases into the binary tag, followed by ligation of adaptors with suitable capture moieties to remove four or sixteen sets of fragments, respectively. In another aspect, binary tags of conjugates can be counted by first translating them into metric tags, as described below, after which the metric tags are separated for identification. In still another aspect, tag sequences can be sorted from a mixture using the sorting-by-sequence technique disclosed in Brenner, PCT publication WO 2005/080604, which is incorporated herein by reference. In this case, deoxynucleotides with ligands that can be easily detached, enabling the extension of the primer at the same time.

Formally to sort A and T, nucleotides for A and T with capture moieties (or ligands) attached are used. Thus, deoxyA carrying a biotin with a disulfide bond in the linker and deoxyT with another detachable ligand. The same applies to G and C. However, the following can also be carried out: For separating A and T, a ligand-substituted T can be used. After incorporation, these are removed and the templates then released by cleaving the disulfide bond by reduction. To the residual solution are added deoxyA and dideoxyT to cap any unsorted sites. This sorting is carried out on single stranded DNA, but the addition of sequences requires double stranded templates. Since in the above process information is transferred from one end of a molecule to the other end, a double stranded sequence must exist at the other end. This is readily accomplished by primer annealing and extension.

In a preferred embodiment, described more fully below, binary tags (or like tags) and metric tags are both attached to probes for particular biomolecules to form a labeled probe of the following structure:

| Binary Tag | Metric Tag | Probe |
| --- | --- | --- |

The probe may be any binding compound specific for biomolecule; however, as described below, in one aspect, the probe is an oligonucleotide complementary to a target polynucleotide of interest, such as a segment of genomic DNA, an RNA gene product, or the like. The binary tag component may take on any one of a very large number of species, as described above; for example, it may be a binary tag of any one of $2^{16}$ ($\approx$65,000) different sequences. The number of different metric tags is selected based on ease of synthesis and the type of separation system employed; thus, typically the number of different metric tags is much lower than that of binary tags. For convenient synthesis and separation by electrophoresis using commercially available instruments, a number of different metric tags in the range of from 50-100 may be employed, e.g. 64. As described above, such labeled probes are combined with a sample containing target polynucleotides, e.g. a fetal DNA sample, such that substantially all target polynucleotides in the sample, e.g. chromosome 21 sequences at a selected locus, bind to labeled probes. Thus, if there are 300 copies of chromosome 21, then 300 probes are bound. Such bound probes are selected so that 300 different binary tags are isolated. Since the number of metric tags is significantly lower than that of the binary tags, substantially every metric tag in the isolated probes will have a unique binary tag (as will each probe bound to a target polynucleotide). After labeled probes bound to target polynucleotides are selected, their corresponding binary tags may be counted by successive operations of "sorting by sequence" to reduce the complexity of the mixture, followed by a final readout of binary tag numbers in the reduced-complexity mixtures by separation and counting of the metric tags.

Translating Fragment Sequence or Binary Tags into Metric Tags

In this example, binary tags of 512 fragments are recoded as metric tags that can be readout by electrophoretic separation. The same procedure is used to recode ordinary sequence into metric tags, making obvious and routine changes to the reagents described below. The following reagents ($S_0$ and $T_0$ through $T_7$, which are SEQ ID NOS: 7 through 16, respectively) are synthesized using conventional methods:

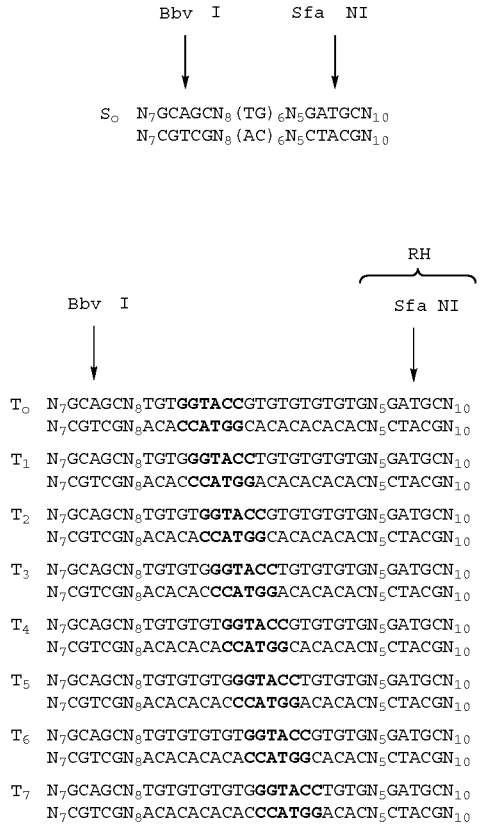

where the bolded letters indicate the position of a Kpn I site. The upper stands of the above sequences are also shown in the table of FIG. 3 with exemplary express sequences inserted for the N's shown above. From these components, $S_o$ can be concatenated to give different lengths of insert in multiples of eight bases in accordance with the formula: $S_i=nS_o$ with biotinylated left hand primer and separately with biotinylated right hand primer. The above are processed by cutting with Bbv I and removing the left end to leave (SEQ ID NO: 16):

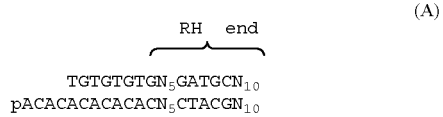

Separately cut RH end with Sfa NI and remove the right end to leave (SEQ ID NO: 17):

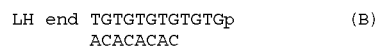

(A) and (B) are ligated and amplified by PCR to provide a reagent, $S_2$, for adding 16 bases. $S_3$ is made by the same method from $S_1$ and $S_2$, and $S_4$ from $S_2$ and $S_2$. Likewise, $S_5$ through $S_8$ are constructed by similar combinations as follows.

| Concatenate | Resulting Reagent | Bases Added By Concatenate |
|---|---|---|
| S1 + S2 | S3 | 24 |
| S2 + S2 | S4 | 32 |
| S1 + S4 | S5 | 40 |
| S2 + S4 | S6 | 48 |
| S3 + S4 | S7 | 56 |
| S4 + S4 | S8 | 64 |

Call the last reagent a "block" or S8=B1. Using the same methods, B2 to B7 are constructed for adding bases in multiples of 64.

Recall that the final tagged library has the following structure (SEQ ID NO: 18):

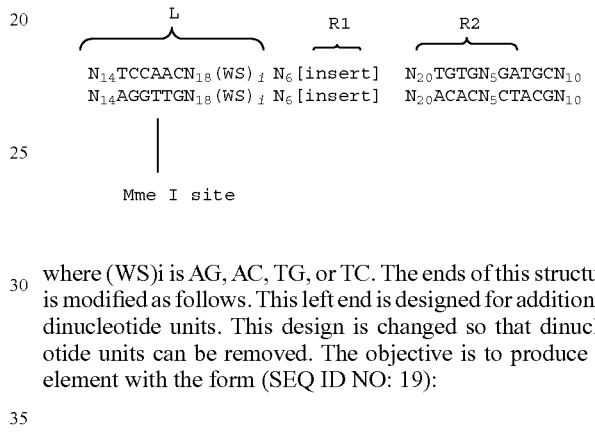

where (WS)i is AG, AC, TG, or TC. The ends of this structure is modified as follows. This left end is designed for addition of dinucleotide units. This design is changed so that dinucleotide units can be removed. The objective is to produce an element with the form (SEQ ID NO: 19):

$$N_{14}N_3(WS)_iN_2 \ldots$$
$$N_{14}N_3(WS)_iN_2 \ldots$$

It could be substituted now or it could be used in the last tagging set of adaptors.

Single strands for sorting are obtained and at the same time the methylated Sfa NI site on the right is unblocked. Using an R2 primer the denatured DNA is copied once to displace the old bottom strand, which is destroyed by addition of exonuclease I. After heat deactivation of the enzyme, more primer is added and the amplification is repeated several times, e.g. 8 times. The sorting proceeds by alternative extension with dGTP or dCTP and with dTTP or dATP. The resulting strands are hybridized to a biotinylated L primer and moved to a new solution. All these are one-tube reactions. The top strand is now primed with R1 and extended to make the right end double stranded. Strands can now be sorted from the left end. Using the dideoxy method, successively synthesized primers are used to perform the first sort. Thus, if the first sort is G v C, then two primers, one extended by G and the other by C are required for the sort. The next step, sorting again for G v C, requires four primers, the original, $p_o$, extended by GA, GT, CA, CT. Any further sorting would require the synthesis of additional primers. In the case considered here, the binary code is used twice, and so the alternative, remove 3 bases and start again, cannot be used. Here it is essential to use the process of detaching the ligand, so that the primer is extended at the same time as sorting. Another possibility is to synthesize the primer in steps, after separation and release.

Recoding is implemented as follows. Remove the right end of the above by cutting with Sfa NI. Sort into eight batches. A binary number can be assigned to these, on the convention that A=0; T=1, and G=0, C=1 (i.e. R=0, Y=1). In ascending numerical order, ligate as follows: 000, no addition, 001 B1 (that is, 1 block 64 bases), 010 B2, and so on up to 111, B7 pool, cut right end and sort into next 8 classes. Using same numbering rule, add to 000 nothing, to 001, S1, which adds 8 bases, to 010, S2 to add 16 bases and so on until 111 receives S7, which adds 56 bases. Again, after ligation, pool and cut. Now again sort a further 3 steps into eight batches. Again, these are labeled 000 to 111, and now these are added to as follows: 000, T0, 001, T1, and so on until 111 receives T7. Sequences have now been added that will give eight separate bands upon electrophoretic separation, stepped by one nucleotide, when the tags are processed. The process is completed as follows. Although each genome is in a one-to-one correspondence with a single length of an oligonucleotide (i.e. a metric tag), the physical lengths of the metric tags are not the same and since it is desirable to be able to PCR the tags, preferably the metric tags should be the same length. Thus, appropriate length of oligonucleotide are added to each to make them all the same. Remove the primers, make all of the DNA. double stranded (amplify if necessary), make it single stranded at the left end (as before), and double stranded at the right. Sort into 8 batches for block addition, number from 000 to 111. Add blocks but in reverse order: to 000 add B7, 001 B6 and so on until 111 receives nothing. Pool, cut again at right end, sort into 8 batches, number from 000 to 111 and add Sn, n=1, 2 ... 7, in reverse order, such that 000 receives S7, 001 S6, and so on until 111 receives nothing. Pool again, cut and add an appropriate final end required for subsequent steps. Note although there is not a symmetrical disposition of blocks and steps, we have BS-sequence-BS, it does not matter because now every tag now has the same length.

Counting by Directly Sequencing Samples of Oligonucleotide Tags

In one aspect, oligonucleotide tags are excised from selected probes and identified by sequencing. In one embodiment, such sequencing takes place after excised tags are concatenated and cloned into a conventional sequencing vector, in a manner similar to that used in the SAGE technique, e.g. U.S. Pat. Nos. 6,746,845; 6,383,743; 5,866,330; 5,695,937; 6,498,013; U.S. patent publications 2003/0186251; 2004/0219580; 2004/0090892; Powell, Nucleic Acids Research, 26: 3445-3446 (1998); which references are incorporated by reference. In another embodiment, such tags are sequenced without concatenation using a short-read length high-throughput sequencing method, such as described by Margulies et al (2005), Nature, 437:376-380; Berka et al, U.S. patent publication 2005/0079510; Shimkets et al, International patent publication WO 2005/039389; Shendure et al (2005), Science, 309:1728-1739; Church et al, International patent publication WO 2005/082098; or the like. In this latter approach, oligonucleotide tags may be amplified using emulsion PCR, e.g. as also disclosed in the cited references, so that clonal populations of each oligonucleotide tag of a sample are formed on beads, which are then sequenced.

An important feature of the invention is providing target molecules, such as polynucleotides, with unique oligonucleotide tags by the process of labeling by sampling, as disclosed by Brenner et al, U.S. Pat. No. 5,846,719, which is incorporated by reference. For example, polynucleotides of a population to be labeled are each associated or linked, e.g. by ligation, to an oligonucleotide tag from a population that has a much larger size than that of the target polynucleotide population. In one aspect, the size of the population of oligonucleotide tags is at least ten times the size of the population of target polynucleotides to be labeled. In another aspect, the size of the population of oligonucleotide tags is at least 100 times the size of the population of polynucleotides to be labeled. Generally, a size of tag population is selected that ensures with high probability that substantially every target polynucleotide will have a unique tag. In one aspect, such probability is at least 90 percent; in another aspect, such probability is at least 95 percent; and in another aspect, such probability is at least 99 percent. In one aspect, the method of the invention is employed to determine numbers of target polynucleotides in small biological or patient samples, such as samples containing 10 to 1000 cells of interest. Whenever such samples are taken from diploid cells, such as mammalian cells, then the size of the tag population is preferably in the range of from 200 to at least 20,000 in one embodiment, and in the range of from 2000 to at least 200,000 in another embodiment.

If the number of molecules to be counted are greater than about ten percent of the population of oligonucleotide tags, then the likelihood that different molecules will have the same tag increases. Consequently, the molecule will be under counted when the tags are analyzed.

Target polynucleotides can be any type of polynucleotide so long as it has the capability to be associated with, or linked to, an oligonucleotide tag to produce a selected probe, that is, a structure resistant to degradation by at least one nuclease activity or that can be isolated from probes that do not specifically interact or associate with a target polynucleotide. In particular, target polynucleotide can be either single stranded DNA or double stranded DNA. In one aspect, target polynucleotides are restriction fragments produced by digesting a cDNA library or genomic DNA with one or more type IIs restriction endonucleases. In another aspect, target polynucleotides are single stranded DNAs, such as produced by denaturing genomic DNA, cDNA, or like polynucleotides. Target polynucleotide may be produced from such source DNA by shearing or by cleavage with one or more nucleases. In one aspect of the invention, an oligonucleotide tag is linked to a target polynucleotide by ligation. In particular, one or more adaptors can be ligated to target polynucleotides to form structures resistant to nuclease digestion. For example, when target polynucleotides are type IIs restriction fragments having particular unique sequence overhangs, complementary adaptors can be provided for each end. Such adaptors can have nuclease resistant linkages or they can be in the form of hairpins, e.g. as described by Kim et al, Biochem. Biophys. Res. Comm., 336:168-174 (2005), both forms of which confer resistance to single stranded exonucleases, such as exonuclease I, exonuclease III, and the like. In another embodiment, a single adaptor is provided for each kind of target polynucleotide that has two complementary ends so that upon ligation a double stranded DNA circle is formed having resistance to one or more nucleases, such as single stranded nucleases, exonucleases, and the like, for example, as described in Callow et al, U.S. patent publication, 2005/0019776, which is incorporated by reference. In another aspect of the invention, selected probes are padlock probes that are circularized by a template-driven ligation reaction wherein a target polynucleotide is employed as a template, such as described in Macevicz, PCT publication WO 2005/111242. Construction and use of padlock probes are disclosed in the following references that are incorporated by reference: Aono et al, Japanese patent publication JP 4-262799; Nilsson et al, Science, 265:2085-2088 (1994); U.S. Pat. Nos. 5,871, 921; 5,866,337; Zhang et al, Gene, 211:277-285 (1998); Lizardi et al, Nature Genetics, 19:225-232 (1998); Hardenbol et al, Nature Biotechnology, 21:673-678 (2003), and the like. In still another aspect of the invention, selected probes can be formed by the ligation of two separate polynucleotides that form perfectly matched duplexes at adjacent locations on a target polynucleotide, such as disclosed by Fan et al, Cold Spring Harbor Symposia on Quantitative Biology, Vol.

LXVIII, pages 69-78 (2003); Schouten, U.S. Pat. No. 6,955, 901; and the like, which are incorporated by reference.

Figure 4B:
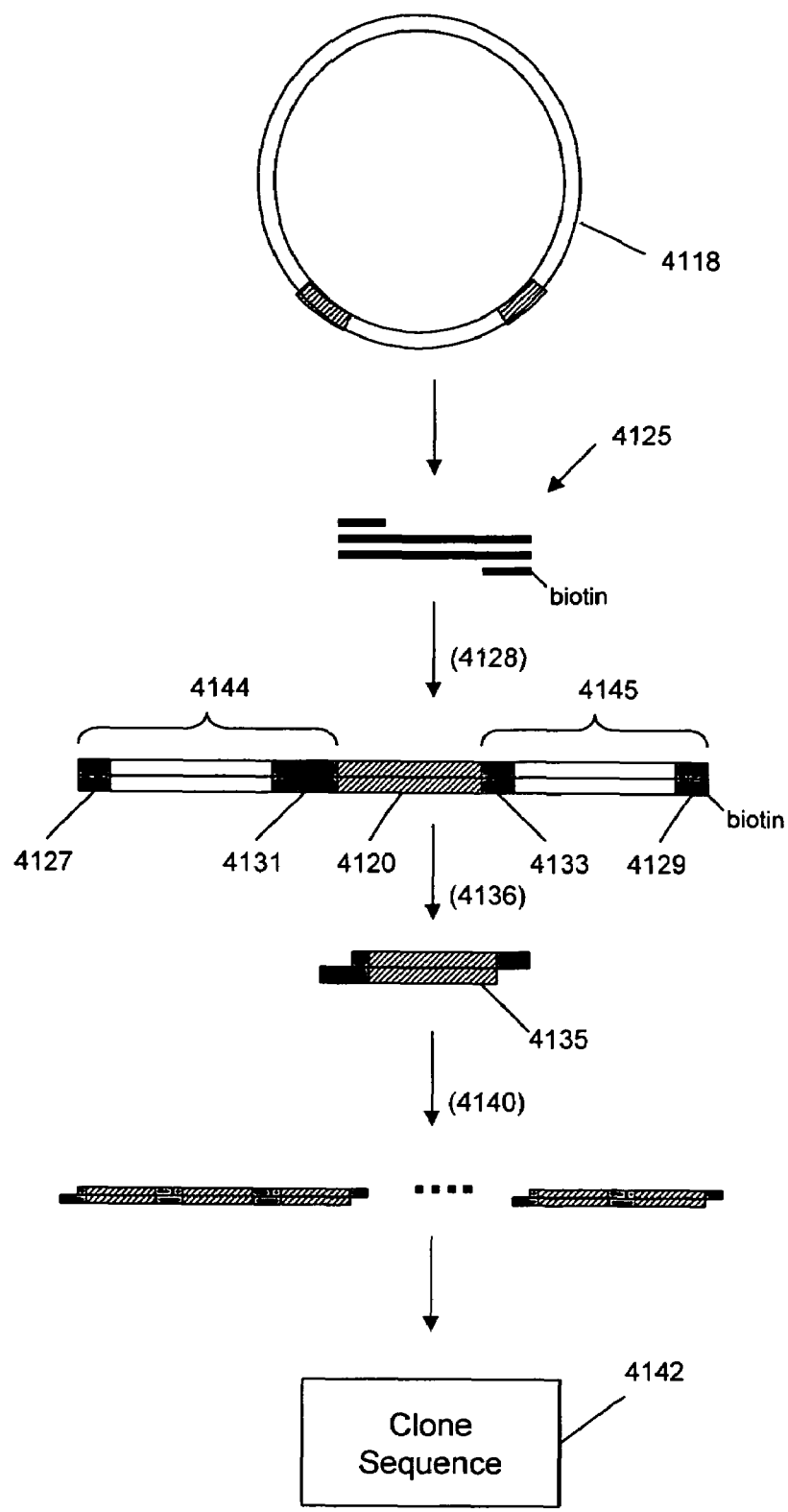
Figure 4C:
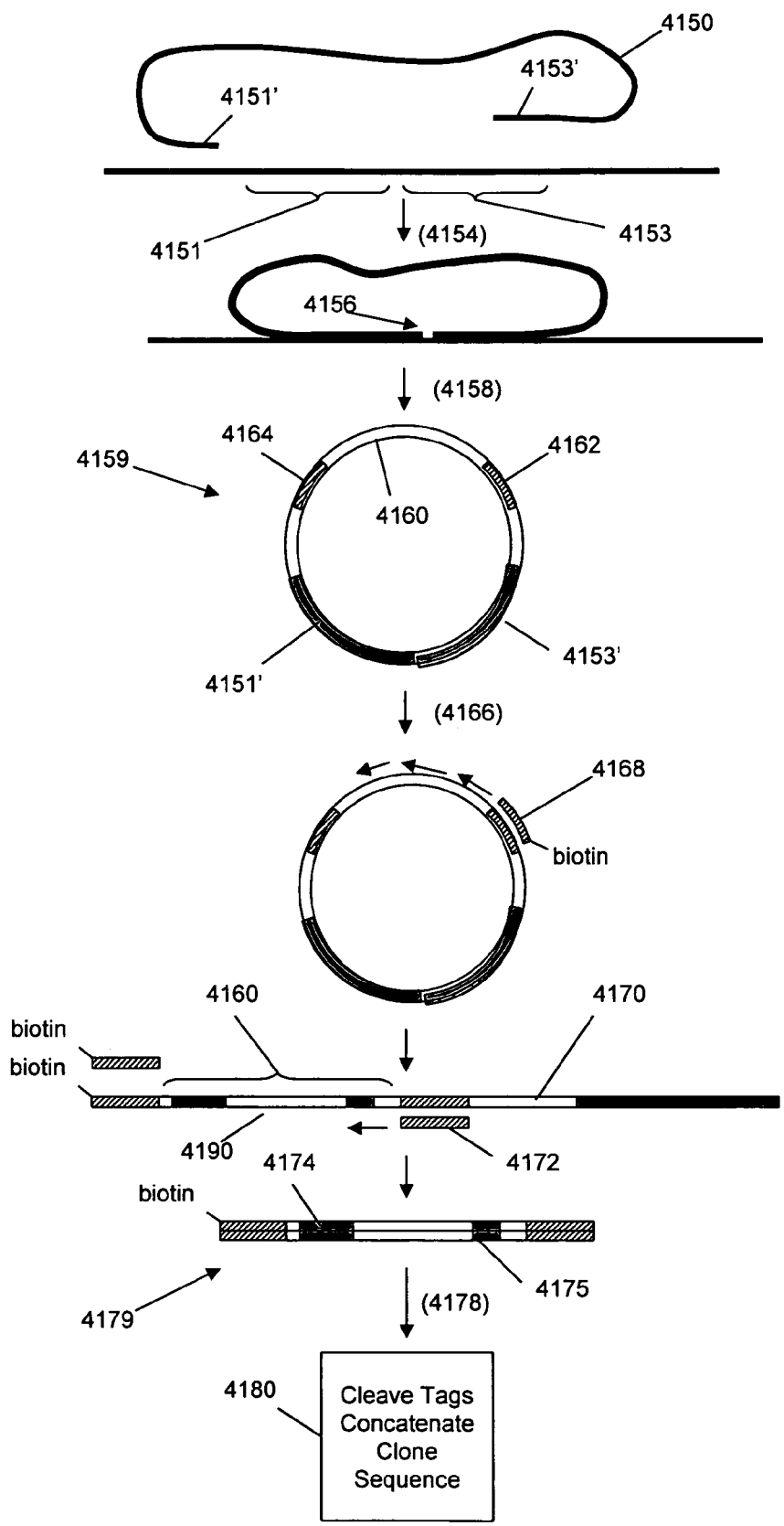

An exemplary embodiment for enumerating restriction fragments is illustrated in FIGS. 4A and 4B, where target polynucleotides are produced by digesting a specimen of DNA, such as genomic DNA, with one or more type IIs restriction endonucleases, e.g. described in Szybalski et al, Gene, 100:13-26 (1991). Type IIs restriction endonucleases are a subset of type II restriction endonucleases that have cleavage sites entirely or partially outside of their recognition sites. Digestion with such enzymes produces fragments having overhangs with random nucleotides (referred to herein as "random-end fragments"). In this aspect, the method takes advantage of prior knowledge of the nucleotide sequence(s) of target polynucleotides in the following manner. First, the recognition sequences of the restriction endonucleases define a set of random-end fragments, and second the sequences of the random ends permit individual fragments to be selected. For a given sized genome, selecting appropriate type IIs restriction endonucleases is a matter of routine design choice. An important factor in such selection is to ensure that the random ends produced by the selected type IIs enzymes provide enough diversity to permit individual fragments to be identified. If a single cleavage with a particular type IIs enzyme does not produce enough diversity to select fragments, then successive cycles of cleavage, adaptor ligation, and nuclease digestion can be implemented, e.g. as described by Callow et al, Nucleic Acid Research, 32:e21 (2004). For large genomes, such as the human genome ($\approx 3 \times 10^9$ basepairs), type IIs restriction endonucleases are preferred that leave long overhangs, e.g. 4-5 nucleotide overhangs. A subset of type IIs restriction endonucleases, referred to herein as "double cleavage type IIs restriction endonucleases," are of special interest because many of them leave fragments having five-nucleotide overhangs. For example, the double cleavage type IIs restriction endonuclease, Bae I (5'-(10/15) ACNNNNGTAYC (12/7) (SEQ ID NO: 20)), generates (on average) about $3.6 \times 10^5$ fragments from human genomic DNA, each fragment having an average length of eight kilobases and each having two 5-nucleotide random sequence overhangs. Ten nucleotides of random sequences provides more than enough diversity $((4^5)(4^5-1)/2 \approx 5.24 \times 10^5$ sequences, Unrau and Deugau, Gene, 145:163-169 (1994)) so that with high probability individual fragments can be selected by providing a circularizing adaptor with complementary ends. Selection by a circularizing adaptor can be enhanced by treating the digested genomic DNA with blocking agents, e.g. oligonucleotides or adaptors that hybridized to undesired ends, particularly those having sequences closely related to the desired ends. In one embodiment, such blocking agents are provided for every single-base mismatch of the desired overhang sequence. Thus, for two five-nucleotide overhangs, 486 ($=2 \times 3^5$) blocking agents are provided. Exemplary type IIs restriction endonuclease that can be used with this aspect of the invention include, but are not limited to, Bae I, Alo I, Ppi I, Psr I, Bpl I, Fal I, Hae IV, Bbv I, Aar I, Bbr 7 I, Bsa XI, Bsl F1, Bsm B1, Bsp M1, Btg Z1, Cje I, Cje P1, Ear I, Fok I, Hin4 I, Sts I, and the like. Returning to FIG. 4A, target DNA (4100) is digested (4102) with one or more type IIs restriction endonucleases to produce a population of random-end fragments (4105), after which the restriction endonucleases are disabled, e.g. by heating. Circularizing adaptor (4107) having ends (4110) and (4112) complementary to ends (4111) and (4113) of fragment (4115) to be selected is added to fragments (4105) under conditions that permit the fragment (4115) and circularizing adaptor (4107) to be ligated (4114) to form dsDNA circles (4118). Circularizing adaptor (4107) contains elements, such as oligonucleotide tag (4120), primer sites (4108) and (4109), restrictions sites, and the like, that permit oligonucleotide tags (4120) of selected dsDNA circles (4118) to be amplified and otherwise manipulated. Preferably, polynucleotides and fragments that do not circularize (4119) are destroyed by digesting (4116) them with one or more nucleases, thereby removing a possible source of background signal. Such nucleases include, but are not limited to, exo I, exo III, exo T, Bal-31, Mung bean nuclease, T7 endonuclease I, and the like.

After double stranded DNA circles (4118) are isolated by digesting non-circularized DNAs, tag portion (4120) of circularizing adaptor (4107) is amplified, either directly from the circular DNA (4118) or after excision by digestion with a restriction endonuclease. In one aspect, tag portion (4120) is excised by digestion with an restriction endonuclease and amplified by PCR using a primer having a capture moiety, such as biotin (4125). FIG. 4B provides an enlarged view of an amplicon resulting from such reaction. Oligonucleotide tag (4120) is sandwiched between restriction endonuclease recognition sites (4131) and (4133) which, in turn, are sandwiched between primer binding sites (4144) and (4145). Ends (4127) and (4129) are the remnants of restriction sites of the enzymes used to excise the fragment. In one embodiment, restriction sites (4131) and (4133) are recognized by different restriction endonucleases that leave identical overhangs. This allows fragments to be readily produced for concatenation, e.g. as taught by Powell, Nucleic Acid Research, 26: 3445-3446 (1998). Exemplary pairs of restriction endonucleases include, but are not limited to, Sau 3A I and any of Bgl II, Bam HI, or Bcl I; Tsp 509I and Eco RI; Tal I and Aat II; Fat I and Pci I; and Nla I and Sph I. Such pairs are used as follows: First, biotinylated amplicon (4125) is captured with streptavidinated beads, then amplicons are digested with the member of the pair having a recognition site distal to the biotinylated end, washed, and digested with the other member having a recognition site proximal to the biotinylated end. Such processing (4136) results in fragments (4135) having ends that permit concatenation (4140) into longer sequences suitable for cloning into a conventional sequencing vector (4142). In other embodiments, restriction endonucleases (4131) and (4133) can leave different ends on fragment (4135).

In reference to the above embodiment, an exemplary circularizing adaptor can have the following sequence (SEQ ID NO: 21):

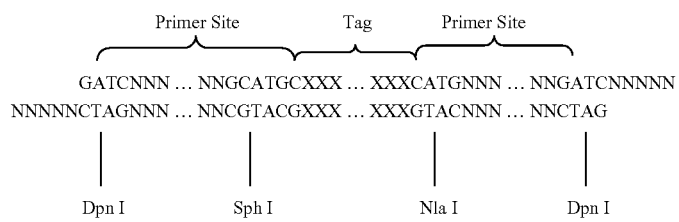

Oligonucleotide tags (4120) can comprise any nucleotide sequence that can be readily distinguished by conventional methods of sequence analysis, e.g. Sanger sequencing, pyrosequencing, or the like. Lengths of oligonucleotide tags (4120) can vary widely and depend primarily on the size of the population of tags that is desired, or necessary, given the number of target polynucleotides to be enumerated. For enumerating target populations having sizes in the range of from 50 to 500 molecules, a population of oligonucleotide tags (4120) is in the range of from 500 to 5000, or more preferably, in the range of from 5000 to 50000. Thus, oligonucleotide tags (4120) having lengths equal to or less than nine nucleotides provide more than enough choices for constructing a set of tags for use with the invention. Preferably, sequences of oligonucleotide tags are selected so that they can be distinguished even in the presence of sequencing errors. Thus, oligonucleotide tags (4120) are selected to be maximally different. In one aspect, oligonucleotide tags (4120) have lengths in the range of from 6 to 12 nucleotides; and more preferably, in the range of from 8 to 12 nucleotides. Regions of an oligonucleotide tag can be allocated to identifying a restriction fragment or target that its associated selected probe is specific for. Such "indexing" is useful when more than one target polynucleotide is being enumerated. For example, as in FISH assays to determine the extent that the ErbB2 gene is amplified, one selected probe can target a region of the ErbB2 gene, while another selected probe can target a region of the genome not expected to undergo any amplification in a patient. Such indexing can also be used to analyze multiple samples using high throughput DNA sequencing instruments, where tags from different patients have different indexing sequences.

As mentioned above, selected probes can be generated using padlock probes, as further illustrated in FIG. 4C. Linear padlock probe (4150) has ends (4151') and (4153') that are complementary to adjacent regions (4151) and (4153) of target polynucleotide (4152). Upon annealing (4154) of such complementary regions, the ends of linear padlock probe (4150) are ligated, thereby closing the gap or nick at (4156) and generating (4158) a closed single stranded circle of DNA (4159). Ends of linear padlock probe can be directly abutting upon annealing, or there can be a gap that is filled either by extension with a nucleic acid polymerase or by ligation of a filler oligonucleotide. After formation of single stranded circles (4159), any remaining non-circularized polynucleotides are digested with one or more exonucleases, such as exo I and/or exo III. Single stranded circle (4159) comprising regions (4151') and (4153') that were complementary to target polynucleotide (4150), primer binding sites (4162) and (4164), and tag-containing region (4160). After single stranded circles (4159) are isolated by digesting non-circular DNA, they are combined (4166) with biotinylated primers (4168) specific for primer binding site (4162) under conditions that allow them to be extended to form extension products (4170) that include tag-containing region (4160) and primer binding site (4164). Primers (4172) are added and portions of extension products (4170) are amplified to form biotinylated amplicon (4179) that contains oligonucleotide tag (4190) sandwiched between restriction endonuclease sites (4174) and (4175), which operate similarly to the embodiment of FIG. 4B. As above, tag-containing regions are excised (4178), concatenated, cloned, and sequenced (4180).

Figure 5A:
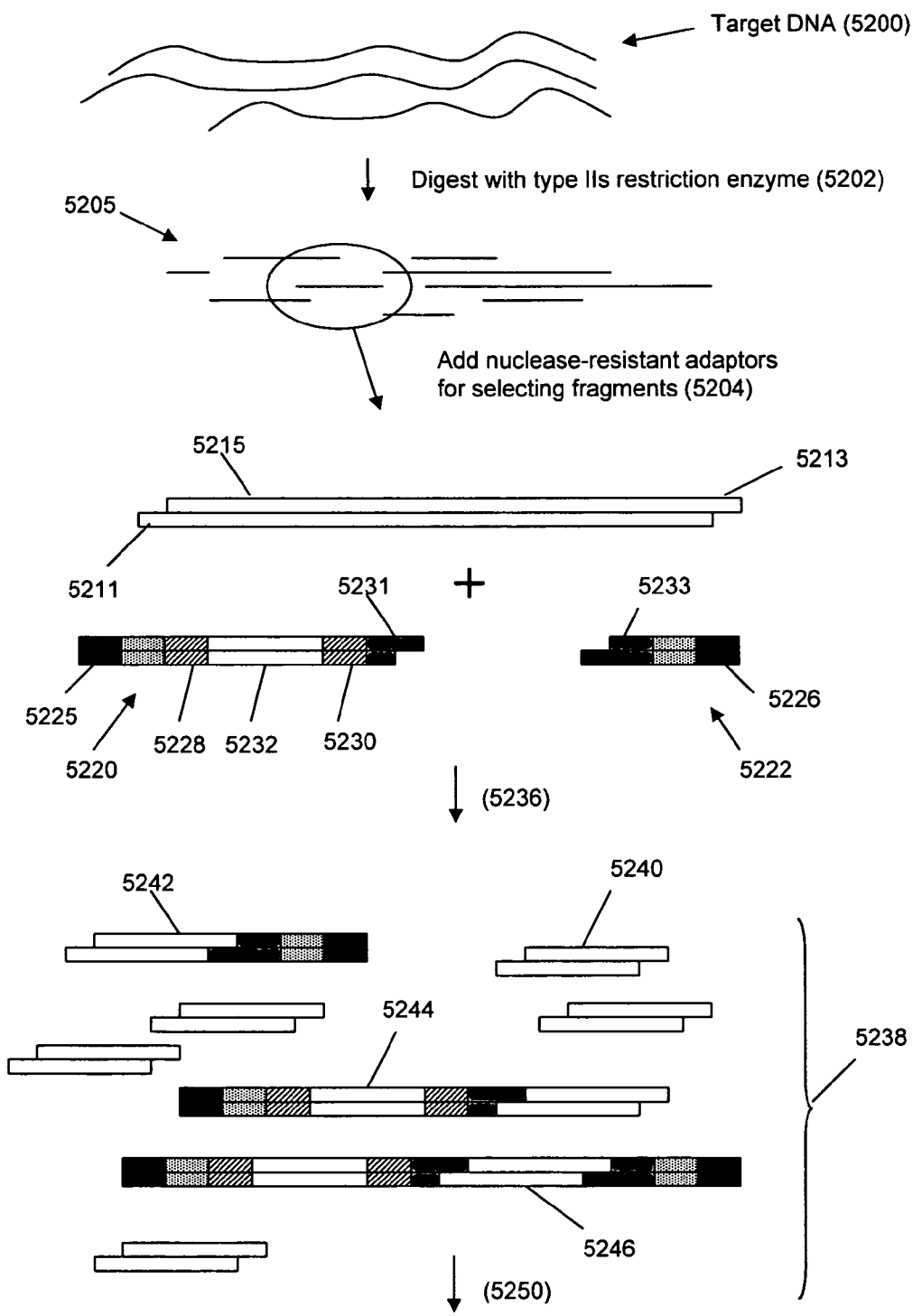
FIGS. 5A-5B illustrate further exemplary embodiments of the invention that employ adaptors having nuclease resistant ends for generating and enumerating selected probes.
Figure 5B:
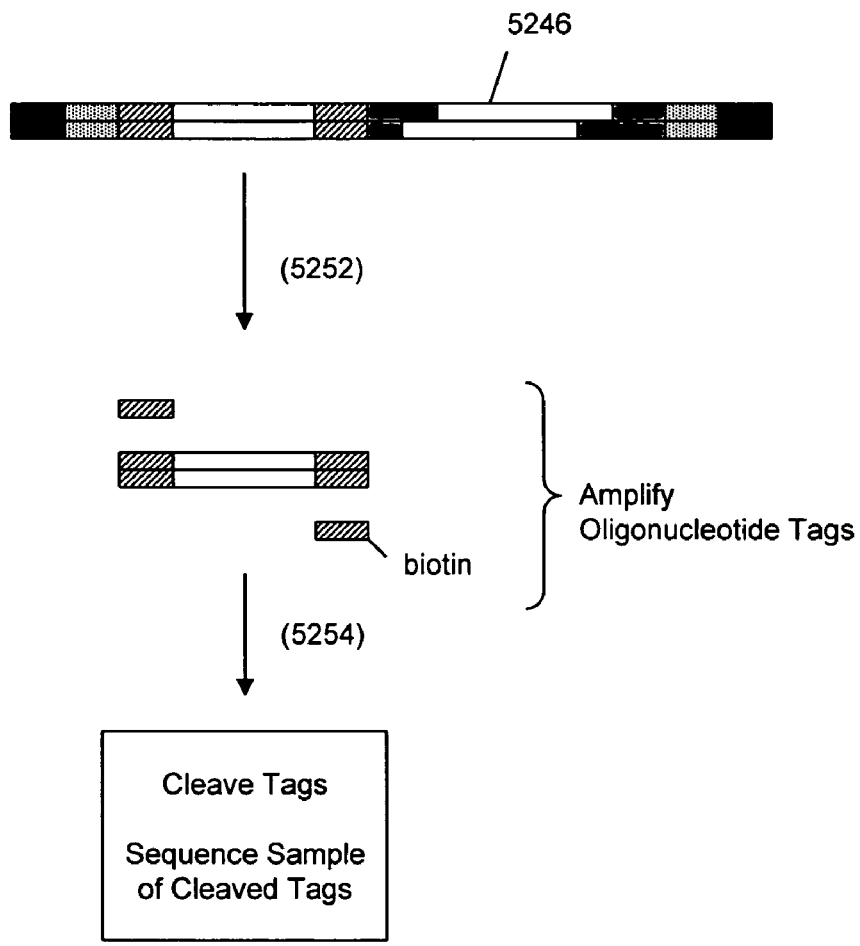

Another aspect of the invention that uses two nuclease resistant adaptors is illustrated in FIGS. 5A-5B. As above, target DNA (5200) is digested (5202) with one or more type IIs restriction endonucleases, preferably ones that leave five nucleotide overhangs so that individual fragments can be selected (5204) by the sequence of complementary overhangs of the adaptors, even in mammalian DNA. From fragments (5205), adaptors (5220) and (5222) are provided that have complementary ends (5231) and (5233) to those of fragment (5215), i.e. (5211) and (5213), respectively. Adaptor (5220) has nuclease resistant end (5225), first primer binding site (5228), oligonucleotide tag (5232), second primer binding site (5230), and complementary end (5231). Adaptor (5222) has nuclease resistant end (5226) and complementary end (5233). Nuclease resistant ends (5225) and (5226) can be regions with nuclease resistant internucleoside linkages, such as phosphorothioates, PNAs, or the like, or they can be hairpin structures that are resistant to certain single stranded exonucleases. After ligation (5236) of adaptors (5220) and (5222) to fragments (5205), several classes of conjugates are formed (5238). There will be conjugates with no adaptors (5240), one adaptor (5242) and (5244), and two adaptors (5246). After treatment (5250) with exonucleases, e.g. exo I and exo III, only conjugates (5246) remain. The oligonucleotide tags are then amplified (5252) out of conjugates (5246), after which a sample of such tags are sequenced and the number of different tags are determined (5254).

Figure 6B:
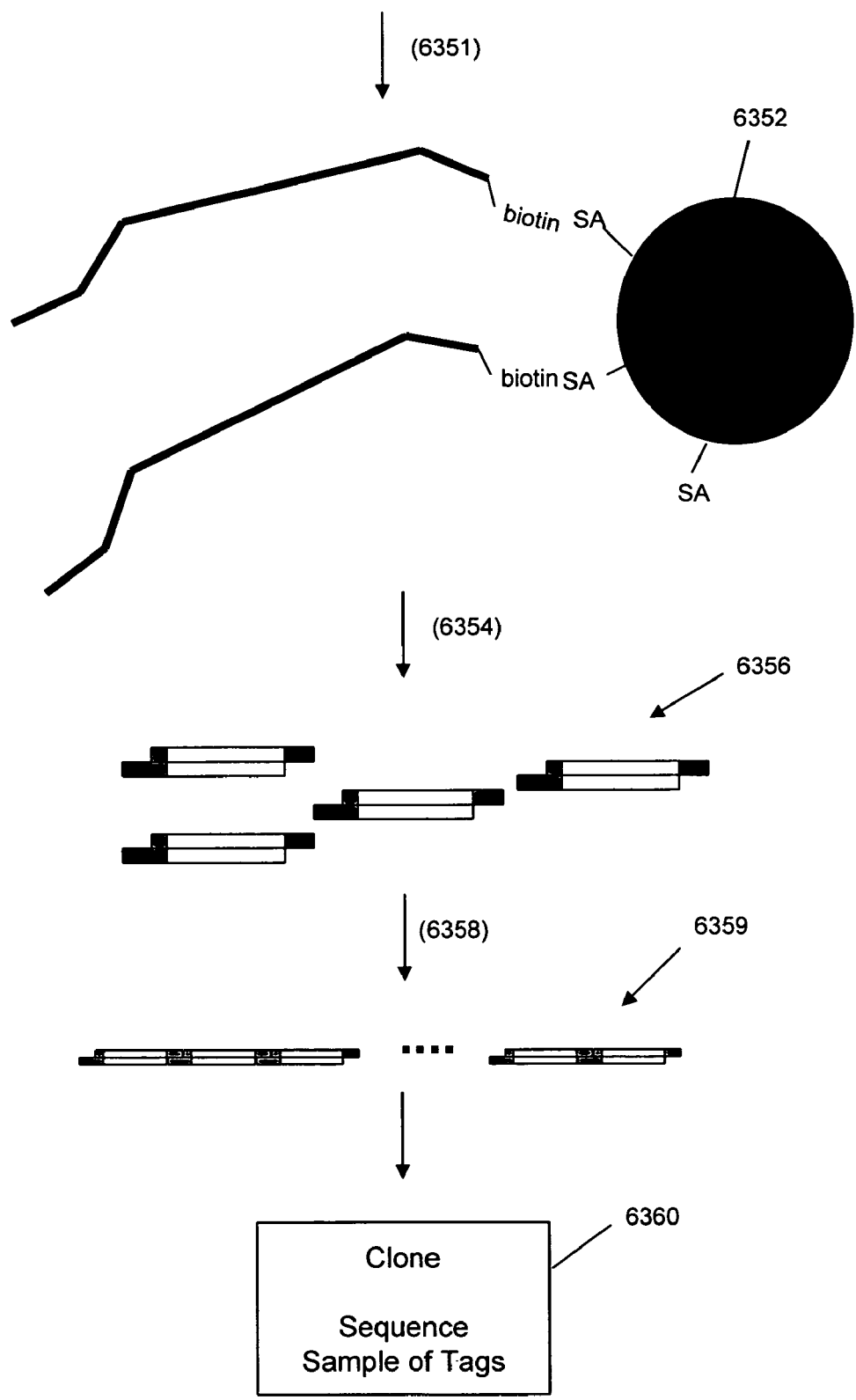

An aspect of the invention that employs template-driven ligation and/or extension to product selected probes is illustrated in FIGS. 6A-6B. First (6340) and second (6342) oligonucleotide probes specifically anneal to target polynucleotide (6350) by forming perfectly matched duplexes between region (6301) and region (6301') of oligonucleotide probe (6340) and between region (6303) and region (6303') of oligonucleotide probe (6342). First and second oligonucleotide probes (6340) and (6342) have primer binding site (6306) and (6308), respectively, for amplification, e.g. by PCR, after a ligation product if formed. As used herein, "ligation probe" refers padlock probes or to probes comprising a pair of separate first and second oligonucleotide probes. Both types of ligation probes can be ligated together in a template-driven reaction, which reaction includes, but is not limited to, a chemical ligation, enzymatic ligation with a ligase, or a ligation that includes a polymerase extension followed by ligation by a ligase. In the case of the former type of ligation probe, ligation results in a ligation product that is a closed single stranded DNA circle. In the case of the latter type of ligation probe, ligation results in a ligation product that is a linear polynucleotide. In one embodiment, after annealing to a target polynucleotide, oligonucleotide probes (6340) and (6342) are abutting so that gap or nick (6312) can be eliminated by ligation, e.g. by a ligase. In other embodiments, the ends of oligonucleotide probes (6340) and (6342) can be separated by a gap of one or more nucleotides. Such gap can be filled (6304) by ligating a separate oligonucleotide (not shown) or it can be filled by extending a 3' end of one of the oligonucleotide probes so that the ends abut, whereupon the ends are ligated. In one aspect, such gap is in the range of from 1 to 40 nucleotides. In another aspect, it is in the range of from 1 to 2 nucleotides; and in another aspect, it is one nucleotide. Procedures for filling such gaps are disclosed in Willis et al, U.S. Pat. No. 6,858,412; and in Hardenbol et al, Nature Biotechnology, 21:673-678 (2003); which are incorporated by reference. An added degree of specificity can be obtained by requiring that a gap be filled by one or two specific nucleotides. Further specificity can be obtained by providing first and second oligonucleotide probes (6340) and (6342) with nuclease resistant ends, i.e. within their primer binding sites, so that after ligation, the reaction mixture can be treated with 3' and 5' exonucleases to digest any unligated probes, e.g. Fan et al, U.S. Pat. Nos. 6,812,005; 6,890,741, which are incorporated by reference. After oligonucleotide probes (6340)

and (6342) are ligated (6314) to form ligation product (6316), primers (6309) and (6311) are added and ligation product (6316) is amplified to form amplicon (6322). Primer (6309) has a capture moiety, such as biotin, so that amplified ligation product (6316) can be captured (6351) by streptavidinated beads (6352). As described above, capture ligation products (6316) is then successively digested with restriction endonucleases recognizing sites (6324) and (6326) to release (6354) oligonucleotide tags (6356) that can be sequenced directly or concatenated (6358) to form concatemers (6359), which are then cloned and sequenced (6360).

As an alternative to concatenating and cloning described above, oligonucleotide tags of selected nucleic acid probes can also be sequenced directly by carrying out an emulsion-based amplification to form clonal populations of oligonucleotide tags from selected probe on beads. The clonal populations on each bead are then sequenced using a high-throughput sequencing by synthesis technique such as described above. Emulsion PCR protocols to form clonal populations of templates on beads are disclosed in Dressman et al (2003), Proc. Natl. Acad. Sci., 100:8817-8822; Li et al (2006), Nature Methods, 3:95-97; Shendure et al (2005), Science, 309:1728-1732; Berka et al, U.S. patent publication 2005/0079510; and Tillett et al, International patent publication WO 03/106698, which are incorporated by reference for their guidance in implementing emulsion PCR. Briefly, after an amplicon is generated, as shown for example in FIGS. 4B (4128), 4C (4179), 5B (5250), or 6A (6322), an aqueous phase solution containing the amplicon, or a portion thereof, e.g. 10-100 pg, and amplification reagents, e.g. for PCR or like technique, is mixed with a light oil, such as mineral oil, and beads derivatized with a primer oligonucleotide so that micro-droplets of aqueous phase solution forms in the oil. The composition of these reagent are selected to maximize the formation of such micro-droplets containing a single bead and a single oligonucleotide tag from the amplicon. Once such an emulsion is formed, conditions are selected for implementing an amplification reaction, such as PCR, after which the emulsion is broken, the beads are collected, and the attached clonal populations of oligonucleotide tags are analyzed, preferably by a sequencing by synthesis technique, such as pyrosequencing.

Figure 7A:
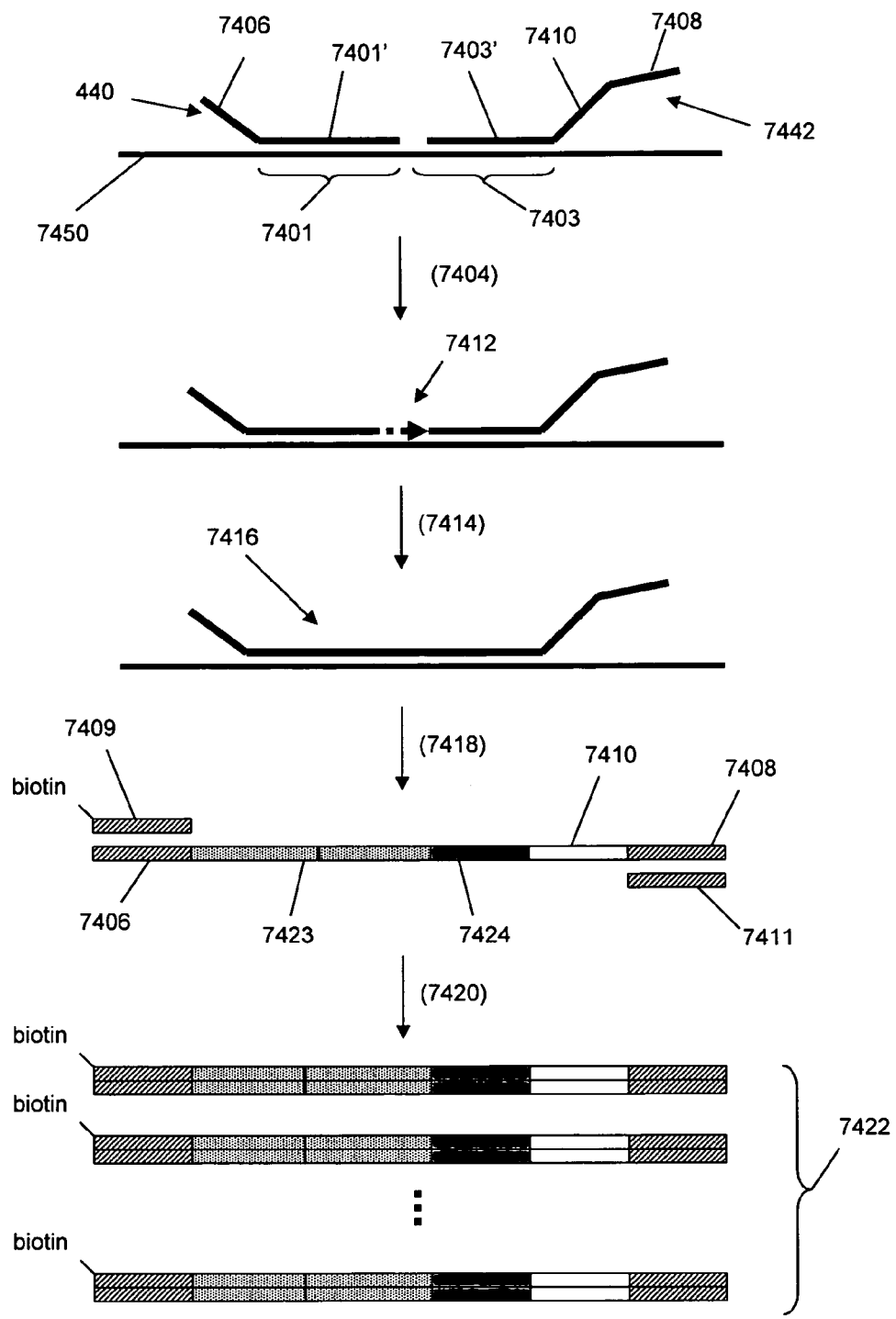
FIGS. 7A-7B illustrate still further exemplary embodiments of the invention that employ emulsion-based amplification and sequencing by synthesis to identify the oligonucleotide tags of selected probes.
Figure 7B:
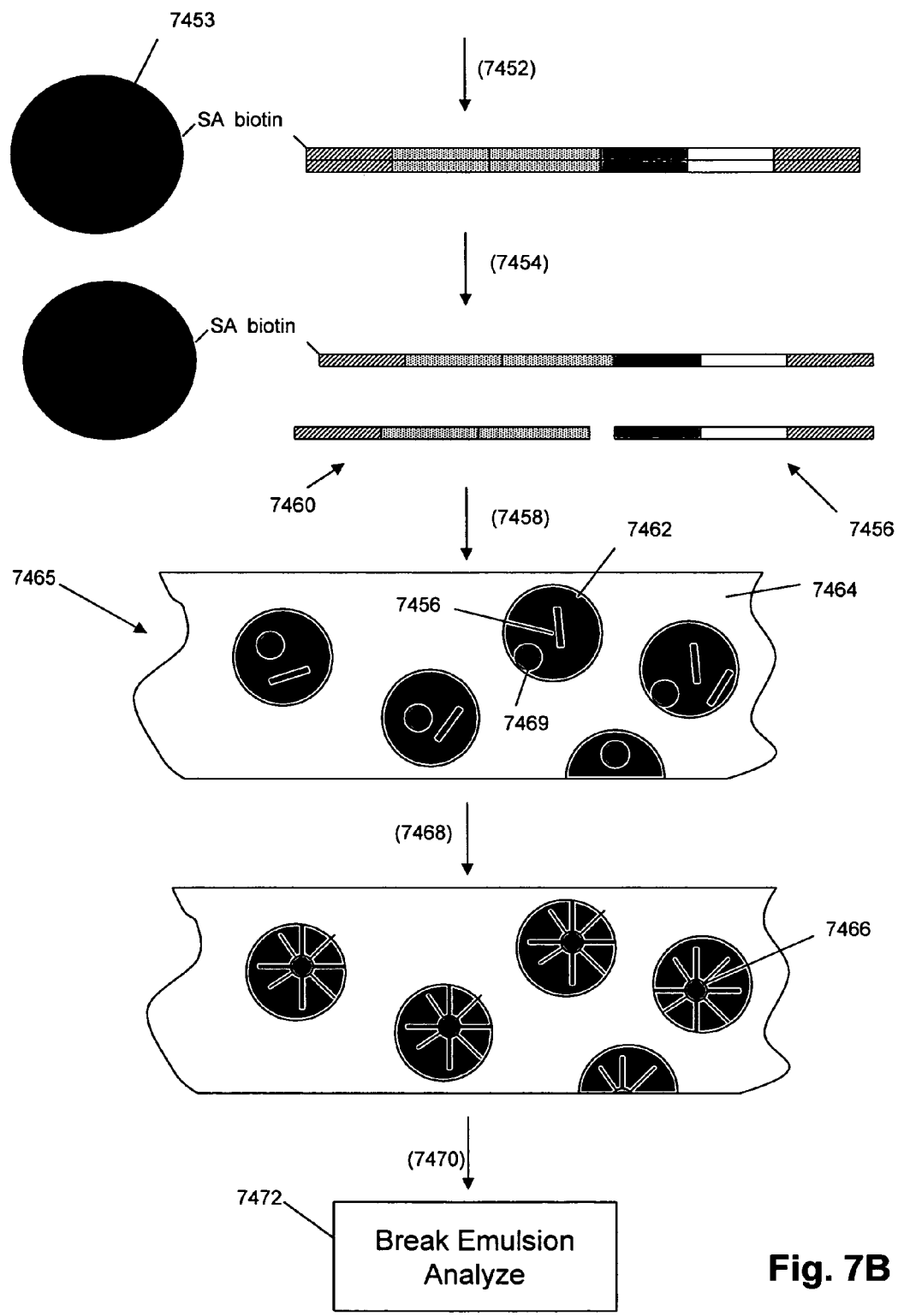

These steps are illustrated in FIGS. 7A-7B for a particular embodiment. Similarly to the embodiment of FIGS. 6A-6B, first and second components (7440) and (7442) of a ligation probe are annealed via segments (7401') and (7403') to regions (7401) and (7403), respectively, of target polynucleotide (7450), where a template-driven extension and/or ligation reaction (7412) is carried out (7404) to join (7414) the two components at the indicated ends. As above, component (7440) of the ligation probe has primer binding site (7406) and component (7442) of the ligation probe has primer binding site (7408) and oligonucleotide tag-containing region (7411). In this embodiment, region (7410) includes oligonucleotide tag (7410), primer binding site (7424), and primer binding site (7408). The sequence of primer binding site (7424) further contains a nucleotide sequence that in double stranded form is a recognitions site of a type IIs nicking enzyme such as N.Alw I, or the like, oriented so that the single stranded piece containing primer binding site (7424), oligonucleotide tag (7410), and primer binding site (7408) is capable of being released from amplicon (7422) after capture by streptavidin. After selected nucleic acid probe (7416) is generated by extension and/or ligation, it is amplified (7418), for example, using PCR with primers (7409) and (7411) to form amplicon (7422). Amplicon (7422) is captured (7452) by streptavidinated beads (7453), washed, and treated with nicking enzyme (7454) to release fragments (7460) and (7456). Several different beads may be used for beads (7453). In one aspect, beads (7453) are 1.0 μm diameter superparamagnetic beads, e.g. available from Dynal, as disclosed by Dressman et al (cited above). Fragments (7456) and (7460) are combined with amplification reagents, including primers specific for sites (7434) and (7408), to form the aqueous component of an emulsion. Such aqueous component is combined with beads (7467) derivatized with oligonucleotides complementary to site (7424) and mineral oil (7464) so that emulsion (7465) forms containing microdroplets (7462). The concentration of beads, concentration of fragments (7456), and microdroplet size are selected so that a substantial fraction of microdroplets contains one bead (7469) and one fragment (7456), as show with microdroplet (7462). In one aspect, a substantial fraction is at least 1% of the microdroplets; in another aspect, a substantial fraction is at least 5% of the microdroplets; in another aspect, a substantial fraction is at least 10% of the microdroplets; and in still another aspect, a substantial fraction is at least 25% of the microdroplets. Once the above emulsion is formed, PCR is carried out (7468) so that a detectable number of primer oligonucleotides attached to beads (7469) are extended to form loaded beads (7466) that are capable of being analyzed by sequencing by synthesis. In one aspect, a detectable number of extended primers is at least 10,000. After breaking the emulsion and isolation of loaded beads (7466), the attached fragment are analyzed as described by Shendure et al (cited above) or by Margulies et al (cited above).

The size of the sample of oligonucleotide tags from selected probes that is sequenced is a design choice in that the more oligonucleotide tags that are sequenced the greater the probability that every different oligonucleotide tag (and hence the correct number of target polynucleotides) will be determined. The circumstances are directly analogous to the process of screening for rare cDNAs in a library, as described in Maniatis et al, Molecular Cloning: A Laboratory Manual (Cold Spring Harbor Laboratory, 1982), page 225, which is incorporated by reference. Briefly, the number of oligonucleotide tags that is requires to be sequenced to achieve a given probability that every one will be detected is given by the formula: $N=\ln(1-P)/\ln(1-r)$, where N is the number of tags required, P is the desired probability, and r is the frequency of a tag in the sample. For example, if P=0.99 and r=0.005, then N=921. That is, when there are about 200 target polynucleotides to be enumerated, then about 1000 tags must be sequenced to detect everyone with 99 percent probability, or about 600 tags must be sequenced to detect everyone with 95 percent probability.

Oligonucleotide Tags for Specialized Sequencing Chemistries

An important feature of the invention is the selection of sets of oligonucleotide tags that are designed for use with specialized sequencing chemistries to improve discrimination, minimize errors, improve base calling, and the like. Of particular interest are DNA sequencing chemistries that generate a signal monotonically related to the size of a homopolymeric region of a target polynucleotide, such as pyrosequencing, disclosed in the following references that are incorporated by reference: Nyren et al, U.S. Pat. No. 6,210,891; Ronaghi, U.S. Pat. No. 6,828,100; Ronaghi et al (1998), Science, 281:363-365; Ronaghi (1998) doctoral thesis, ISBN 91-7170-297-0. Oligonucleotide tags determined by this class of sequencing approaches can be more readily determined if all members of a set of such tags have no homopolymeric regions, or have homopolymeric regions that are sufficiently short so that there is no ambiguity in calling the bases of tag sequences. Accordingly, for such oligonucleotide tags, homopolymeric regions are less than or equal to five nucleotides in length. In another aspect, such homopolymeric regions are less than or equal to four nucleotides in length; and in another aspect, such homopolymeric regions are less than or equal to three nucleotides in length. In a preferred aspect of the invention, such homopolymeric regions are less than or equal to two nucleotides in length; and in a most preferred aspect, there are no homopolymeric regions in oligonucleotide tags of the invention. In other words, in the most preferred aspect, each kind of base in an oligonucleotide tag is immediately followed by a different kind of base. Nucleotide sequences of sets of such oligonucleotide tags are readily generated by conventional computer programs that generate all possible sequences of a preselected length followed by sorting all prospective tag sequences that fulfill the desire criterion on homopolymer size.

The lengths of the oligonucleotide tags of the invention can vary widely depending on several factors including (i) the number of tags desired, (ii) the length of homopolymeric region that can be tolerated, (iii) constraints on the overall length of the tag, and the like. In one aspect, oligonucleotide tags of the invention have lengths in the range of from 6 to 48 nucleotides; in another aspect, oligonucleotide tags of the invention have lengths in the range of from 8 to 36 nucleotides; in still another aspect, oligonucleotide tags have lengths in the range of from 8 to 24 nucleotides. For several different tag lengths, the maximum number, $N_s$, of oligonucleotides tags that have no homopolymeric regions are given by the following formula: $N_s=(3/4)^{n-1}$ where n is the length of the oligonucleotide tag. Thus, for example, the maximum number of such 8-mer, 10-mer, and 12-mer tags is 8748; 78,732; and 708,588; respectively.

Likewise, the size of the sets of such oligonucleotide tags employed in an analytical application can vary widely. In copy number measurements where labeling by sampling is employed, the size of such sets are preferably at least ten times the number of target polynucleotides to be counted; and in another aspect, such sets are preferably at least 100 times the number of target polynucleotides to be counted. Where labeling by sampling is not employed, preferably, the size of sets of oligonucleotide tags of the invention are at least 100, and in another aspect, at least 1000; and in still another aspect, at least 10,000.

Subsets of the above oligonucleotide tags may also be formed based on criteria for enhancing the reliability of base calling in a sequencing approach. Such other criteria includes, but is not limited to, (i) removal of tag sequences that are difficult to sequence with a sequencing chemistry being employed, high GC regions, (ii) removal of tag sequences that are capable of forming hairpins, or other tertiary structures, (iii) selection of tag sequences that permit to implementation of a parity code to provide sequencing quality control, e.g. Gunderson et al (2004), Genome Research, 14:870-877, (iv) selection of tag sequences that are, in some sense, maximally different, e.g. exemplary distance measures for sequences applicable to the invention are well known and are widely disclosed in the literature, as exemplified by the following references: Gusfield, Algorithms on Strings, Trees, and Sequences: Computer Science and Computational Biology (Cambridge University Press, 1997); Navarro et al, Flexible Pattern Matching on Strings (Cambridge University Press, 2002); Sankoff et al, editors, Time Warps, String Edits, and Macromolecules: The Theory and Practice of Sequence Comparison (Center for the Study of Languages, 1999); and the like.

Direct Counting of Metric Tags

Figure 7C:
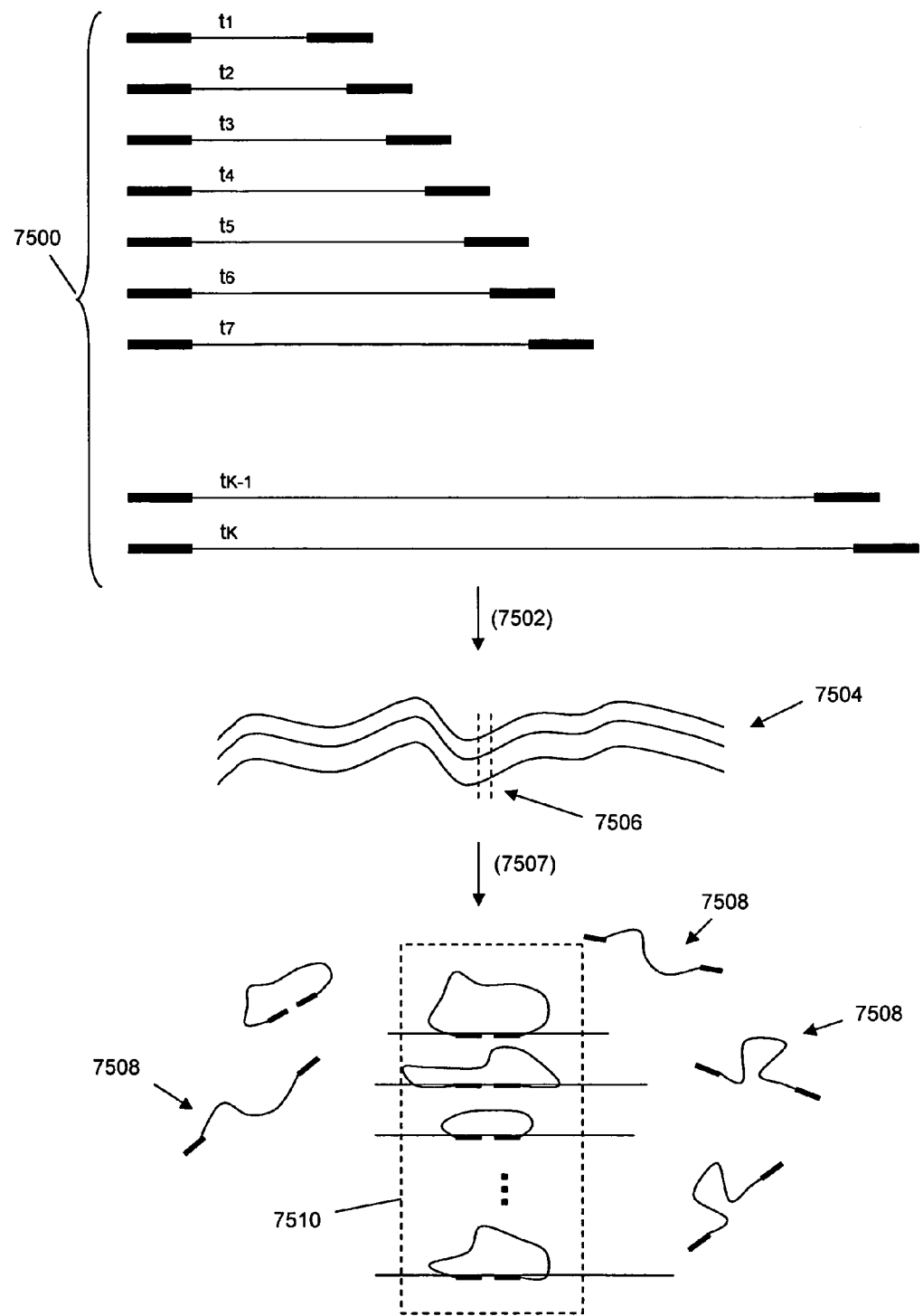
FIGS. 7C-7D illustrate an embodiment of the invention wherein metric tags are directly counted after separation to give an estimate of the number of target molecules in a sample.
Figure 7D:
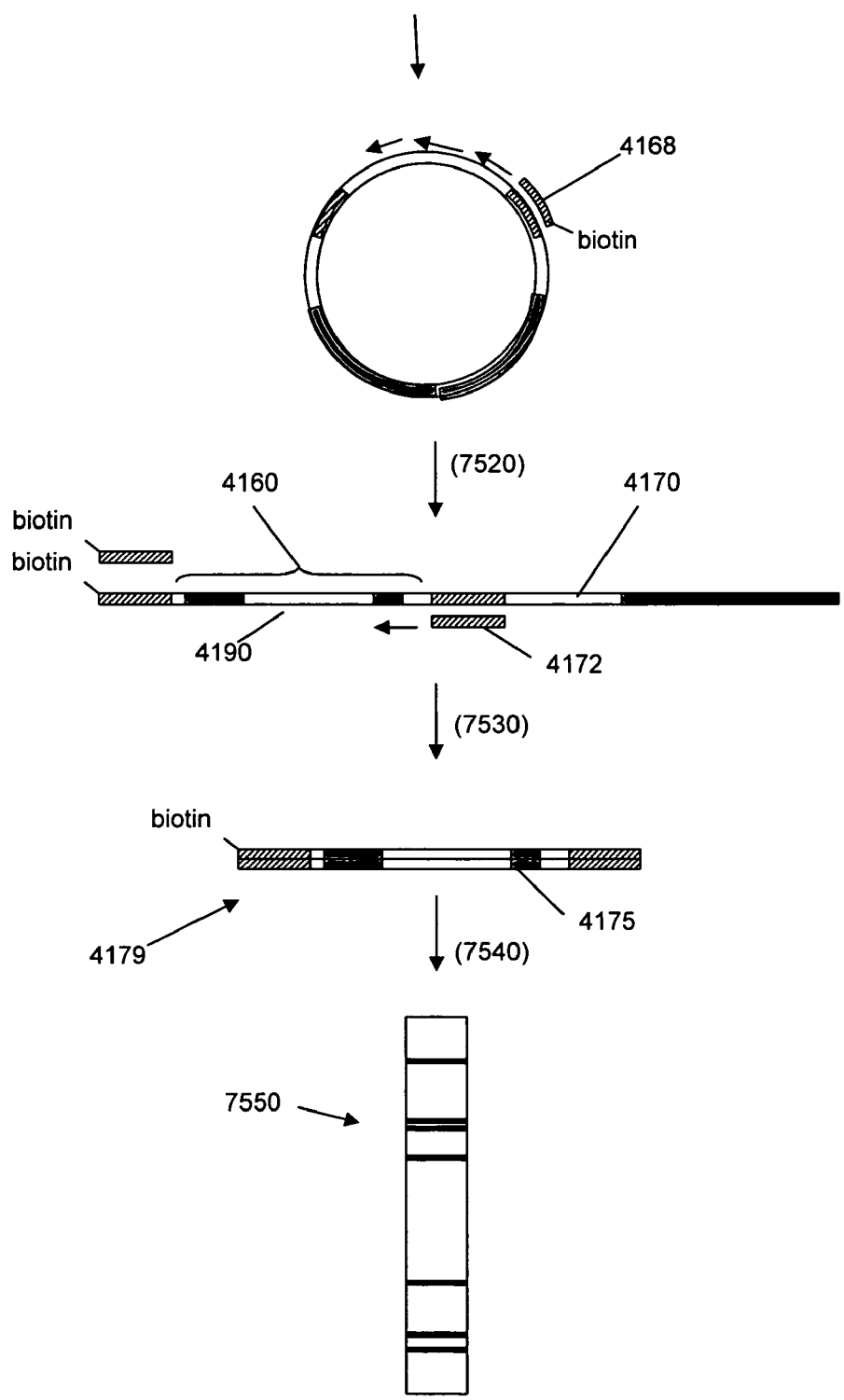

In one aspect of the invention, separated metric tags may be directly counted to determine a number of target molecules. This aspect is with the same steps as described for the embodiments of FIGS. 4C, 6A-6B, and 7A-7B, except that instead of determining the nucleotide sequences of selected tags, the lengths of the selected tags are determined. Such aspect may be carried out with the following steps: (a) labeling by sampling each target polynucleotide in the mixture so that substantially every target polynucleotide has a unique metric tag; (b) amplifying the metric tags of the labeled target polynucleotides; (c) separating the amplified metric tags to form a separation profile of distinct bands; and (d) counting the number of distinct bands of metric tags, thereby estimating the number of target polynucleotides in the mixture. As illustrated in FIGS. 7C-7D, and as described above, in the labeling by sampling step probes containing metric tags are combined with the polynucleotides to be counted under conditions where (i) the probes a capable of forming stable complexes with the target molecules, in this case, stable duplexes, (ii) the number of probes are in great excess over the number of target polynucleotides so that substantially every target polynucleotide associates with a probe, e.g. by forming a stable duplex, and (iii) a ligation, or extension, or like reaction can take place so that probes that interact with target polynucleotides can be separated from those that do not. Using conventional DNA sequencing instruments, as many as 1000 single stranded DNA fragments, or more, can be separated; thus, metric tags may be used directly to count target molecules whenever about 1000 tags (for use of a single label) or about 4000 tags (for 4-color labeling of fragments) are enough to provide samples of tag-molecule conjugates wherein substantially every molecule has a distinct tag. One embodiment of this aspect is illustrated in FIGS. 7C-7D, in which metric tags are incorporated into probes that form covalently closed circles upon successful hybridization to target sequences. Probes (7500) containing metric tags $t_1$ through $t_K$ are combined (7502) under hybridization conditions with a sample of DNA including target sequences to be counted, which for example may correspond to a specific region (7506) of genomic DNA (7504). As described above, preferably the number of different metric tags ($t_1$ through $t_K$) is sufficiently greater than the number of target sequences so that substantially every target sequence to which a probe anneals leads to a circularized probe have a metric tag with a different length. After successfully annealed probes (7510) are ligated to form DNA circles, such circles may be processed using substantially the same steps as described for the embodiment of FIG. 4C. Namely, in one aspect, metric tags (4160) in circle (4159) are copied by annealing biotinylated primer (4168) to primer binding site (4162) and extending through flanking primer binding site (4164), after which the biotinylated strands are captured (7520). After washing to remove unhybridized and uncircularized probes, the captured strands are again amplified (7530) using a primer having a capture moiety, e.g. biotin again. The resulting amplicon is captured and the metric tags are released as described above, after which they are separated (7540), e.g. electrophoretically, to form a separation profile in which distinguishable bands (7550) form that can be counted. Primer (4172) can be designed to contain a type IIs restriction endonuclease site that leaves a 3'-extendable end adjacent to any one of four different nucleotides in the template strand. Thus, after capture, amplicon (4179) may be cleaved with such type IIs endonuclease to leave 3' extendable ends that may be treated with a polymerase and four separately labeled dideoxynucleoside triphosphates to produce up to four separately labeled metric tags for each one of the same length. Exemplary type IIs restriction endonucleases for such labeling include Aar I, Alw I, Bbs I, Bfu AI, Bsm AI, Ear I, Fok I, Sap I, and the like.

Application of Molecular Counting to Methylation Analysis

Free DNA exists in blood serum and can be employed as a biomarker for various conditions, for example, the health of a fetus, the state of a tumor, and the like. Typically, free DNA fragments in the blood are small, 100 to 200 bases. They appear to be nucleosome fragments that have escaped complete digestion by DNase. (A knockout of the DNase II gene, the lysomal DNase, in mice results in major increases of the fragments in blood). In one aspect, molecular counting of the invention may be applied to enumerate specific fragments of fetal DNA detected in maternal blood based on differences in methylation of DNA. Likewise, in another aspect, molecular counting of the invention may be applied to enumerate specific fragments of tumor DNA detected in a patient's blood based such differences. One implementation of this application uses restriction endonucleases that cleave in CpG-rich regions of genomes. Such enzymes are well-known and are disclosed in references, such as Dai et al, Genome Research, 12:1591 (2002), and the like, which are incorporated herein by reference.

Fragments are selected that contain rare restriction sites that are concentrated in CpG islands and that are methylation sensitive. Several such enzymes are available, such as Not I cutting at GC|GGCCGC and Asc I cutting at GG|CGCGCC. There are about 30,000 CpG islands in the human genome and Not I, with 9628 sites, covers 8239 of these, and Asc I, with 4935 sites, covers 4071. If both enzymes are employed 11,210 CpG islands, or about one third of the total, will be covered. In one aspect, using the methods described above, sequences surrounding the restriction sites can be converted into metric tags and identified by sorting and reading after separation. In addition to Not I and Asc I, the following restriction endonuclease may also be used: Rsr II, SgrA1, and Sal I. Employing such enzymes, steps of a method for isolating and counting selected sequences from blood are as follows:

1.) Purify DNA from serum, optionally using a suitable carrier. In one aspect, a carrier may comprise DNA fragments with ends blocked with dideoxys, or like moieties. For example, a Sau III digest filled in with dideoxyG using conventional techniques could be employed. In one embodiment, such carrier DNA could be made for DNA that contains few or not Not I or Asc I sites, i.e. few or no sites of the analyzing restriction endonuclease.

2.) To such purified DNA add one or more nucleotides to the ends. For example, such additions may be made using a terminal transferase in a conventional reaction, such as in cDNA cloning protocols. In one aspect, one or more nucleotides are added. In another aspect, 3 to 4 nucleotides are added, such as riboguanidine.

3.) Attach adaptors to the fragments by ligation (referred to here as the "A adaptors"). These adaptors have nuclease resistant 5' ends distal from the ligation site. For example, they may be produced with phosphorothioate linkages at the appropriate 5' end.

4.) Copy once: methylated sites are half methylated, but still resistant to endonuclease cleavage.

5.) Split the mixture into two fractions. Cut both fractions with an enzyme selected from the set described above. (i) Use one fraction to select cut ends by fill-in with an appropriate nucleotide and ligation to a new adaptor (call this the "adaptor B"). Each enzyme can be done separately with a new (different) adaptor B for each. (ii) In the other fraction, destroy the cut ends with a 5' exonuclease, such as T7 exonuclease, or like enzyme. The A adaptors have nuclease-resistant 5' ends; thus, they will not be digested. Fragments uncleaved by the CpG-specific endonuclease are likewise protected from digestion. The 3' ends of the A adaptors are degraded so they do not participate further. This fraction is amplified by another round of copying, which produces one copy which is unmethylated. This can be cut and selected by ligation to another adaptor (referred to as "adaptor C"). In one aspect, different adaptor C's are used for each different CpG specific endonuclease.

6.) The two libraries of fragments from 5.) may conveniently be compared using a microarray manufactured with array elements complementary to sequence regions adjacent to the recognition sites of the CpG-specific endonucleases employed. Oligonucleotides in such elements may have lengths in the range of from 8 to 65 nucleotides, or from 8 to 50 nucleotides, or from 8 to 25 nucleotides. In one aspect, fragments of interest are those that are completely methylated or completely unmethylated (detected by substantial absence of signal from the element corresponding to the unmethylated fragment).

In one aspect, probes to sequences that are characteristically methylated in a mother and unmethylated in a fetus (or the reverse) are used for counting specific sequences in the above fragment libraries.

EXAMPLE I

Construction of a Metric Tag Set

Figure 8B:
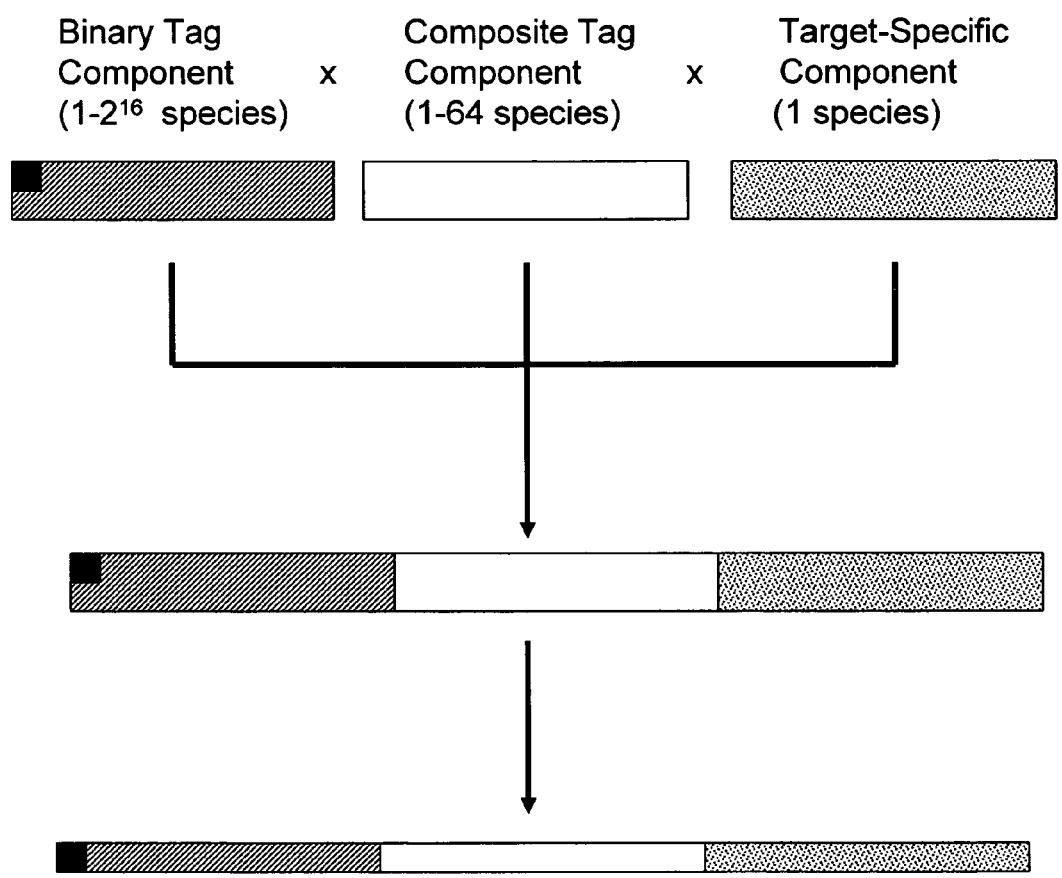
FIG. 8B illustrates diagrammatically the construction of a set of probes for use with the invention to count target nucleic acid molecules.

In this example, a set of 64 double stranded composite tags was constructed wherein each composite tag contains a double stranded metric tag, both of whose complementary single strands are in the range of from 28 to 91 bases in length after Kpn I digestion. The lengths of metric tags that may be released from composite tags in accordance with this example are listed in Table II of FIG. 8A. Such tags are used as outlined in FIG. 8B. That is, in one embodiment, a set of probes (800) is produced having three components: binary tag component (802), composite tag component (804) (which comprises a metric tag), and target-specific component (806). In this embodiment, the top strand of binary tag component (802) is shown as having a 5' exonuclease-resistant end (filled-in box (808)), which allows conversion to single stranded form. The three components are combined (810), e.g. by ligation, to produce double stranded probe (814), which, in turn, is converted to the single stranded probe (800), e.g. by T7 exonuclease digestion. This example illustrates one method of constructing composite tags containing metric tags.

Two sets of eight oligonucleotides each were synthesized, designated $R_0$ to $R_7$ and $T_0$ to $T_7$. Sequences of oligonucleotides $T_0$ to $T_7$ are given in FIG. 3, and sequences of $R_0$ to $R_7$ are given below. The sets oligonucleotides were ligated together in a combinatorial fashion to give 64 composite tags having the form "RTR." All tags were cloned into an Invitrogen TA PCR cloning vector pCR2.1-TOPO, after which tag sequences were validated by conventional DNA sequence analysis.

$R_0$ through $R_7$ have sequences as follows:

Let w, x, y, and z have the following sequences:

```
w = TGTG, x = AAAG, y = TTTGTAGAAGTA,      (SEQ ID NO: 30)
and z = ATGTGATTGTAA;      (SEQ ID NO: 31)
then R_0 = w, R_1 = wxw, R_2 = wzw, R_3 = wyR_1, R_4 = R_2yw, R_5 = wxR_4, R_6 = R_4zw,
and R_7 = R_6xw.
```

Figure 8C:
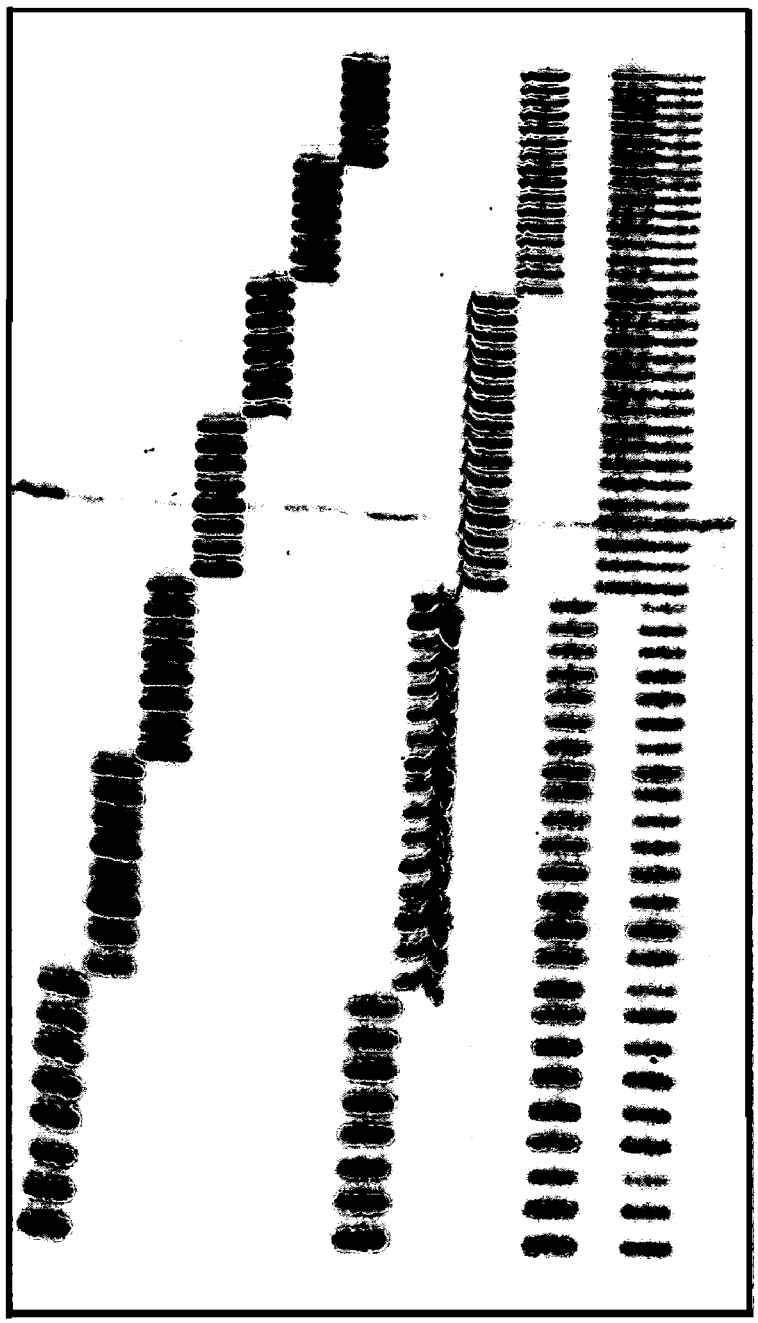
FIG. 8C is an image of several mixtures of metric tags that have been electrophoretically separated.

The DNA concentration of each of 64 plasmid DNA samples carrying cloned composite tag inserts for 64 validated tags was measured using a nanodrop spectrophotometer, after which equimolar mixtures of sets of plasmids were used as template in PCR reactions with common primers for amplifying the tags from the plasmid templates. One primer carried a biotinylated end, the other a fluorophore Cy5. Thus after PCR, the products were captured with streptavidin beads, then digested with Kpn I to release the metric tag end carrying the Cy5 fluorophore for analysis by electrophoresis on a polyacrylamide sequencing gel. Separated metric tags were visualized on a Typhoon Trio phospho-imager. The above was implemented for various mixtures of tags using essentially the same protocol as follows for 64 tags. 64 plasmid recombinants of pCR2.1-TOPO carrying the 64 "RTR" fragments were mixed to a final concentration of 1 ng/µl of each RTR tag: equivalent to $2.5 \times 10^8$ molecules of each template per µl. The plasmids carrying tags $R_2T_0R_5$—44 bases long—and $R_2T_3R_5$—47 bases long—were not included in the experiment in order to provide a useful frame of reference for the other metric tags. PCR was performed in a total volume of 50 µl using 1U HotstarTaq (Qiagen) per reaction with the following cycle conditions: initial 95° C./15 min//35 cycles of 94° C./20 sec, 52° C./20 sec, 72° C./20 sec//72° C./10 min, 4° C. using the following pair of primers: Cy5 labeled 5' end primer (M6) and biotinylated 3' end primer (SPR) each at a concentration of 0.4 pmol/µl. Then half of each PCR reaction was bound to 10 ul of magnetic Streptavidin-beads (10 min), washed once with binding buffer (recipe provided with the product datasheet), once with Tris-Magnesium chloride buffer and once with NEB restriction buffer 1. The digest with KpnI took place in a volume of 10 µl NEB buffer 1 (2.5 units KpnI/37° C./2 h). Then the supernatants (containing the Cy5-labelled portion of the KpnI generated fragments) were individually collected and mixed with equal volumes of 2×Formamide loading buffer. Then 2 µl of each sample were subjected to denaturing polyacrylamide gel electrophoresis (8%, 70 mA, 2 h 30 min). The fluorescence of the labeled bands was detected by laser scanning (Typhoon Trio, Amersham). FIG. 8C is an image of metric tags released by KpnI digestion of Cy5 labeled PCR products and separated electrophoretically on an 8% poly(acrylic acid) gel: lane 1: R0T0-7R7 to lane 8: R7T0-7R0; lane 9-12: mixtures of each 16 tags; lanes 13, 14 mixture of each of 32 tags; lane 15: all 64 tags; lane 16: background control.

EXAMPLE II

Construction of a Binary Tag Set

Figure 9A:
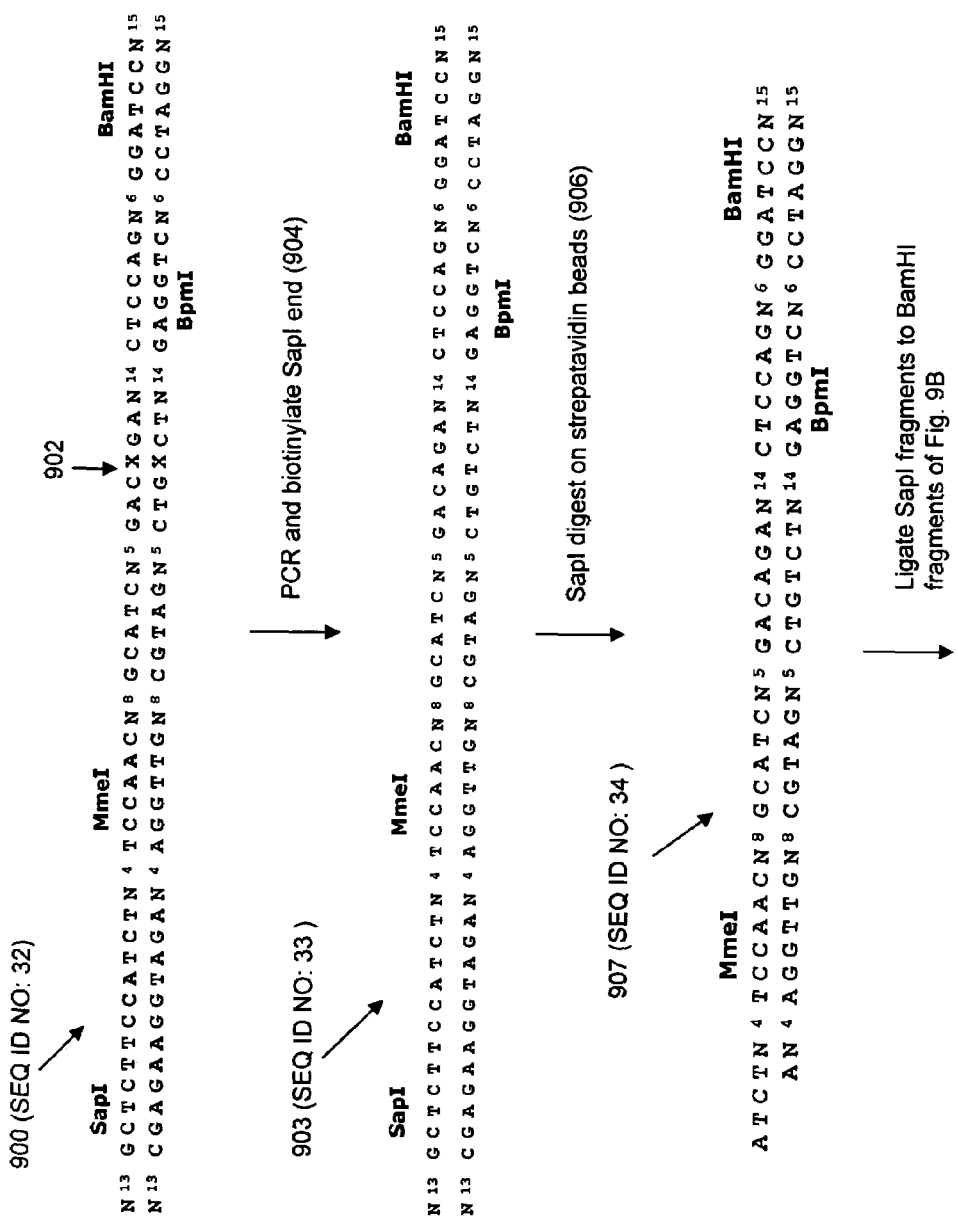
FIGS. 9A-9E illustrates a scheme for generating sets of binary tags of a predetermined size.
Figure 9B:
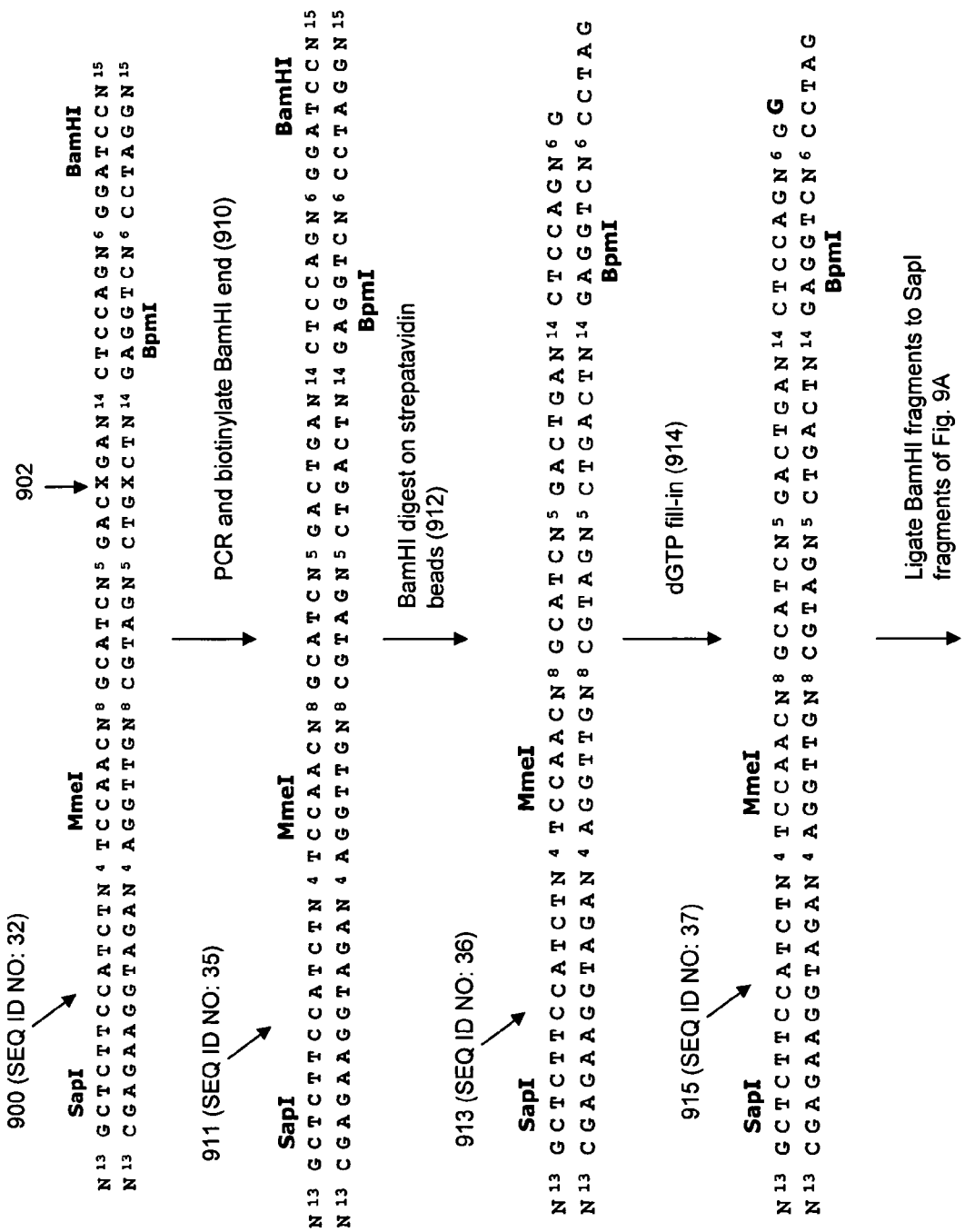
Figure 9C:
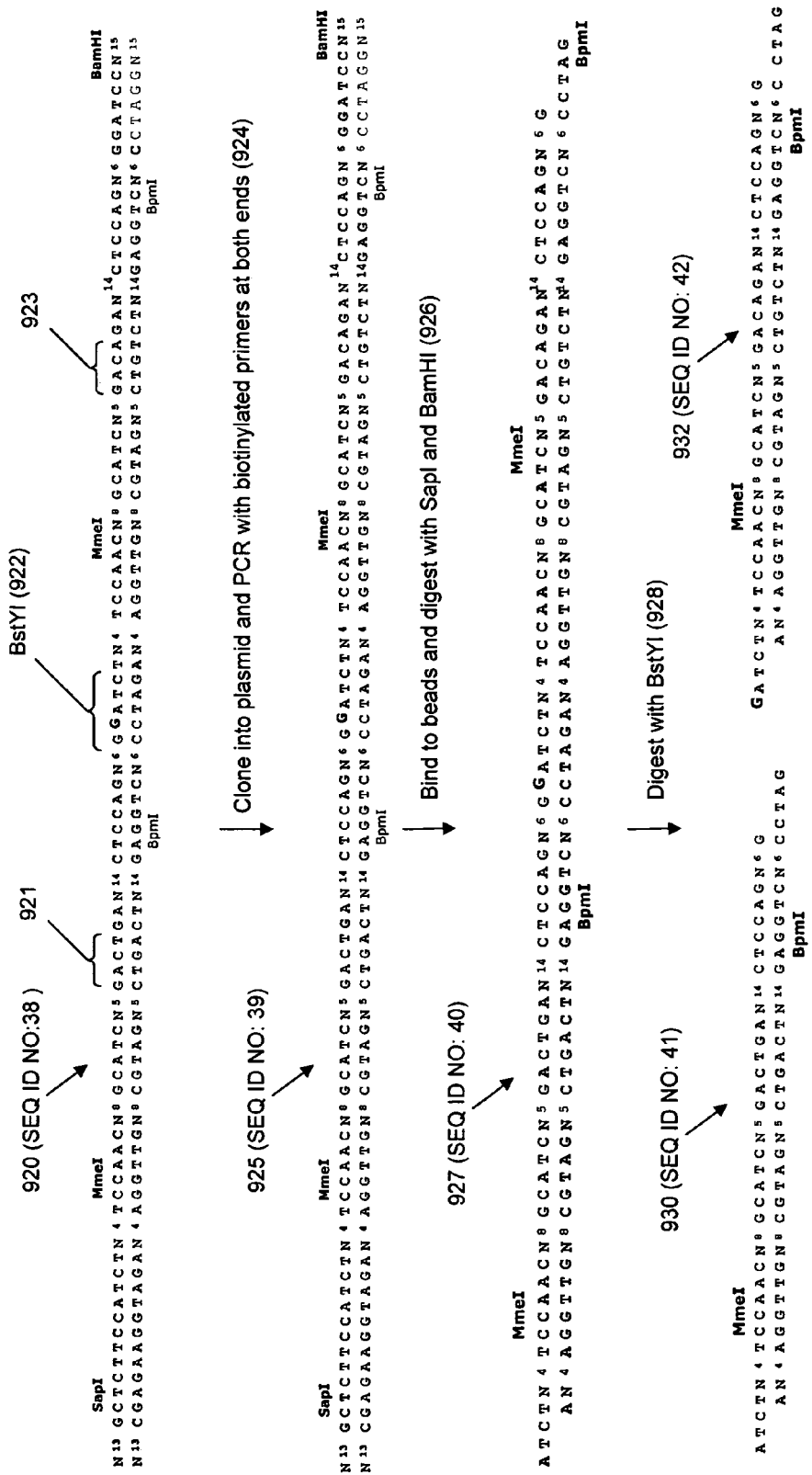

In this example, a scheme for constructing an arbitrarily large set of binary tags of the form "$[GACX]_n$," is described, where X may be A, G, C, or T, and n is the number of subunits in the tags. (Below, "GACA", "GACG", "GACC", and "GACT" are sometimes referred to as the binary A, G, C, and T words, respectively). The scheme, which follows the general approach given above, is described in FIGS. 9A-9E. In accordance with one aspect of the invention, the scheme provides a method of producing equimolar amounts of member tags of a set. This feature is accomplished by generating and isolating a structure that contains two members of the set and then cleaving it into two parts that necessarily are present in equimolar amounts (A & T or G & C, as shown in FIG. 9C). Turning to FIG. 9A, constructs of the form (900) (SEQ ID NO: 32) are synthesized that at position (902) (indicated by the basepair "X/X") include basepairs A/T, T/A, G/C, and C/G. Positions with "N" can be any nucleotide, i.e. A, C, G, or T, or its complement. Each such construct is amplified by PCR (904) using a biotinylated forward (i.e. "SapI end") primer, after which the resulting amplicon (903) (SEQ ID NO: 33) is captured on streptavidinated beads, washed, and digested with SapI (906) to produce released fragment (907) (SEQ ID NO: 34), which is used in a ligation reaction described below. Separately, as illustrated in FIG. 9B, constructs (900) are treated as follows. Each such construct is amplified by PCR (910) using a biotinylated reverse (i.e. "BamHI end") primer, after which the resulting amplicon (911)(SEQ ID NO: 35) is captured on streptavidinated beads, washed, and digested with BamHI (912) to produce released fragment (913). Fragment (913)(SEQ ID NO: 36) is treated (914) with a DNA polymerase in the presence of dGTP to fill-in by one nucleotide the overhang produced by BamHI cleavage to form fragment (915)(SEQ ID NO: 37). Fragments (915) and (907) are then ligated together to produce construct (920)(SEQ ID NO: 38) that contains a binary A word (921) and a binary T word (923) in its top strand. Similar constructs are formed containing a binary G word and a binary C word. Such constructs are cloned into plasmids. Copies are made by amplifying (924) the constructs by PCR using primers that are both biotinylated, capturing the resulting amplicon (SEQ ID NO: 39) on streptavidinated beads, and digesting with BamHI and SapI (926) to release fragment (927)(SEQ ID NO: 40), which, in turn, is digested with BstYI (928) to give equimolar amounts of fragments (930)(SEQ ID NO: 41) and (932)(SEQ ID NO: 42).

Figure 9D:
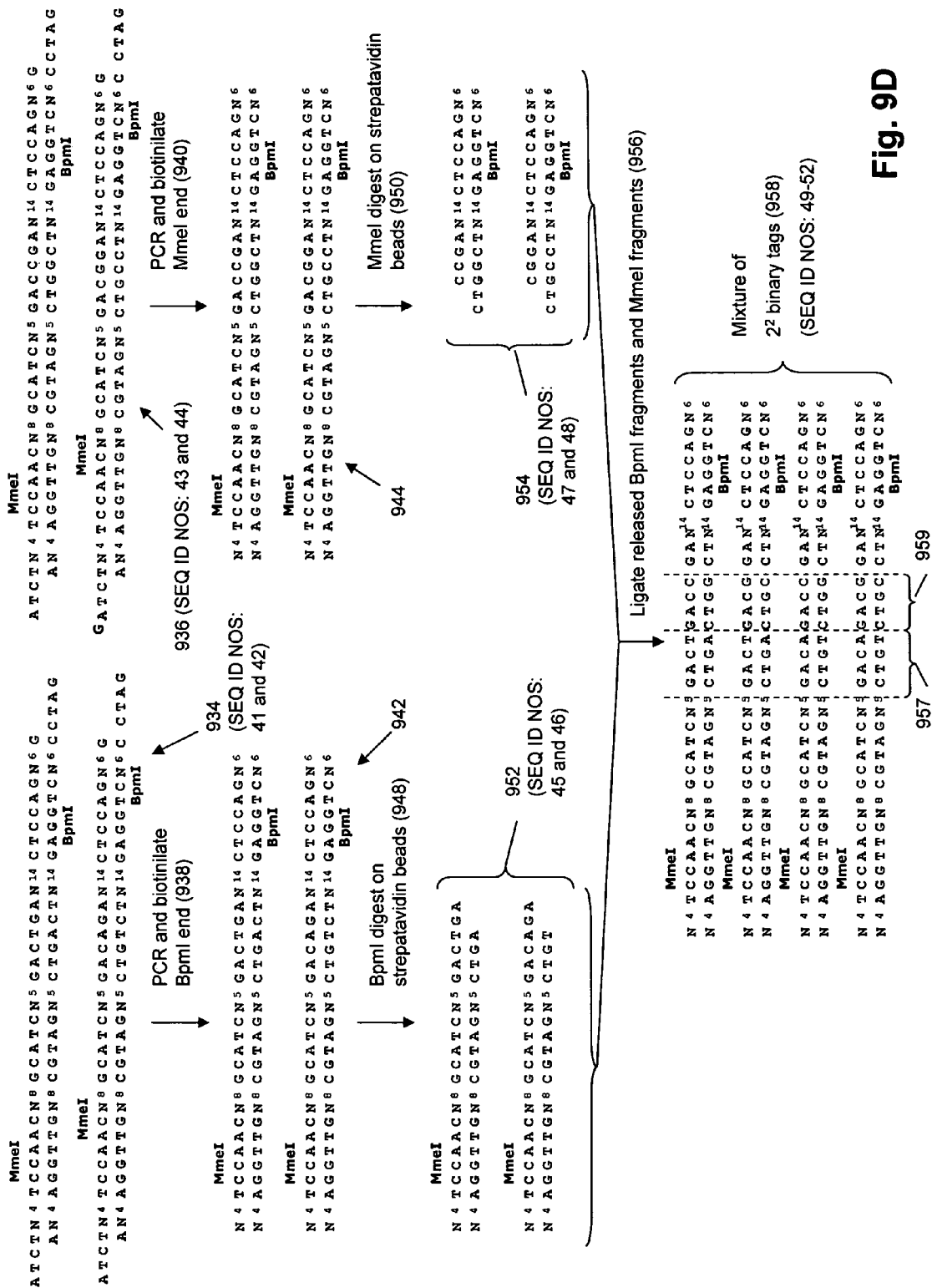
Figure 9E:
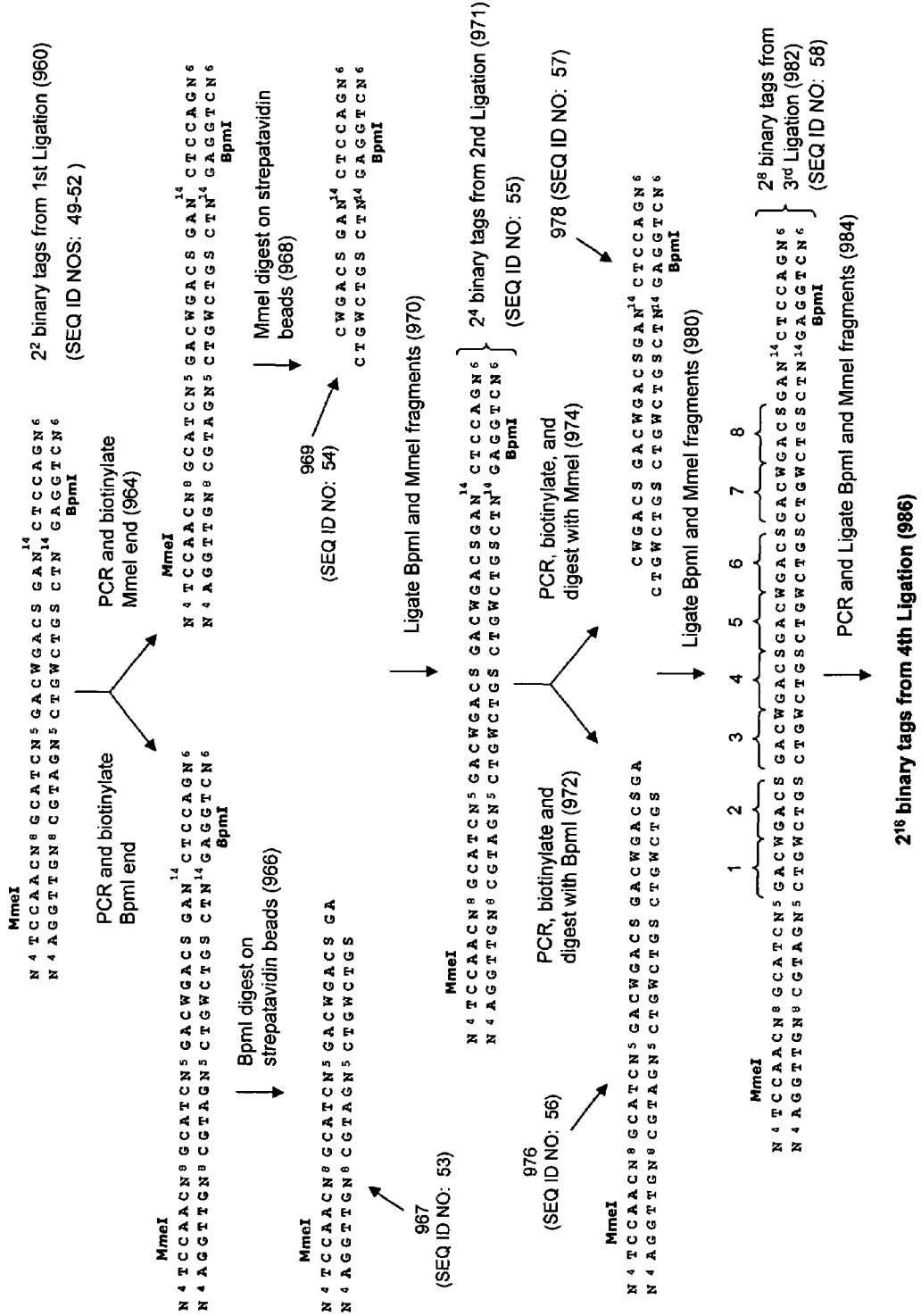

The equimolar mixtures of the fragments containing binary A words and T words (934)(SEQ ID NOS: 41 and 42) and containing binary C words and G words (936)(SEQ ID NOS: 43 and 44) are treated in parallel as shown in FIG. 9D. Equimolar fragment mixture (934) is amplified by PCR using a biotinylated reverse primer (i.e. "BpmI end primer") to form mixture of amplicons (942), which are then captured on streptavidinated beads and digested with BpmI (948) to give released fragments (952)(SEQ ID NOS: 45 and 46). Similarly, equimolar fragment mixture (936) is amplified by PCR using a biotinylated forward primer (i.e. "MmeI end primer") to form mixture of amplicons (944), which are then captured on streptavidinated beads and digested with MmeI (950) to give released fragments (954)(SEQ ID NOS: 47 and 48). These fragments and fragments (952) are ligated (956) to generate mixture (958)(SEQ ID NOS: 49 through 52) of 22 binary tags, with the locations of binary words indicated (957 and 959). Portions of the ligation products from the first (or previous) cycle (960) are treated in parallel (962 and 964) (as above) to form biotinylated amplicons that are separately captured and digested with BpmI (966) and MmeI (968), respectively. The size of the set of binary tags is increased by further cycles of amplification, capture, digestion, and ligation, as illustrated in FIG. 9E. The released fragments (967 (SEQ ID NO: 53) AND 969 (SEQ ID NO: 54) are then ligated (970) to form a mixture (971)(SEQ ID NO: 55) of constructs containing $2^4$ four-word binary tags. Portions of the ligation products from this reaction are again treated in parallel with steps of PCR amplification, capture, and digestion with BpmI (972) and MmeI (974) to form fragments (976)(SEQ ID NO: 56) and fragments (978)(SEQ ID NO: 57), respectively. These fragments are ligated (980) to form a mixture of $2^8$ 8-word binary tags (982)(SEQ ID NO: 58). A further cycle (984) of amplification, capture, digestion, and ligation gives a mixture of 216 16-word binary tags (986).

EXAMPLE III

Sensitivity of Sorting by Sequence

In this example, the use of the sensitivity of the sorting-by-sequence technique for counting tags was tested. A mixture of four polynucleotides was produced. Each polynucleotide shared a common sequence at position 1 of the base to be sorted, followed by A, G, C or T at position 2, and again a common base at position 3. Each polynucleotide was tagged with one of four different composite tags. After incorporation of a biotinylated base at the sorting site (position 2), polynucleotides were selected by streptavidin and the metric tags embedded within the composite tags released by cleavage with Kpn I, which, in turn, yielded metric tags of 29, 33, 34 or 35 base pairs long, respectively. Detection was performed by direct visualization by fluorescent labeling, without PCR, of the sorted polynucleotides after electrophoresis.

Figure 10A:
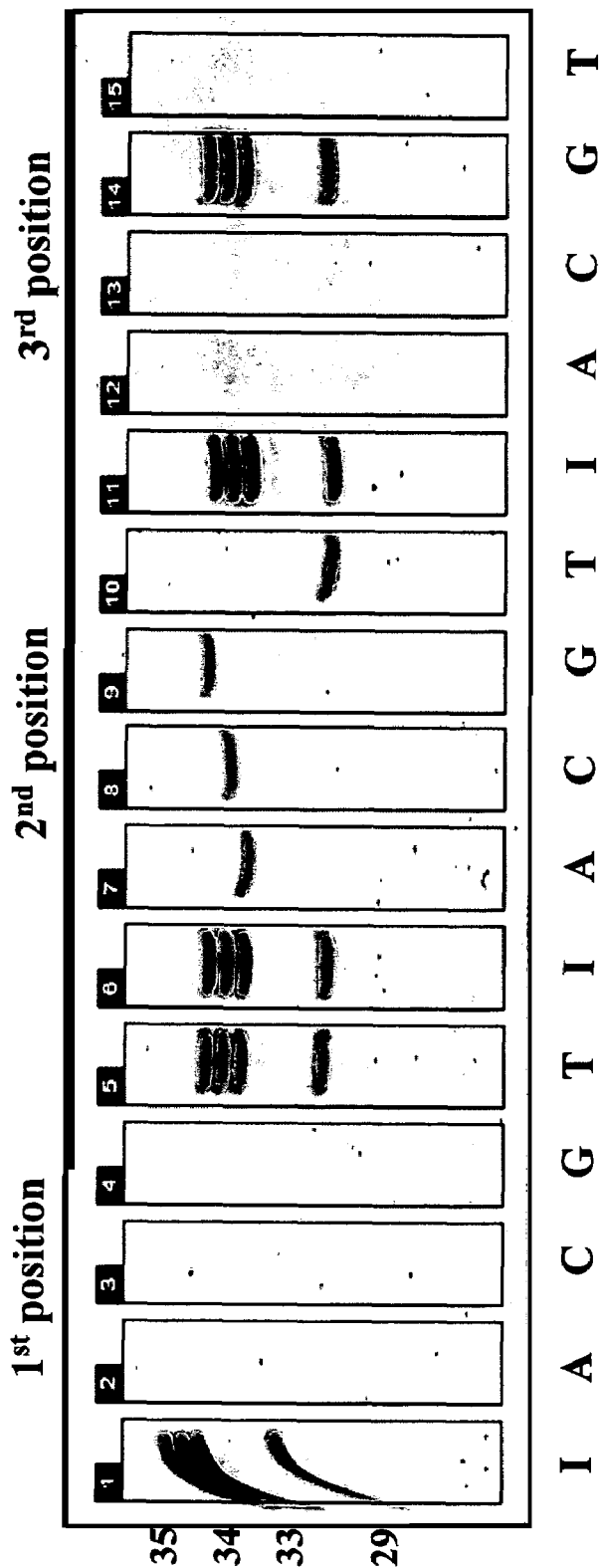
FIG. 10A shows data demonstrating the use of the sorting by sequence technique for generating successively less complex mixtures of nucleic acids.

The polynucleotides were prepared by PCR from the plasmids containing the appropriate composite tags. Table III shows the designations for these along with the identities of $1^{st}$, $2^{nd}$ and $3^{rd}$ bases that were sorted and the associated metric tag length. These bases were exposed for sorting by Bcc I digestion. In the first set (#1, 2, 3 and 4), all four polynucleotides have one base "A" overhanging at the 5' end with different sizes of metric tag. In the second set (#5, 6, 7 and 8), all four polynucleotides have different base overhanging at the 5' end, again with different sizes of metric tag. In the third set (#9, 10, 11 and 12), all four polynucleotides have same one base "C" overhanging at the 5' end with different size of metric tag. Each polynucleotide was fluorescently labeled at the 5' end of the metric tag side. Each polynucleotide was digested, mixed and sorted by incorporating a biotinylated dNTP, and metric tags were released by KpnI digestion after sorting. The released metric tags were separated by polyacrylamide gel electrophoresis on a 20% gel in a urea buffer. FIG. 10A contains an image of the electrophoretically separated metric tags. The results show that all are sorted together at positions 1 and 3, and that all separately at position 2, as predicted. The data confirm that incorporation of a biotinylated base at the sorting site can be selected by streptavidin and that metric tags released from the sorted sequences can be identified by separation.

TABLE III

| Polynucleotide | $1^{st}$ position | Metric Tag | $2^{nd}$ position | Metric Tag | $3^{rd}$ position | Metric Tag | MT Size (nt) |
|---|---|---|---|---|---|---|---|
| 1 | A | S1T7 | | | | | 29 |
| 2 | A | S1T1 | | | | | 35 |
| 3 | A | S1T2 | | | | | 34 |
| 4 | A | S1T3 | | | | | 33 |
| 5 | | | A | S1T7 | | | 29 |
| 6 | | | C | S1T1 | | | 35 |
| 7 | | | G | S1T2 | | | 34 |
| 8 | | | T | S1T3 | | | 33 |
| 9 | | | | | C | S1T7 | 29 |
| 10 | | | | | C | S1T1 | 35 |
| 11 | | | | | C | S1T2 | 34 |
| 12 | | | | | C | S1T3 | 33 |

The sensitivity of sorting-by-sequence was tested as follows. Two templates, attached to two different metric tags, were mixed together at varying ratios as indicated in the table of FIG. 10B. The desired template was selected by incorporating the appropriate biotinylated dNTP with Sequenase. This mixture was combined with streptavidinated beads, so that biotinylated DNA was bound and non-biotinylated DNA was washed away. Bound DNA was denatured and the released non-biotinylated strand in the supernatant was used as template in a PCR reaction using a TAMRA-labeled primer. The PCR products were digested with Kpn I to release metric tags of 30 and 32 bases. The gel image of FIG. 10B shows the separated metric tags after PAGE. In lane 4, where the ratio of A template: G template was 100:1, the band containing strands captured via biotinylated dC had substantially the same density as that of the unselected template, suggesting a background of 1%.

DEFINITIONS

Terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRS. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but be not limited to, buffering agents to maintain pH at a selected level during a reaction, salts, co-factors, scavengers, and the like.

"Binding compound" means a molecule to which a molecular tag can be directly or indirectly attached that is capable of specifically binding to an analyte, usually to form a stable complex. Binding compounds include, but are not limited to, antibodies, antibody binding compositions, peptides, proteins, nucleic acids, and organic molecules.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length.

"Genetic variant" means a substitution, inversion, insertion, or deletion of one or more nucleotides at genetic locus, or a translocation of DNA from one genetic locus to another genetic locus. In one aspect, genetic variant means an alternative nucleotide sequence at a genetic locus that may be present in a population of individuals and that includes nucleotide substitutions, insertions, and deletions with respect to other members of the population. In another aspect, insertions or deletions at a genetic locus comprises the addition or the absence of from 1 to 10 nucleotides at such locus, in comparison with the same locus in another individual of a population.

"Hybridization" or "hybridizing" or "annealing" refers to the process in which two single-stranded polynucleotides bind non-covalently to form a stable double-stranded polynucleotide or in which one single-stranded polynucleotide and one double-stranded polynucleotide bind non-covalently to form a stable triple-stranded structure. The resulting double-stranded or triple-stranded polynucleotide is sometimes referred to as a "duplex" or "triplex," respectively. For the formation duplexes, "hybridization conditions" will typically include salt concentrations of less than about 1 M, more usually less than about 500 mM and less than about 200 mM. Hybridization temperatures can be as low as 5° C., but are typically greater than 22° C., more typically greater than about 30° C., and preferably in excess of about 37° C., although when hybridization is required as well as the operation of an enzyme, frequently there is a trade-off in selecting reaction conditions between the optimal temperature for enzyme activity and hybridization. Preferably, when no such trade-offs are necessary, hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes. In one aspect of the present invention, kits also include in one aspect circularizing adaptors for enumerating particular DNA fragments, such as selected regions of the ErbB2 gene, or the like. Such kits also include one or more type IIs restriction endonucleases, such as double cleavage type IIs restriction endonucleases. Such kits further include reagents for internal and external standards, such as a second circularizing adaptor for an internal standard fragment indigenous to a specimen, and/ or such as a known DNA fragment for an external standard that has a known concentration (and therefore, a known number in a predetermined reaction volume). In another aspect, kits also include padlock probes specific for selected regions of particular genes as described above, probe extension reagents, probe ligation reagents, one or more nucleases, and components for capture, primer extension, and extension product amplification. In still another aspect, kits also include ligation probes comprising a first component and a second component, ligation reagents, reagents for amplifying and capturing ligation products.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27:875-881 (1999); Higgins et al, Methods in Enzymology, 68:50-71 (1979); Engler et al, The Enzymes, 15:3-29 (1982); and Namsaraev, U.S. patent publication 2004/0110213.

"Microarray" refers to a solid phase support having a planar or substantially planar surface, which carries an array of nucleic acids, each member of the array comprising identical copies of an oligonucleotide or polynucleotide immobilized to a spatially defined region or site, sometimes referred to as an "element," which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2:404-410 (1998); Nature Genetics Supplement, 21:1-60 (1999). Microarrays having elements of any desired sequence are available commercially in several formats, and are described in the following references that are incorporated here by reference: Fodor et al, U.S. Pat. Nos. 5,744,305; 6,346,413; 5,445,934; 6,610,482; 5,800,992; 6,355,432; Cerrina et al, U.S. Pat. No. 6,375,903; Pfleiderer et al, U.S. Pat. Nos. 6,750,335; 5,763,599; Caren et al, U.S. Pat. No. 6,323,043; Beaucage, Curr. Med. Chem., 8:1213-1244 (2001); Heller, Ann. Rev. Biomed. Eng., 4:129-153 (2002); Hughes et al, Nature Biotechnology, 19:342-346 (2001); and the like. As used herein, "random microarray" refers to a microarray whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like. Likewise, after formation, microbeads, or oligonucleotides thereof, in a random array may be identified in a variety of ways, including by optical labels, e.g. fluorescent dye ratios or quantum dots, shape, sequence analysis, or the like.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6:855-870 (1996); Mesmaeker et al, Current Opinion in Structural Biology, 5:343-355 (1995); and the like. Exemplary types of polynucleotides that are capable of enhancing duplex stability include oligonucleotide N3'→>P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide tag" means an oligonucleotide that is attached to a polynucleotide and is used to identify and/or track the polynucleotide in a reaction. Usually, an oligonucleotide tag is attached to the 3'- or 5'-end of a polynucleotide to form a linear conjugate, sometime referred to herein as a "tagged polynucleotide," or equivalently, an "oligonucleotide tag-polynucleotide conjugate," or "tag-polynucleotide conjugate," or similar term. Oligonucleotide tags may vary widely in size and compositions; the following references provide guidance for selecting sets of oligonucleotide tags appropriate for particular embodiments: Brenner, U.S. Pat. No. 5,635, 400; Brenner et al, Proc. Natl. Acad. Sci., 97:1665-1670 (2000); Church et al, European patent publication 0 303 459; Shoemaker et al, Nature Genetics, 14:450-456 (1996); Morris et al, European patent publication 0799897A1; Wallace, U.S. Pat. No. 5,981,179; and the like. Lengths of oligonucleotide tags can vary widely, and the selection of a particular lengths depend on several factors including, without limitation, whether the oligonucleotide tags are employed primarily in hybridization reactions or primarily in enzymatic reactions, whether they are labeled, whether such labeling is direct or indirect, the number of distinguishable oligonucleotide tags required, and the like. In one aspect, oligonucleotide tags can each have a length within a range of from 2 to 36 nucleotides, or from 4 to 30 nucleotides, or from 8 to 20 nucleotides, respectively. In one aspect, oligonucleotide tags are used in sets, or repertoires, wherein each oligonucleotide tag of the set has a unique nucleotide sequence. In some embodiments, particularly where oligonucleotide tags are used to sort polynucleotides, or where they are identified by specific hybridization, each oligonucleotide tag of such a set has a melting temperature that is substantially the same as that of every other member of the same set; however, members of such a set have sequences that differ maximally from those of other members of the set. In such aspects, the melting temperatures of oligonucleotide tags within a set are within $10°$ C. of one another; in another embodiment, they are within $5°$ C. of one another; and in another embodiment, they are within $2°$ C. of one another. In another aspect, oligonucleotide tags are members of a mutually discriminable set; that is, oligonucleotide tags of such a set differ maximally from one another by some characteristic, such as sequence, melting temperature, or the like. The size of mutually discriminable sets of oligonucleotide tags may vary widely. Such a set of oligonucleotide tags may have a size in the range of from several tens to many thousands, or even millions, e.g. 50 to $1.6 \times 10^6$. In another embodiment, such a size is in the range of from 200 to 40,000; or from 1000 to 40,000; or from 1000 to 10,000. In another aspect of the invention, oligonucleotide tags comprise a collection of subunits, usually, but not necessarily, aligned in end-to-end fashion as a concatenate, such as described by Brenner et al, Proc. Natl. Acad. Sci., 97:1665-1670 (2000). In such concatenates, oligonucleotide subunits, or words, can be selected from a set of subunits with the properties of mutual discriminability and substantially equivalent melting temperature. Constructing oligonucleotide tags from a plurality of oligonucleotide subunits permits the convenient and inexpensive formation by combinatorial synthesis of very large sets of oligonucleotide tags, e.g. as described by Brenner et al, Proc. Natl. Acad. Sci., 97:1665-1670 (2000). Also, the use of oligonucleotide subunits permits enzymatic synthesis and/or attachment of oligonucleotide tags to polynucleotides, e.g. as described below and in Brenner and Williams, U.S. patent publication 2003/0049616. In one aspect, oligonucleotide tags comprise a plurality of oligonucleotide subunits. Such subunits may vary widely in length. In one aspect, the length of oligonucleotide subunits is in the range of from 2 to 18 nucleotides; in another aspect, the length of oligonucleotide subunits is in the range of from 2 to 8 nucleotides; and in another aspect the length of oligonucleotide subunits is in the range of from 2 to 5 nucleotides. A plurality of oligonucleotide subunits making up an oligonucleotide tag may also vary widely depending on their application. In one aspect, such plurality is a number in the range of 2 to 10; and in another aspect, such plurality is a number in the range of from 2 to 6. The size of a set of oligonucleotide subunits is usually smaller than the size of a set of oligonucleotide tags. Usually, a set of oligonucleotide subunits has a size in the range of from 2 to 20; or in another embodiment, from 2 to 10; or in another embodiment, from 4 to 8. It is clear to one of ordinary skill in the art that for subunits only two nucleotides in length that the size of a set of subunits would be smaller than that of subunits having greater lengths. In some embodiments where oligonucleotide tags are synthesized combinatorially, such tags comprise a sequence of subunits aligned linearly such that for a randomly selected tag there is an equal probability that any subunit will be at any given position. In such embodiments, an oligonucleotide tag may contain more than one copy of the same kind of subunit. In other embodiments, an oligonucleotide tag may comprise a plurality of subunits such that no two subunits of the same tag are of the same kind. In this latter type of oligonucleotide tag, the subunits may or may not be arranged as a concatenate.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature $>90°$ C., primers annealed at a temperature in the range $50$-$75°$ C., and primers extended at a temperature in the range $72$-$78°$ C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30:1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273:221-228 (1999) (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: $\beta$3-actin, GAPDH, $\beta_2$-microglobulin, ribosomal RNA, and the like. Techniques for quantitative PCR are well-known to those of ordinary skill in the art, as exemplified in the following references that are incorporated by reference: Freeman et al, Biotechniques, 26:112-126 (1999); Becker-Andre et al, Nucleic Acids Research, 17:9437-9447 (1989); Zimmerman et al, Biotechniques, 21:268-279 (1996); Diviacco et al, Gene, 122:3013-3020 (1992); Becker-Andre et al, Nucleic Acids Research, 17:9437-9446 (1989); and the like.

"Polynucleotide" or "oligonucleotide" are used interchangeably and each mean a linear polymer of nucleotide monomers. As used herein, the terms may also refer to double stranded forms. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions, when such analogs are incompatible with enzymatic reactions. Polynucleotides typically range in size from a few monomeric units, e.g. 5→40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Separation profile" in reference to the separation of molecular species, such as a metric tag, means a chart, graph, curve, bar graph, or other representation of signal intensity data versus a parameter related to the molecular species, such as retention time, mass, or the like, that provides a readout, or measure, of the number of molecular species of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular species have different fluorescent labels having distinct emission spectra and data is collected and recorded at multiple wavelengths. In one aspect, released molecular species are separated by differences in electrophoretic mobility to form an electropherogram wherein different molecular species correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular species whose members have electrophoretic mobilities that differ by at least a peak-resolving amount, such quantity depending on several factors well known to those of ordinary skill, including signal detection system, nature of the fluorescent moieties, the diffusion coefficients of the species, the presence or absence of sieving matrices, nature of the electrophoretic apparatus, e.g. presence or absence of channels, length of separation channels, and the like.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and: hydrophobic interactions, and the like, dominate the interaction of the molecules.

As used herein, the term "$T_m$" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. $Tm=81.5+0.41$ (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" usually means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

Notwithstanding the above, "sample" in the context of the present invention also means a subset of a larger set, usually of tags or tag-molecule conjugates, wherein the subset members are picked at random from the larger set.

"Terminator" means a nucleotide that cannot be extended by a nucleic acid polymerase. Typically, a terminator can be incorporated into a primer by a polymerase extension reaction, such that the incorporated nucleotide prevents subsequent incorporation of nucleotides to the primer and thereby halts further polymerase-mediated extension. Terminators for enzymatic incorporation include nucleoside triphosphates that lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose nucleosides, for example. Alternatively, a ribofuranose analog can be used in terminators, such as 2',3'-dideoxy-β-D-ribofuranosyl, β-D-arabinofuranosyl, 3'-deoxy-β-D-arabinofuranosyl, 3'-amino-2',3'-dideoxy-β-D-ribofaranosyl, and 2,3'-dideoxy-3'-fluoro-β-D-ribofuranosyl. A variety of terminators are disclosed in the following references: Chidgeavadze et al., Nucleic Acids Res., 12:1671-1686 (1984); Chidgeavadze et al., FEBS Lett., 183:275-278 (1985); Izuta et al, Nucleosides & Nucleotides, 15:683-692 (1996); and Krayevsky et al, Nucleosides & Nucleotides, 7:613-617 (1988). Nucleotide terminators also include reversible nucleotide terminators, e.g. Metzker et al. Nucleic Acids Res., 22(20):4259 (1994). Terminators may be derivatized with a capture moiety, such as a biotin group, as disclosed by Ju et al, U.S. Pat. No. 5,876,936.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it

APPENDIX I

Sequence-Specific Sorting

Sequence-specific sorting, or sorting by sequence, is a method for sorting polynucleotides from a population based on predetermined sequence characteristics, as disclosed in Brenner, PCT publication WO 2005/080604 and below. In one aspect, the method is carried out by the following steps: (i) extending a primer annealed polynucleotides having predetermined sequence characteristics to incorporate a predetermined terminator having a capture moiety, (ii) capturing polynucleotides having extended primers by a capture agent that specifically binds to the capture moiety, and (iii) melting the captured polynucleotides from the extended primers to form a subpopulation of polynucleotides having the predetermined sequence characteristics.

The method includes sorting polynucleotides based on predetermined sequence characteristics to form subpopulations of reduced complexity. In one aspect, such sorting methods are used to analyze populations of uniquely tagged polynucleotides, such as genome fragments. During or at the conclusion of repeated steps of sorting in accordance with the invention, the tags may be replicated, labeled and hybridized to a solid phase support, such as a microarray, to provide a simultaneous readout of sequence information from the polynucleotides. As described more fully below, predetermined sequence characteristics include, but are not limited to, a unique sequence region at a particular locus, a series of single nucleotide polymorphisms (SNPs) at a series of loci, or the like. In one aspect, such sorting of uniquely tagged polynucleotides allows massively parallel operations, such as simultaneously sequencing, genotyping, or haplotyping many thousands of genomic DNA fragments from different genomes.

Figure 11A:
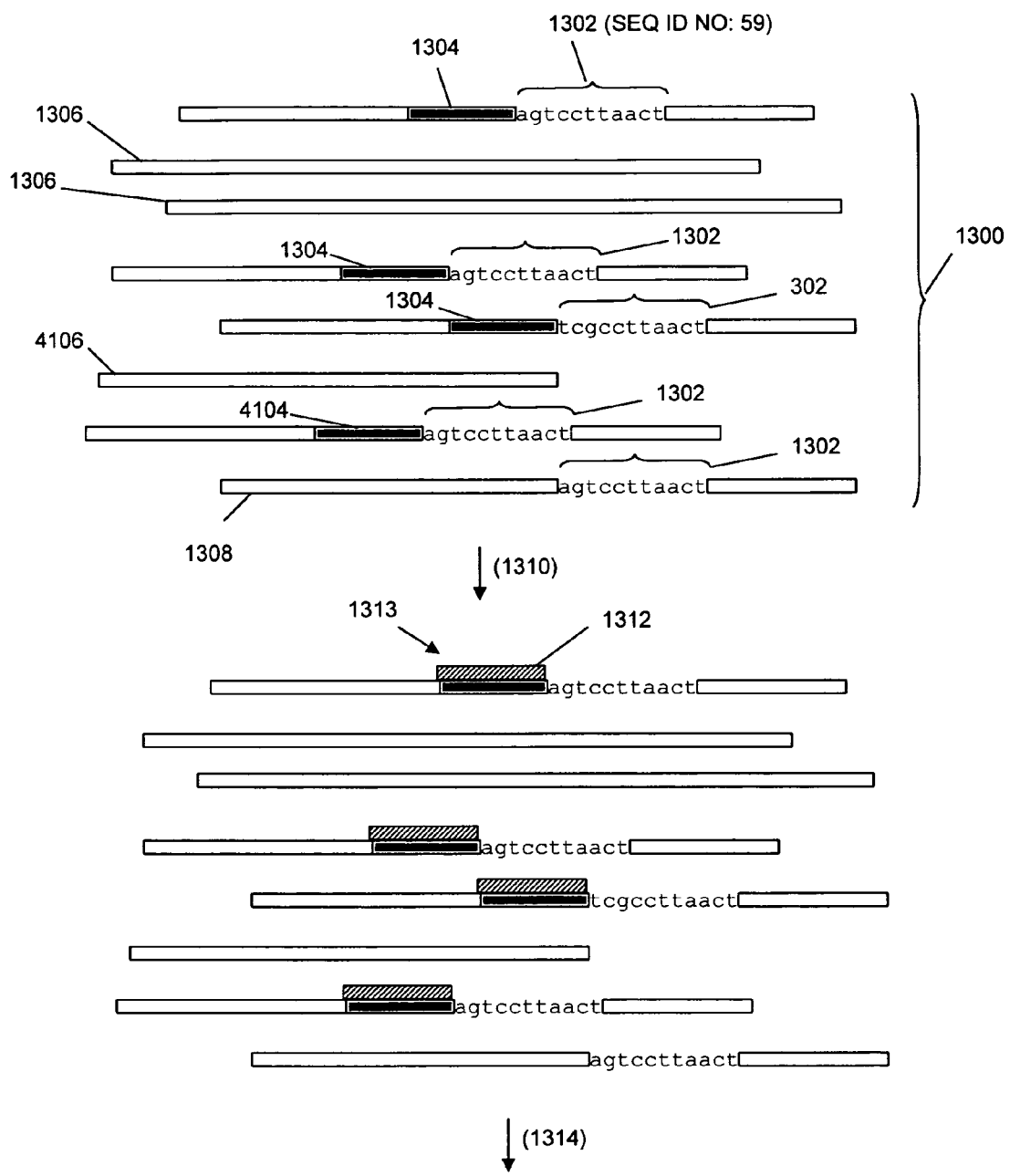
FIGS. 11A-11E illustrate a method of selecting particular fragments by common sequence elements.
Figure 11B:
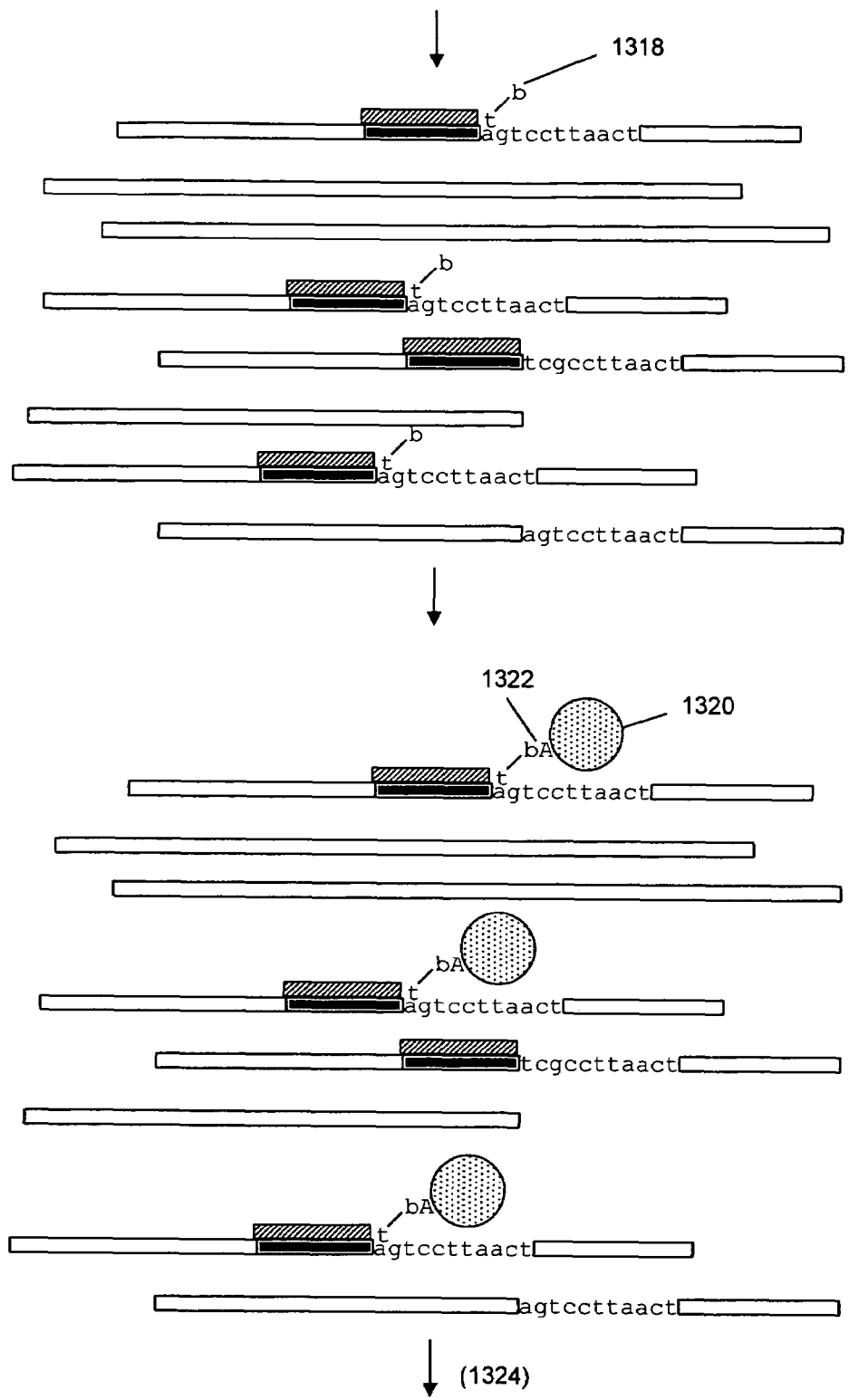
Figure 11C:
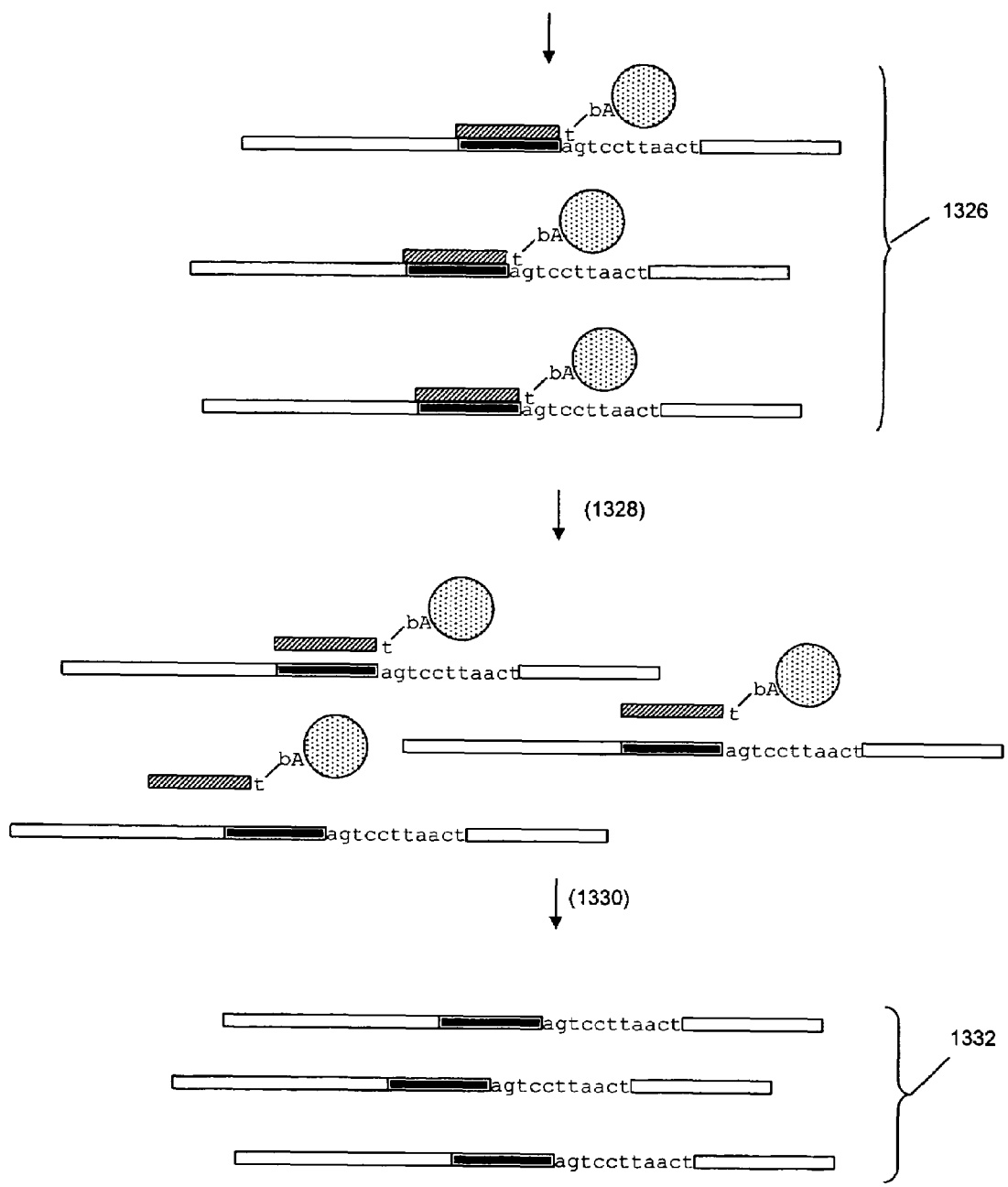

One aspect of the complexity-reducing method of the invention is illustrated in FIGS. 11A-11C. Population of polynucleotides (1300), sometimes referred to herein as a parent population, includes sequences having a known sequence region that may be used as a primer binding site (1304) that is immediately adjacent to (and upstream of) a region (1302)(SEQ ID NO: 59) that may contain one or more SNPs. Primer binding site (1304) has the same, or substantially the same, sequence whenever it is present. That is, there may be differences in the sequences among the primer binding sites (1304) in a population, but the primer selected for the site must anneal and be extended by the extension method employed, e.g. DNA polymerase extension. Primer binding site (1304) is an example of a predetermined sequence characteristic of polynucleotides in population (1300). Parent population (1300) also contains polynucleotides that do not contain either a primer binding site (1304) or polymorphic region (1302). In one aspect, the invention provides a method for isolating sequences from population (1300) that have primer binding sites (1304) and polymorphic regions (1302). This is accomplished by annealing (1310) primers (1312) to polynucleotides having primer binding sites (1304) to form primer-polynucleotide duplexes (1313). After primers (1312) are annealed, they are extended to incorporate a predetermined terminator having a capture moiety. Extension may be effected by polymerase activity, chemical or enzymatic ligation, or combinations of both. A terminator is incorporated so that successive incorporations (or at least uncontrolled successive incorporations) are prevented.

This step of extension may also be referred to as "template-dependent extension" to mean a process of extending a primer on a template nucleic acid that produces an extension product, i.e. an oligonucleotide that comprises the primer plus one or more nucleotides, that is complementary to the template nucleic acid. As noted above, template-dependent extension may be carried out several ways, including chemical ligation, enzymatic ligation, enzymatic polymerization, or the like. Enzymatic extensions are preferred because the requirement for enzymatic recognition increases the specificity of the reaction. In one aspect, such extension is carried out using a polymerase in conventional reaction, wherein a DNA polymerase extends primer (1312) in the presence of at least one terminator labeled with a capture moiety. Depending on the embodiment, there may be from one to four terminators (so that synthesis is terminated at any one or at all or at any subset of the four natural nucleotides). For example, if only a single capture moiety is employed, e.g. biotin, extension may take place in four separate reactions, wherein each reaction has a different terminator, e.g. biotinylated dideoxyadenosine triphosphate, biotinylated dideoxycytidine triphosphate, and so on. On the other hand, if four different capture moieties are employed, then four terminators may be used in a single reaction. Preferably, the terminators are dideoxynucleoside triphosphates. Such terminators are available with several different capture moieties, e.g. biotin, fluorescein, dinitrophenol, digoxigenin, and the like (Perkin Elmer Lifesciences). Preferably, the terminators employed are biotinylated dideoxynucleoside triphosphates (biotin-ddNTPs), whose use in sequencing reactions is described by Ju et al, U.S. Pat. No. 5,876,936, which is incorporated by reference. In one aspect of the invention, four separate reactions are carried out, each reaction employing only one of the four terminators, biotin-ddATP, biotin-ddCTP, biotin-ddGTP, or biotin-ddTTP. In further preference, in such reactions, the ddNTPs without capture moieties are also included to minimize misincorporation.

As illustrated in FIG. 11B, primer (1312) is extended to incorporate a biotinylated dideoxythymidine (1318), after which primer-polynucleotide duplexes having the incorporated biotins are captured with a capture agent, which in this illustration is an avidinated (1322) (or streptavidinated) solid support, such as a microbead (1320). Captured polynucleotides (1326) are separated (1328) and polynucleotides are melted from the extended primers to form (1330) population (1332) that has a lower complexity than that of the parent population (1300). Other capture agents include antibodies, especially monoclonal antibodies, that form specific and strong complexes with capture moieties. Many such antibodies are commercially available that specifically bind to biotin, fluorescein, dinitrophenol, digoxigenin, rhodamine, and the like (e.g. Molecular Probes, Eugene, Oreg.).

Figure 11D:
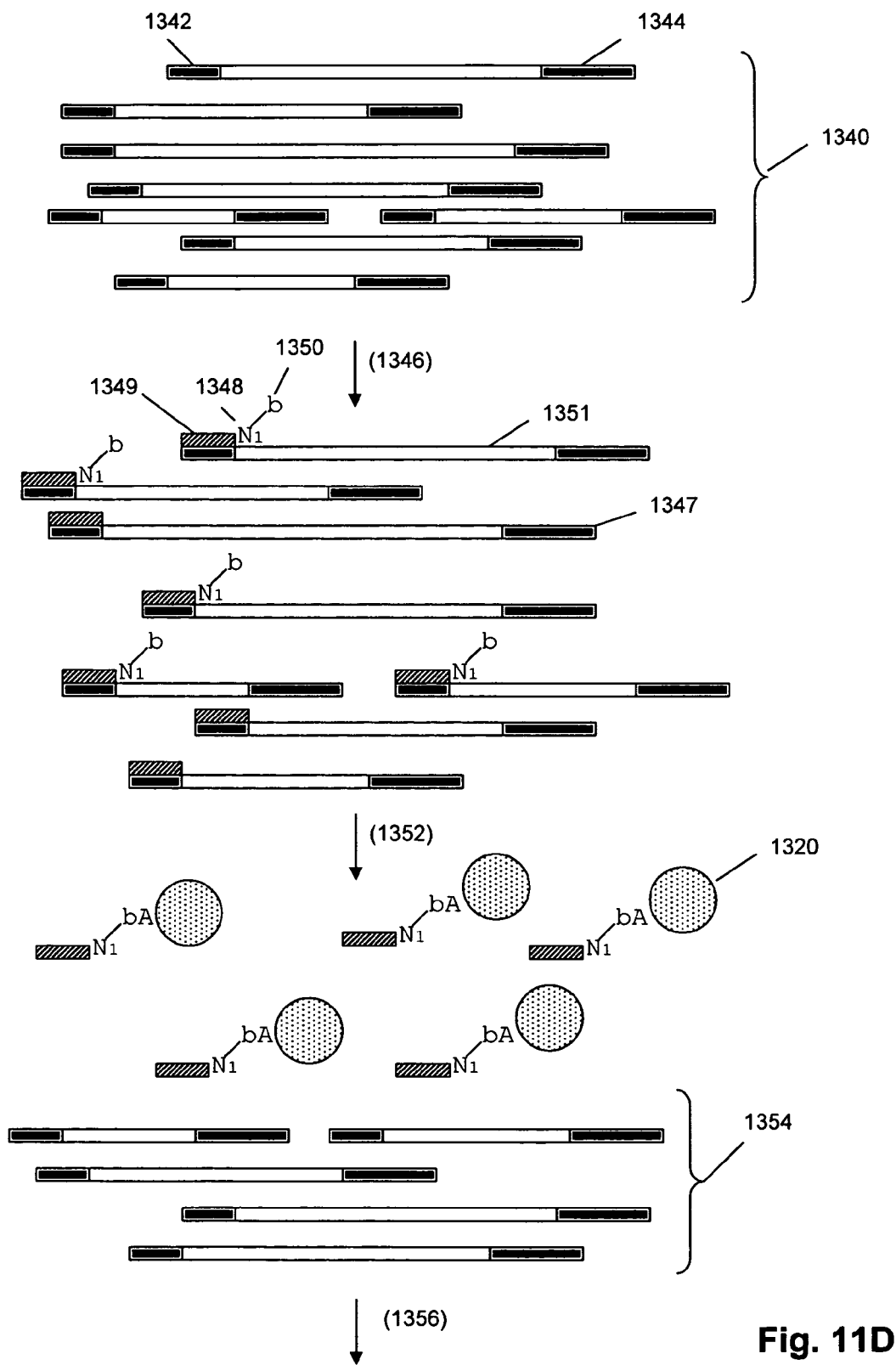
Figure 11E:
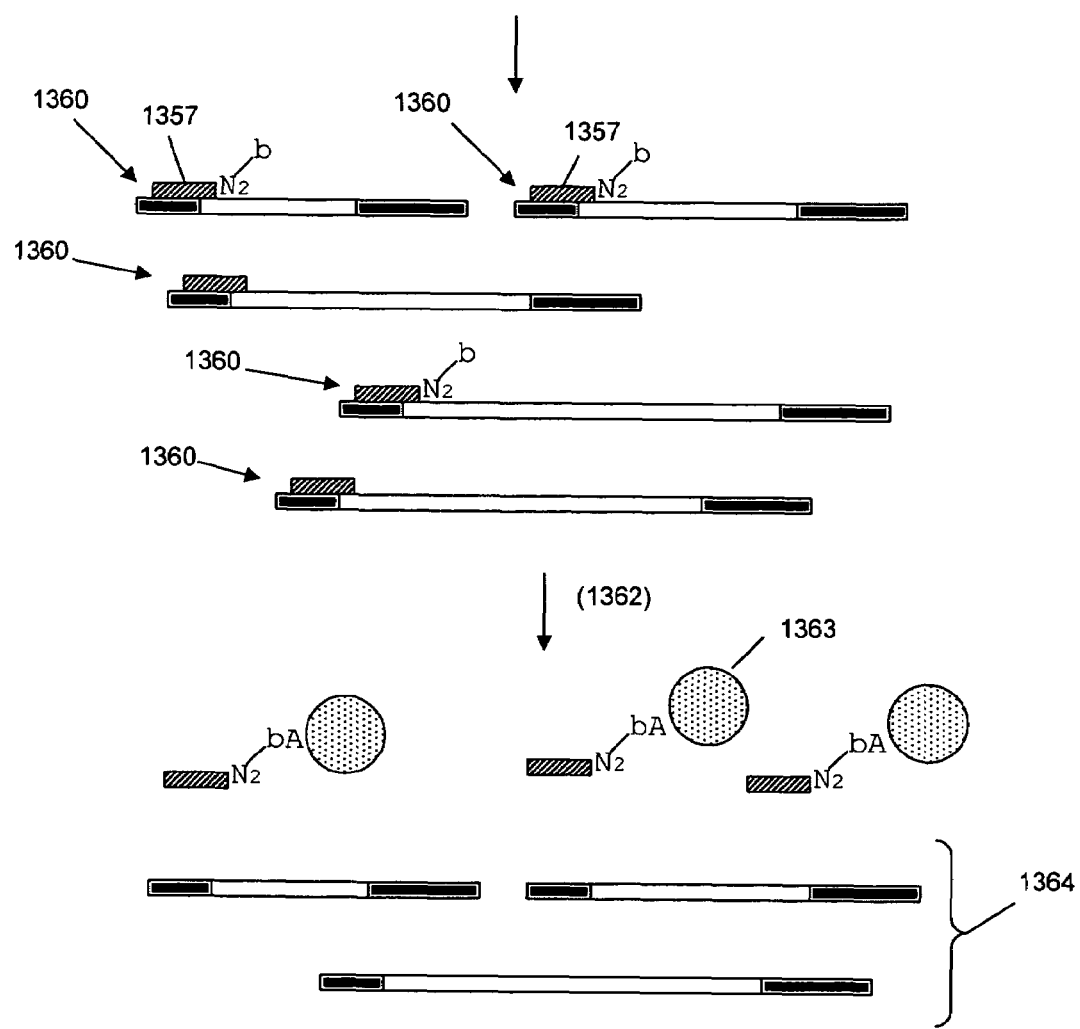

The method also provides a method of carrying out successive selections using a set of overlapping primers of predetermined sequences to isolate a subset of polynucleotides having a common sequence, i.e. a predetermined sequence characteristic. By way of example, population (1340) of FIG. 11D is formed by digesting a genome or large DNA fragment with one or more restriction endonucleases followed by the ligation of adaptors (1342) and (1344), e.g. as may be carried out in a conventional AFLP reactions, U.S. Pat. No. 6,045,994, which is incorporated herein by reference. Primers (1349) are annealed (1346) to polynucleotides (1351) and extended, for example, by a DNA polymerase to incorporate biotinylated (1350) dideoxynucleotide $N_1$ (1348). After capture (1352) with streptavidinated microbeads (1320), selected polynucleotides are separated from primer-polynucleotide duplexes that were not extended (e.g. primer-polynucleotide duplex (1347)) and melted to give population (1354). Second primers (1357) are selected so that when they anneal they basepair with the first nucleotide of the template polynucleotide. That is, their sequence is selected so that they anneal to a binding site that is shifted (1360) one base into the polynucleotide, or one base downstream, relative to the binding site of the previous primer. That is, in one embodiment, the three-prime most nucleotide of second primers (1357) is $N_1$. In accordance with the invention, primers may be selected that have binding sites that are shifted downstream by more than one base, e.g. two bases. Second primers (1357) are extended with a second terminator (1358) and are captured by microbeads (1363) having an appropriate capture agent to give selected population (1364). Successive cycles of annealing primers, extension, capture, and melting may be carried out with a set of primers that permits the isolation of a subpopulation of polynucleotides that all have the same sequence at a region adjacent to a predetermined restriction site. Preferably, after each cycle the selected polynucleotides are amplified to increase the quantity of material for subsequent reactions. In one aspect, amplification is carried out by a conventional linear amplification reaction using a primer that binds to one of the flanking adaptors and a high fidelity DNA polymerase. The number of amplification cycles may be in the range of from 1 to 10, and more preferably, in the range of from 4 to 8. Preferably, the same number of amplification cycles is carried out in each cycle of extension, capturing, and melting.

Advancing Along a Template by "Outer Cycles" of Stepwise Cleavage

The above selection methods may be used in conjunction with additional methods for advancing the selection process along a template, which allows sequencing and/or the analysis of longer sections of template sequence. A method for advancing a template makes use of type IIs restriction endonucleases, e.g. Sfa NI (5'-GCATC(5/9)), and is similar to the process of "double stepping" disclosed in U.S. Pat. No. 5,599,675, which is incorporated herein by reference. "Outer cycle" refers to the use of a type IIs restriction enzyme to shorten a template (or population of templates) in order to provide multiple starting points for sequence-based selection, as described above. In one aspect, the above selection methods may be used to isolate fragments from the same locus of multiple genomes, after which multiple outer cycle steps, e.g. K steps, are implemented to generated K templates, each one successively shorter (by the "step" size, e.g. 1-20 nucleotides) than the one generated in a previous iteration of the outer cycle. Preferably, each of these successively shortened templates is in a separate reaction mixture, so that "inner" cycles of primer extensions and sortings can be implemented of the shortened templates separately.

In another aspect, an outer cycle is implemented on a mixture of fragments from multiple loci of each of multiple genomes. In this aspect, the primer employed in the extension reaction (i.e. the inner cycle) contains nucleotides at its 3' end that anneal specifically to a particular locus, and primers for each locus are added successively and a selection is made prior to the next addition of primers for the next locus.

Assume that starting material has the following form (SEQ ID NO: 1) (where the biotin is optional):

```
         biotin-NN . . . NNGCATCAAAAGATCNN . . .
                NN . . . NNCGTAGTTTTCTAGNN . . .
``` and that after cleavage with Sfa NI the following two fragments are formed (SEQ ID NO: 2):

```
biotin-NN . . . NNGCATCAAAAG        pATCNN . . .
         NN . . . NNCGTAGTTTTCTAGNp           N . . .
``` where "p" designates a 5' phosphate group. The biotinylated fragments are conveniently removed using conventional techniques. The remaining fragments are treated with a DNA polymerase in the presence of all four dideoxynucleoside triphosphates to create end on the lower strand that cannot be ligated:

```
              pATCN  NN . . .
                 N_{dd}NN . . .
``` where "$N_{dd}$" represents an added dideoxynucleotide. To these ends are ligated adaptors of the following form (SEQ ID NO: 3):

```
       N*N*N*NN . . . NNNGCATCAAAA
        N N N NN . . . NNNCGTAGTTTTNNN
``` where "N*" represents a nucleotide having a nuclease-resistant linkage, e.g. a phosphorothioate. The specificity of the ligation reaction is not crucial; it is important merely to link the "top" strands together, preserving sequence. After ligation the following structure is obtained (SEQ ID NO: 4):

```
    N*N*N*NN . . . NNNGCATCAAAAATCN  N . . .
     N N N NN . . . NNNCGTAGTTTTNNNN_{dd}N . . .
```

The bottom strand is then destroyed by digesting with T7 exonuclease 6, λ exonuclease, or like enzyme. An aliquot of the remaining strand may then be amplified using a first primer of the form:

```
         5'-biotin-NN . . . GCATCAAAA
``` and a second primer containing a T7 polymerase recognition site. This material can be used to re-enter the outer cycle. Another aliquot is amplified with a non-biotinylated primer (5'-NN . . . GCATCAAAA) and a primer containing a T7 polymerase recognition site eventually to produce an excess of single strands, using conventional methods. These strands may be sorted using the above sequence-specific sorting method where "N" (italicized) above is G, A, T, or C in four separate tubes.

The basic outer cycle process may be modified in many details as would be clear to one of ordinary skill in the art. For example, the number of nucleotides removed in an outer cycle may vary widely by selection of different cleaving enzymes and/or by positioning their recognition sites differently in the adaptors. In one aspect, the number of nucleotides removed in one cycle of an outer cycle process is in the range of from 1 to 20; or in another aspect, in the range of from 1 to 12; or in another aspect, in the range of from 1 to 4; or in another aspect, only a single nucleotide is removed in each outer cycle. Likewise, the number of outer cycles carried out in an analysis may vary widely depending on the length or lengths of nucleic acid segments that are examined. In one aspect, the number of cycles carried out is in the range sufficient for analyzing from 10 to 500 nucleotides, or from 10 to 100 nucleotides, or from 10 to 50 nucleotides.

In one aspect of the invention, templates that differ from one or more reference sequences, or haplotypes, are sorted so that they may be more fully analyzed by other sequencing methods, e.g. conventional Sanger sequencing. For example, such reference sequences may correspond to common haplotypes of a locus or loci being examined. By use of outer cycles, actual reagents, e.g. primers, having sequences corresponding to reference sequences need not be generated. If at each extension (or inner) cycle, either each added nucleotide has a different capture moiety, or the nucleotides are added in separate reaction vessels for each different nucleotide. In either case, extensions corresponding to the reference sequences and variants are immediately known simply by selecting the appropriate reaction vessel or capture agents.

What is claimed is:

1. A method of determining a number of target molecules in a sample, the method comprising the steps of:
    (a) providing molecule-tag conjugates each comprising an oligonucleotide tag such that substantially every different molecule of the sample is attached to a different oligonucleotide tag, each oligonucleotide tag comprising a concatenation of subunits selected from a set of subunits, each subunit being a different nucleotide or oligonucleotide and having a position, and the set of subunits having a size of from 2 to 6 members;
    (b) dividing the oligonucleotide tags of the molecule-tag conjugates into aliquots by sorting the oligonucleotide tags according to the identity of a subunit within a first or a successive position; and
    (c) repeating step (b) for at least one aliquot in each successive application of step (b) until at least one aliquot has no oligonucleotide tags that can be separated into aliquots and determining the number of molecules in the sample from the number of times step (b) has been applied.

2. The method of claim 1 wherein said number of molecules in said sample is within a range determined by a first number equal to the size of the subset taken to a power equal to the lowest number of said times said step (b) has been applied to produce an aliquot having no oligonucleotide tags less one and a second number equal to the size of the subset taken to a power equal to the greatest number of times said step (b) has been applied to produce an aliquot having no oligonucleotide tags less one.

3. The method of claim 1 wherein said step (c) is carried out for a plurality of said aliquots in at least one application of said step (b) so that a plurality of aliquots each have no oligonucleotide tags that can be separated into aliquots and wherein said number of molecules in said sample is determined from the numbers of times said step (b) has been applied in each of such aliquots.

4. The method of claim 3 wherein said molecules are polynucleotides and said oligonucleotide tags are binary tags.

5. The method of claim 4 wherein said binary tags each comprise a concatenate of dinucleotide subunits.

6. The method of claim 1 wherein said step of dividing includes the steps of extending a primer annealed to said oligonucleotide tags to incorporate either a first terminator having a capture moiety whenever the first terminator is complementary to a nucleotide of a subunit of a oligonucleotide tag or a second terminator having a capture moiety whenever the second terminator is complementary to a nucleotide of a subunit of a oligonucleotide tag, capturing oligonucleotide tags having primers with a first terminator by a capture agent that specifically binds to the capture moiety and melting the captured oligonucleotide tags to form a first aliquot, capturing oligonucleotide tags having primers with a second terminator by a capture agent that specifically binds to the capture moiety and melting the captured oligonucleotide tags to form a second aliquot.

7. The method of claim 6 wherein said captured oligonucleotide tags are replicated after said step of melting.

8. A method of counting a number of target polynucleotides in a specimen, the method comprising the steps of:
    labeling by sampling each target polynucleotide in the specimen so that substantially every target polynucleotide is associated with a unique oligonucleotide tag, each oligonucleotide tag comprising a sorting tag and an identification tag;
    successively sorting the oligonucleotide tags a number of times by their sorting tags to form one or more separate mixtures; and
    determining the number of different oligonucleotide tags in at least one of the one or more separate mixtures by the identification tags thereof; and
    determining the number of target polynucleotides from the number of successive sortings and the number of different oligonucleotide tags in the one or more separate mixtures.

9. The method of claim 8 wherein said sorting tags are binary tags.

10. The method of claim 9 wherein said binary tags are provided in a number and said identification tags are provided in a number, and wherein the number of binary tags is substantially larger than the number of identification tags.

11. The method of claim 10 wherein said identification tags are metric tags.

12. A method of determining a number of target polynucleotides, the method comprising the steps of:
    providing for each target polynucleotide a plurality of nucleic acid probes specific for the target polynucleotide, each nucleic acid probe having a different oligonucleotide tag;
    combining in a reaction mixture the plurality of nucleic acid probes with the target polynucleotides so that substantially every target polynucleotide associates with a nucleic acid probe to form a selected nucleic acid probe that is resistant to a nuclease activity, the plurality of nucleic acid probes having a size sufficiently greater than the number of target polynucleotides so that substantially every selected nucleic acid probe has a unique oligonucleotide tag;
    isolating the selected nucleic acid probes by treating the reaction mixture with a nuclease having the nuclease activity; and
    determining nucleotide sequences of oligonucleotide tags in a sample of isolated selected nucleic acid probes to determine the number of different oligonucleotide tags therein, thereby determining the number of target polynucleotide in the mixture.

13. The method of claim 12 wherein said target polynucleotide is a restriction fragment having at least one unique sequence overhang and wherein each of said nucleic acid probes is an adaptor having an overhang on each end, one adaptor overhang being complementary to one overhang of the restriction fragment and another adaptor overhang being complementary to another overhang of the restriction fragment so that upon ligation a double stranded DNA circle is formed.

14. The method of claim 13 wherein said restriction fragment is formed by digesting genomic DNA with at least one type us restriction endonuclease.

15. The method of claim 13 wherein said step of determining further includes forming one or more concatenates of oligonucleotide tags from said sample and sequencing the one or more concatenates.

16. The method of claim 13 wherein said at least one type us restriction endonuclease is a double cleavage type us restriction endonuclease.

17. A method of estimating a number of target polynucleotides in a mixture, the method comprising the steps of:
    labeling by sampling each target polynucleotide in the mixture so that substantially every target polynucleotide has a unique oligonucleotide tag;
    amplifying the oligonucleotide tags of the labeled target polynucleotides; and
    determining the number of different oligonucleotide tags in a sample of amplified oligonucleotide tags by determining nucleotide sequences thereof, thereby estimating the number of target polynucleotides in the mixture.

18. The method of claim 17 wherein said step of amplifying is carried out by emulsion PCR.

19. The method of claim 18 wherein said step of determining is carried out by a DNA sequencing technology selected from the group consisting of pyrosequencing, Sanger-based sequencing, and ligation-based sequencing.

20. A method of estimating a number of target polynucleotides in a mixture, the method comprising the steps of:
    labeling by sampling each target polynucleotide in the mixture so that substantially every target polynucleotide has a unique metric tag;
    amplifying the metric tags of the labeled target polynucleotides;
    separating the amplified metric tags to form a separation profile of distinct bands; and
    counting the number of distinct bands of metric tags, thereby estimating the number of target polynucleotides in the mixture.

* * * * *

UNITED STATES PATENT AND TRADEMARK OFFICE
CERTIFICATE OF CORRECTION

PATENT NO. : 7,537,897 B2  Page 1 of 1
APPLICATION NO. : 11/656830
DATED : May 26, 2009
INVENTOR(S) : Sydney Brenner It is certified that error appears in the above-identified patent and that said Letters Patent is hereby corrected as shown below:

In Claim 14, Column 94, line 23, replace the word "us." with IIs

In Claim 16, Column 94, line 29, replace the first word "us" with IIs

In Claim 16, Column 94, line 29, after the word "type", replace the word "us" with IIs

Signed and Sealed this

Sixth Day of October, 2009

David J. Kappos
*Director of the United States Patent and Trademark Office*